United States Patent
Raymond et al.

(10) Patent No.: US 6,515,113 B2
(45) Date of Patent: *Feb. 4, 2003

(54) PHTHALAMIDE LANTHANIDE COMPLEXES FOR USE AS LUMINESCENT MARKERS

(75) Inventors: Kenneth N. Raymond; Stephane Petoud, both of Berkeley, CA (US); Seth M. Cohen, Boston, MA (US); Jide Xu, Berkeley, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/507,630

(22) Filed: Feb. 18, 2000

(65) Prior Publication Data

US 2002/0188111 A1 Dec. 12, 2002

Related U.S. Application Data

(60) Provisional application No. 60/120,881, filed on Feb. 18, 1999.

(51) Int. Cl.[7] ............................ C07F 5/00; G01N 33/533
(52) U.S. Cl. ............................ 534/15; 424/1.11; 435/4; 435/6; 436/546; 436/804; 534/16
(58) Field of Search ..................................... 534/15, 16

(56) References Cited

U.S. PATENT DOCUMENTS 5,049,280 A * 9/1991 Raymond
5,820,849 A   10/1998 Schmitt-Willich et al. . 424/9.36

FOREIGN PATENT DOCUMENTS

| CA | 2099542 | 7/1993 | ......... C07D/493/04 |
| EP | 0 578 067 A1 | 1/1994 | ......... G01N/33/533 |
| WO | WO 92/11039 | 7/1992 | .......... A61K/49/02 |

OTHER PUBLICATIONS

Blomberg, et al., "Terbium and rhodamine as labels in a homogeneous time–resolved fluorometric energy transfer assay of the β subunit of human chorionic gonadotropin in serum", *Clinical Chemistry*, 45(6):855–861 (1999).
Bünzli, et al., "Towards materials with planned properties: dinuclear f–f helicates and d–f non–covalent podates based on benzimidazole–pyridine binding units", *Journal of Alloys and Compounds*, 249:14–24 (1997).
Chen, et al., "Lifetime– and color–tailored fluorophores in the micro– to millisecond time regime", *J. Am. Chem. Soc.*, 122(4):657–660 (2000).

Dickins, et al., "Synthesis, time–resolved luminescence, NMR spectroscopy, circular dichroism and circularly polarised luminescence studies of enantiopure macrocyclic lanthanide tetraamide complexes", *Chem. Eur. J.*, 5(3):1095–1105 (1999).
Dickson, et al., "Time–resolved detection of lanthanide luminescence for ultrasensitive bioanalytical assays", *Journal of Photochemistry and Photobiology, B:Biology*, 27:3–19 (1995).
Galaup, et al., "Mono(di)nuclear europium(III) complexes of macrobi(tri)cyclic cryptands derived from diazatetralactams as luminophores in aqueous solution", *Helvetica Chimica Acta*, 82:543–560 (1999).
Hemmilä, et al., "Development of luminescent lanthanide chelate labels for diagnostic assays", *Journal of Alloys and Compounds*, 249:158–162 (1997).
de Sá, et al., "Spectroscopic properties and design of highly luminescent lanthanide coordination complexes", *Coordination Chemistry Reviews*, 196:165–195 (2000).
Sabbatini, et al., "Luminescent lanthanide complexes as photochemical supramolecular devices", *Coordination Chemistry Reviews*, 123:201–228 (1993).
Saha, et al., "Time–resolved fluorescence of a new europium chelate complex: Demonstration of highly sensitive detection of protein and DNA samples", *J. Am. Chem. Soc.*, 115:11032–11033 (1993).
Soini, et al., "Time–resolved fluorescence of lanthanide probes and applications in biotechnology", *CRC Critical Reviews in Analytical Chemistry*, 18(2):105–154 (1987).
Steemers, et al., "Water–soluble neutral calix[4]arene–lanthanide complexes: Synthesis and luminescence properties", *J. Org. Chem.*, 62:4229–4235 (1997).
Stenroos, et al., "Homogeneous time–resolved IL–2IL–2Rα assay using fluorescence resonance energy transfer", *Cytokine*, 10(7):495–499 (Jul., 1998).
Veiopoulou, et al., "Comparative study of fluorescent ternary terbium complexes. Application in enzyme amplified fluorimetric immunoassay for α–fetoprotein", *Analytica Chimica Acta*, 335:177–184 (1996).
Vicentini, et al., "Luminesence and structure of europium compounds", *Coordination Chemistry Reviews*, 196:353–382 (2000).

* cited by examiner

*Primary Examiner*—Mary E. Ceperley
(74) *Attorney, Agent, or Firm*—Townsend and Townsend and Crew LLP

(57) ABSTRACT

The present invention provides luminescent lanthanide metal chelates comprising a metal ion of the lanthanide series and a complexing agent comprising at least one phthalamidyl moiety. Also provided are probes incorporating the phthalamidyl ligands of the invention and methods utilizing the ligands of the invention and probes comprising the ligands of the invention.

5 Claims, 23 Drawing Sheets

PHTHALAMIDE LANTHANIDE COMPLEXES FOR USE AS LUMINESCENT MARKERS

CROSS-REFERENCES TO RELATED APPLICATIONS

This application claims priority to U.S. Provisional Patent Application Serial No. 60/120,881, filed on Feb. 18, 1999. This application is also related to U.S. Provisional Patent Application Serial No. 60/120,600, filed on Feb. 18, 1999 and U.S. patent application Ser. No. 09/507,599, and filed on an even date herewith. Each of these documents are incorporated herein by reference in their entirety for all purposes.

STATEMENT AS TO RIGHTS TO INVENTIONS MADE UNDER FEDERALLY SPONSORED RESEARCH AND DEVELOPMENT

This work was partially supported by grants from the National Institutes of Health (DK32999) and the United States Department of Energy (DEAC0376F00098). The Government may have rights in the subject matter disclosed herein.

BACKGROUND OF THE INVENTION

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, pharmaceuticals, metabolites, microorganisms and other materials of diagnostic value. Examples of such materials include small molecular bioactive materials (e.g., narcotics and poisons, drugs administered for therapeutic purposes, hormones), pathogenic microorganisms and viruses, antibodies, and enzymes and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations, such labels are, however, expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest, because of the large number of such labels that are known in the art. Moreover, the literature is replete with syntheses of fluorescent labels that are derivatized to allow their facile attachment to other molecules, and many such fluorescent labels are commercially available.

In addition to being directly detected, many fluorescent labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, or other, interactions. An excellent example of the use of fluorescent reporter quencher pairs is found in the detection and analysis of nucleic acids.

An alternative detection scheme, which is theoretically more sensitive than autoradiography, is time-resolved fluorimetry. According to this method, a chelated lanthanide metal with a long radiative lifetime is attached to a molecule of interest. Pulsed excitation combined with a gated detection system allows for effective discrimination against short-lived background emission. For example, using this approach, the detection and quantification of DNA hybrids via an europium-labeled antibody has been demonstrated (Syvanen et al., *Nucleic Acids Research* 14: 1017–1028 (1986)). In addition, biotinylated DNA was measured in microtiter wells using Eu-labeled strepavidin (Dahlen, *Anal. Biochem*, 164: 78–83 (1982)). A disadvantage, however, of these types of assays is that the label must be washed from the probe and its fluorescence developed in an enhancement solution. A further drawback has been the fact that the fluorescence produced has only been in the nanosecond (ns) range, a generally unacceptably short period for adequate detection of the labeled molecules and for discrimination from background fluorescence.

In view of the predictable practical advantages it has been generally desired that the lanthanide chelates employed should exhibit a delayed fluorescence with decay times of more than 10 $\mu$s. The fluorescence of many of the known fluorescent chelates tends to be inhibited by water. As water is generally present in an assay, particularly an immunoassay system, lanthanide complexes that undergo inhibition of fluorescence in the presence of water are viewed as somewhat unfavorable or impractical for many applications. Moreover, the short fluorescence decay times is considered a disadvantage of these compounds. This inhibition is due to the affinity of the lanthanide ions for coordinating water molecules. When the lanthanide ion has coordinated water molecules, the absorbed light energy (excitation energy) is transferred from the complex to the solvent rather than being emitted as fluorescence.

Thus, lanthanide chelates, particularly coordinatively saturated chelates having excellent fluorescence properties are highly desirable. In the alternative, coordinatively unsaturated lanthanide chelates that exhibit acceptable fluorescence in the presence of water are also advantageous. Such chelates that are derivatized to allow their conjugation to one or more components of an assay, find use in a range of different assay formats. The present invention provides these and other such compounds and assays using these compounds.

SUMMARY OF THE INVENTION

Luminescent (including fluorescent and phosphorescent) markers find a wide variety of applications in science, medicine and engineering. In many situations, these markers provide competitive replacements for radiolabels, chromogens, radiation-dense dyes, etc. Moreover, improvements in fluorimetric instrumentation have increased attainable sensitivities and permitted quantitative analysis.

Lanthanide chelates in combination with time-resolved fluorescent spectroscopy is a generally accepted immunochemical tool. Presently preferred lanthanide ions include $Dy^{3+}$, $Sm^{3+}$, $Tb^{3+}$, $Er^{3+}$ and $Eu^{3+}$, $Nd^{3+}$, Yb3+. Other lanthanide ions, such as $La^{3+}$, $Gd^3+$ and $Lu^3+$ are useful, but generally less preferred.

The present invention provides lanthanide complexes that are extremely luminescent and possess many features desired for fluorescent markers and probes of use in fluorescent assay systems. Among these advantages are: 1) ligands acting as both chelators and chromophore/energy transfer devices; 2) very high quantum yields of lanthanide ion fluorescence of the present complexes in water without external augmentation, such as by micelles or fluoride; 3) high stability and solubility of these complexes in water; 4) an extremely easy synthesis that employs inexpensive starting materials; and 5) facile access to many derivatives for linking these luminescent probes to, for example, an immunoreactive agent or solid support (e.g., polymer).

The present invention provides a new class of lanthanide-complexing ligands that incorporate hydroxyisophthamidylic acid moieties within their structures and luminescent metal complexes of these ligands. The compounds of the invention include hydroxyisophthamidylamide-based bidentate, tetradentate and other higher polydentate ligands. The compounds of the invention are easily prepared in good yields.

Thus, in a first aspect, the present invention provides a luminescent lanthanide metal chelate comprising a metal ion of the lanthanide series and a complexing agent comprising at least one phthalamidyl moiety.

In a second aspect, the invention provides a compound having a structure according to Formula I:

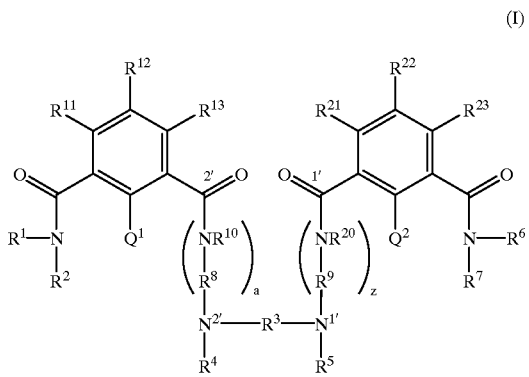

(I)

In Formula I, $R^1$, $R^2$, $R^4$, $R^5$, $R^6$, $R^7$, $R^{10}$ and $R^{20}$ are members independently selected from the group consisting of H, alkyl and substituted alkyl groups, wherein, two or more of $R^2$, $R^4$, $R^5$, $R^7$ and, when $R^3$ is substituted alkyl, a substituent of $R^3$ are optionally adjoined by at least one linker moiety to form at least one ring. $R^3$, $R^8$ and $R^9$ are members independently selected from the group consisting of alkyl, substituted alkyl, aryl and substituted aryl groups. $R^{11}$, $R^{12}$, $R^{13}$, $R^{21}$, $R^{22}$ and $R^{23}$ are members independently selected from alkyl, substituted alkyl, H, —$NR^{14}R^{15}$, —$NO_2$, —$OR^{16}$, —$COOR^{17}$, wherein, $R^{14}$, $R^{15}$, $R^{16}$ and $R^{17}$ are members independently selected from the group consisting of H, alkyl and substituted alkyl, wherein $R^{12}$ can optionally form a ring with $R^{11}$, $R^{13}$ or both, and $R^{22}$ can optionally form a ring with $R^{21}$, $R^{23}$ or both. The rings are members independently selected from the group of ring systems consisting of cyclic alkyl, substituted cyclic alkyl, aryl, substituted aryl, heteroaryl, substituted heteroaryl, heterocyclyl and saturated heterocyclyl ring systems. $Q^1$ is —$OR^{18}$ and $Q^2$ is —$OR^{19}$, wherein $R^{18}$ and $R^{19}$ are members independently selected from H, an enzymatically labile group, a hydrolytically labile group and a single negative charge. The letter a is 0 or 1, with the proviso that when a is 0, $N^{2'}$ is covalently attached directly to carbonyl group 2' and z is 0 or 1, with the proviso that when z is 0, $N^{1'}$ is covalently attached directly to carbonyl group 1'.

In addition to the ligands and lanthanide complexes, the present invention also provides a number of methods, including assays utilizing the compounds of the invention. The assays of the invention preferably utilize the fluorescence of the compounds described herein to detect the subject of the assay. The methods of the invention allow the detection of, for example, small molecular bioactive materials and biomolecules at trace concentrations without using radioactive species.

DETAILED DESCRIPTION OF THE INVENTION AND THE PREFERRED EMBODIMENTS

Abreviations

Figure 1:
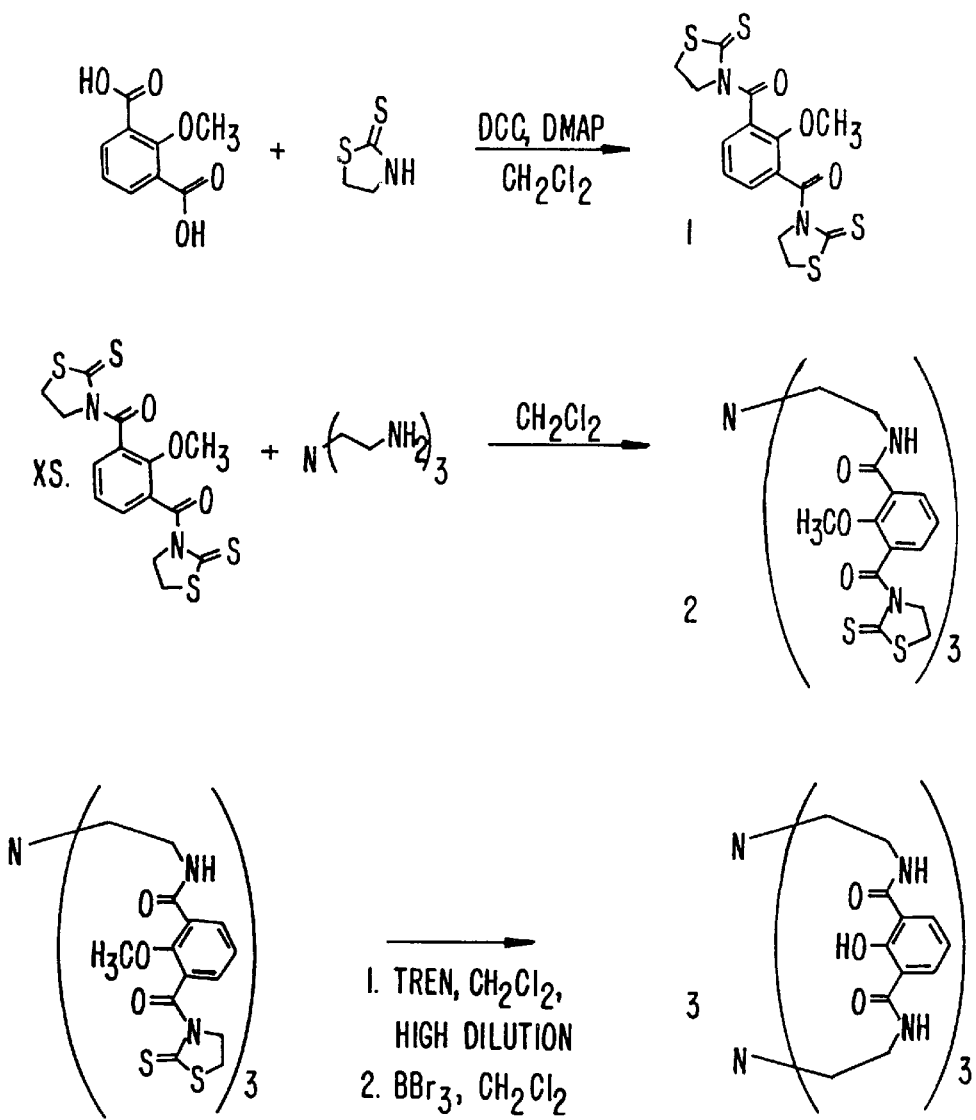
FIG. 1 is an exemplary synthetic scheme leading to the ligand $H_3$(bicapped TRENSAM).2HBr FIGS. 2(A–B) are experimental (A) and calculated (B) spectra from the titration of bicapped TRENSAM with $EuCl_3$ in buffered aqueous solution.

As used herein, "PL," refers to the phthalamidyl derived ligands of the invention. "PL" encompasses the ligands of the invention in both their free state and when they have complexed one or more metal ions. Moreover, "PL" encompasses ligands that include one or more phthamidyl groups in combination with one or more salicylamidyl groups ("PSL").

Definitions

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those known and employed in the art. Standard techniques, or modifications thereof, are used for chemical syntheses and chemical analyses.

"Analyte", as used herein, means any compound or molecule of interest for which a diagnostic test is performed, such as a biopolymer or a small molecular bioactive material. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group of the invention. There is no limitation on the identity of the individual members of the energy transfer pair in this application. All that is required is that the spectroscopic properties of the energy transfer pair as a whole change in some measurable way if the distance between the individual members is altered by some critical amount.

"Energy transfer pair" is used to refer to a group of molecules that form a single complex within which energy transfer occurs. Such complexes may comprise, for example, two fluorescent groups, which may be different from one another and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "fluorescence-modifying group" refers to a molecule of the invention that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

"Fluorescence resonance energy transfer" or "FRET" is used interchangeably with FET, and refers to an energy transfer phenomenon in which the light emitted by the excited fluorescent group is absorbed at least partially by a fluorescence-modifying group of the invention. If the fluorescence-modifying group is a quenching group, then that group will preferably not radiate a substantial fraction of the absorbed light as light of a different wavelength, and will preferably dissipate it as heat. FRET depends on an overlap between the emission spectrum of the fluorescent group and the absorption spectrum of the quenching group. FRET also depends on the distance between the quenching group and the fluorescent group.

"Moiety" refers to the radical of a molecule that is attached to another moiety.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a PL, a fluorophore or another moiety.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in Chemistry and Biochemistry of Amino Acids, Peptides and Proteins, B. Weinstein, eds., Marcel Dekker, New York, p. 267 (1983).

The term "alkyl" is used herein to refer to a branched or unbranched, saturated or unsaturated, monovalent hydrocarbon radical, generally having from about 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl."

"Substituted alkyl" refers to alkyl as just described including one or more substituents such as lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein to refer to an aromatic substituent, which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defined herein.

The term "acyl" is used to describe a ketone substituent, —(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to —NRR', wherein R and R' are independently H, alkyl, aryl or substituted analogues thereof. "Amino" encompasses "alkylamino" denoting secondary and tertiary amines and "acylamino" describing the group RC(O)NR'.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "aryloxy" denotes aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure —S—R wherein R is H, alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to another group.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to another group.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group.

Introduction

The present invention provides a class of luminescent probes that are based on metal chelates of phthalamidyl-based ligands ("PL"), particularly chelates of the lanthanide series. Other compounds of the invention include both phthamidyl and salicylamidyl moieties in a single ligand ("PSL"). The compounds of the invention emit light or they can be used to absorb light emitted by a reporter fluorophore. The fluorophores of the invention can be used as small molecules in solution assays or they can be utilized as a label that is attached to an analyte or a species that interacts with, and allows detection and/or quantification of an analyte.

Fluorescent labels have the advantage of requiring few precautions in their handling, and being amenable to high-throughput visualization techniques (optical analysis including digitization of the image for analysis in an integrated system comprising a computer). Preferred labels are typically characterized by one or more of the following: high sensitivity, high stability, low background, long lifetimes, low environmental sensitivity and high specificity in labeling.

The fluorophores of the invention can be used with other fluorophores or quenchers as components of energy transfer probes. Many fluorescent labels are useful in combination with the PL and PSL of the invention. Many such labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available conmmercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful with the PLs and PSLs of the present invention. Such proteins include, for example, green fluorescent proteins of cnidarians (Ward et al., *Photochem. Photobiol.* 35:803–808 (1982); Levine et al., *Comp. Biochem. Physiol.*, 72B:77–85 (1982)), yellow fluorescent protein from Vibrio fischeri strain (Baldwin et al., *Biochemistry* 29:5509–15 (1990)), Peridinin-chlorophyll from the dinoflagellate Symbiodinium sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226–35 (1993)), and the like.

The compounds of the invention can be used as probes, as tools for separating particular ions from other solutes, as probes in microscopy, enzymology, clinical chemistry, molecular biology and medicine. The compounds of the invention are also useful as therapeutic agents in modalities, such as photodynamic therapy and as diagnostic agents in imaging methods, such as magnetic resonance imaging. Moreover, the compounds of the invention are useful as components of optical amplifiers of light, waveguides and the like. Furthermore, the compounds of the invention can be incorporated into inks and dyes, such as those used in the printing of currency or other negotiable instruments.

The compounds of the invention can be made to luminesce by exciting them in any manner known in the art, including, for example, with light or electrochemical energy (see, for example, Kulmala et al, *Analytica Chimica Acta* 386: 1 (1999)). The luminescence can, in the case of chiral compounds of the invention, be circularly polarized (see, for example, Riehl et al., *Chem. Rev.* 86: 1 (1986)).

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

The Compounds

The present invention provides an anay of phthalamidyl-based metal chelating ligands ("PL") that comprise at least one phthamidyl moiety within their framework. The PL compounds can also include one or more salicylamidyl moiety within their framework in combination with the one or more phthalamidyl moiety.

In one aspect, the invention provides a luminescent lanthanide ion complex. The chelating group comprises at least one phthalamidyl group, preferably between 2 and 100 phthamidyl groups, more preferably between 3 and 75 phthamidyl groups, even more preferably between 4 and 50 phthalamidyl groups and more preferably still, between 5 and 25 phthamidyl groups. The complex also, preferably has a quantum yield of at least about 0.1. Even more preferably, the lanthanide ion of the complex is a member selected from europium, terbium and combinations thereof.

The at least one phthalamidyl group of the chelating group can be substituted with one or more electron withdrawing and/or electron donating group. Those of skill in the art will understand which substituents, when appended to an aromatic ring will exhibit electron withdrawing or electron donating properties. Tables of substituents that are appropriate for inclusion in the PLs of the invention can be found in the literature. See, for example, Hammett, *J. Am. Chem. Soc.* 59: 96 (1937); Johnson, THE HAMMET EQUATION, Cambridge University Press, New York, 1973; Hansch et al., *J. Med. Chem.* 16: 1207 (1973); and Hansch et al., SUBSTITUENT CONSTANTS FOR CORRELATION ANALYSIS IN CHEMISTRY AND BIOLOGY, Wiley, New York, 1979.

Moreover, the phthalamidyl groups of the complex can be connected by a backbone of substantially any length and chemical composition, with the proviso that the backbone should orient the phthalamidyl and other rings in a manner that is conducive to their complexation of the desired metal ion. That the backbone be stable to the conditions in which the complex is used is also generally preferred. As such, representative backbones include, for example, alkyl groups, substituted alkyl groups, conjugated unsaturated systems, aryl groups, heteroaryl groups, dendrimers, polyethers, polyamides, polyimines, biopolymers and backbones that are a combination of more than one of these groups. Other useful backbone systems will be apparent to those of skill in the art.

In a second aspect, the present invention provides a compound having a structure according to Formula I:

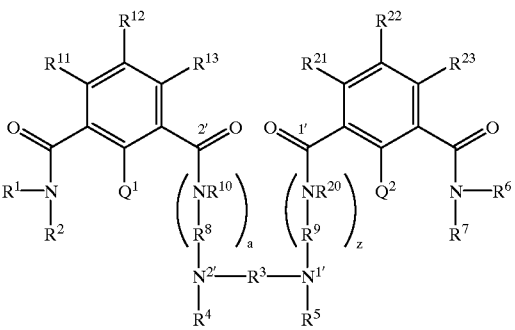

(I)

In Formula I, the groups $R^1$, $R^2$, $R^4$, $R^5$, $R^6$, $R^7$, $R^{10}$ and $R^{20}$ are members independently selected from the group consisting of H, alkyl and substituted alkyl groups, wherein, two or more of $R^2$, $R^4$, $R^5$, $R^7$ and, when $R^3$ is substituted alkyl, a substituent of $R^3$ are optionally adjoined by at least one linker moiety to form at least one ring. $R^3$, $R^8$ and $R^9$ are members independently selected from the group consisting of alkyl, substituted alkyl, aryl and substituted aryl groups. $R^{11}$, $R^{12}$, $R^{13}$, $R^{21}$, $R^{22}$ and $R^{23}$ are members independently selected from alkyl, substituted alkyl, H, —$NR^{14}R^{15}$, —$NO_2$, —$OR^{16}$, —$COOR^{17}$, wherein, $R^{14}$, $R^{15}$, $R^{16}$ and $R^{17}$ are members independently selected from the group consisting of H, alkyl and substituted alkyl, wherein $R^{12}$ can optionally form a ring with $R^{11}$, $R^{13}$ or both, and $R^{22}$ can optionally form a ring with $R^{21}$, $R^{23}$ or both. The rings are members independently selected from the group of ring systems consisting of cyclic alkyl, substituted cyclic alkyl, aryl, substituted aryl, heteroaryl, substituted heteroaryl, heterocyclyl and saturated heterocyclyl ring systems. $Q^1$ is —$OR^{18}$ and $Q^2$ is —$OR^9$. $R^{18}$ and $R^{19}$ are members independently selected from H, an enzymatically labile group, a hydrolytically labile group and a single negative charge. The number represented by a is 0 or 1, with the proviso that when a is 0, $N^2$ is covalently attached directly to carbonyl group 2'. Similarly, z is 0 or 1, with the proviso that when z is 0, $N^{1'}$ is covalently attached directly to carbonyl group 1'.

Although the complexing agents of the invention can have any useful number of phthalamidyl rings, in a preferred embodiment, z is 0, generally affording a complexing agent having three phthalamidyl rings.

As discussed above, the backbone, here represented by $R^3$, can have any useful structure and size, so long as it is functionalized to allow at least one phthamidyl group to be attached thereto. In a preferred embodiment, $R^3$ is a linear $C_1$–$C_6$ hydrocarbon.

In another preferred embodiment, the present invention provides a compound having three phthalamidyl rings. The compound has a structure according to Formula I, in which $R^8$ is $(CH_2)_P$, wherein P is selected from the group consisting of the integers from 1 to 5, inclusive. $R^4$ provides the third phthalamidyl ring and is an alkyl group substituted with a moiety having a structure according to Formula II:

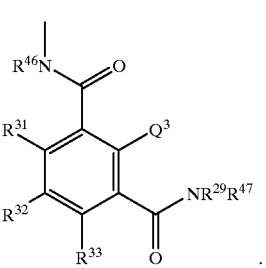

(II)

In Formula II, $R^{29}$, $R^{46}$ and $R^{47}$ are members independently selected from the group consisting of H, alkyl and substituted alkyl groups, wherein, two or more of $R^2$, $R^7$ and $R^{29}$ are optionally adjoined by at least one linker moiety to form at least one ring. $R^{31}$, $R^{32}$ and $R^{33}$ are members independently selected from alkyl, substituted alkyl, H, —$NR^{24}R^{25}$, —$NO_2$, —$OR^{26}$, —$COOR^{27}$, wherein, $R^{24}$, $R^{25}$, $R^{26}$ and $R^{27}$ are members independently selected from the group consisting of H, alkyl and substituted alkyl, wherein $R^{32}$ can optionally form a ring with $R^{31}$, $R^{33}$ or both. The rings are members independently selected from the group of ring systems consisting of cyclic alkyl, substituted cyclic alkyl, aryl, substituted aryl, heteroaryl, substituted heteroaryl, heterocyclyl and saturated heterocyclyl ring systems. $R^3$ is $(CH_2)_X$, wherein P is selected from the group consisting of the integers from 1 to 5, inclusive. $Q^3$—$OR^{28}$, wherein $R^{28}$ is a member selected from H, an enzymatically labile group, a hydrolytically labile group and a single negative charge. In this embodiment, z from Formula I is 0.

In further preferred embodiment, the compounds of the invention are macrocyclic or polymacrocyclic structures. Representative of this embodiment is a compound whose structure includes the moieties set forth in Formulae I and II and in which two or more of $R^2$, $R^7$ and $R^{29}$ are adjoined by at least one linker moiety to form at least one ring, more preferably, $R^2$, $R^7$ and $R^{29}$ together comprise a single linker moiety.

Although the linker moieties used to form the macrocyclic or polymacrocyclic structures can have substantially any useful structure, including for example, alkyl, substituted alkyl, arylalkyl, heteroarylalkyl, conjugated unsaturated systems, aryl groups, heteroaryl groups, dendrimers, polyethers, polyamides, polyimines, biopolymers and backbones that are a combination of more than one of these groups, a presently preferred linker has a structure according to Formula III:

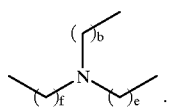

(III)

In Formula III, b, e and f are members independently selected from the group consisting of the integers from 1 to 5, inclusive.

In a still further preferred embodiment, the invention provides a compound having a structure according to Formula IV:

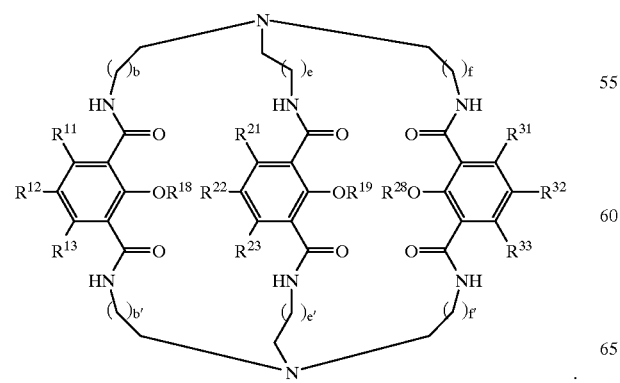

(IV)

In Formula IV, b, b', e, e', f and f' are members independently selected from the group consisting of the integers from 1 to 5, inclusive.

In still further preferred embodiments, the invention provides compounds having a structure according to Formula V:

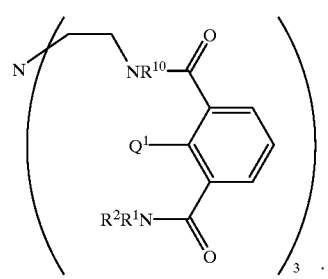

(V)

or more preferably still, Formula VI:

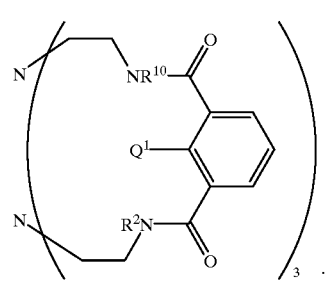

(VI)

In Formulae V and VI, $R^1$, $R^2$, $R^{10}$ and $Q^1$ represent the same species as those described in conjunction with the compound according to Formula I. In each of Formulae IV–VI, the substituents (R) are substantially as described above.

In another preferred embodiment, the invention provides a compound with a minimum of four phthalamidyl rings. The compound has a structure according to Formula I, wherein $R^4$ is an alkyl group substituted with a group having a structure according to Formula II, above. The fourth phthalamidyl ring is provided by $R^5$, which is an alkyl group substituted with a moiety having a structure according to Formula IX:

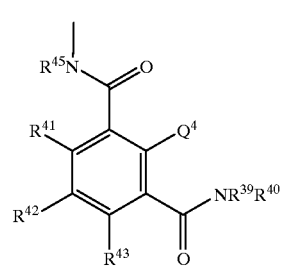

(IX)

In Formula IX, $R^{39}$, $R^{40}$ and $R^{45}$ are members independently selected from alkyl and substituted alkyl groups. $R^{41}$, $R^{42}$ and $R^{43}$ are members independently selected from alkyl, substituted alkyl, H, $-NR^{34}R^{35}$, $-NO_2$, $-OR^{36}$, $-COOR^{37}$, wherein, $R^{34}$, $R^{35}$, $R^{36}$ and $R^{37}$ are members independently selected from the group consisting of H, alkyl and substituted alkyl, wherein $R^{42}$ can optionally form a ring with $R^{41}$, $R^{43}$ or both. The rings are members independently selected from the group of ring systems consisting of cyclic alkyl, substituted cyclic alkyl, aryl, substituted aryl, heteroaryl, substituted heteroaryl, heterocyclyl and saturated heterocyclyl ring systems.

In another preferred embodiment, the invention provides a compound having a structure according to Formula X:

The substituents (R) in Formula XI, have substantially the same identity as identically named substituents in the Formulae above.

In a further preferred example, the invention provides a compound combining Formulae I, II and IX, and in which $R^1$, $R^6$, $R^{29}$ and $R^{39}$ together comprise a single linker moiety. The linker preferably has a structure according to Formula XII:

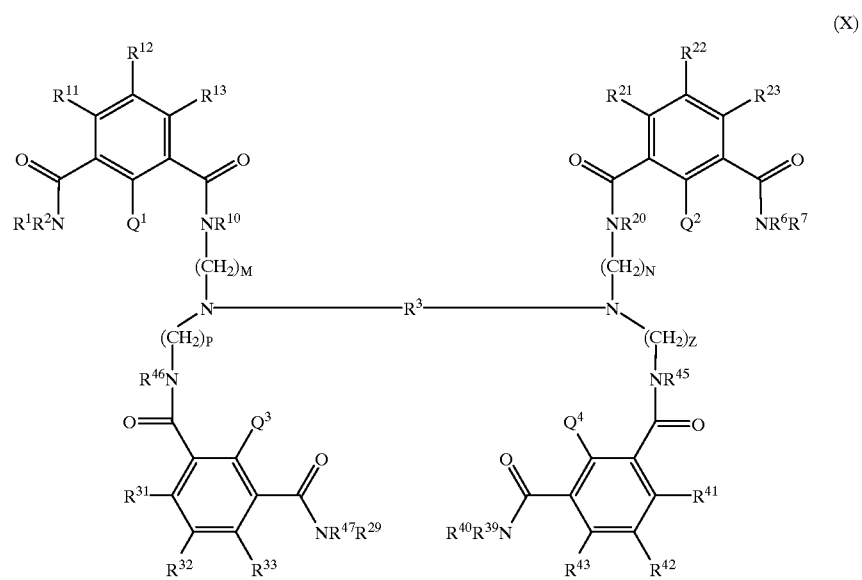

(X)

In Formula X, the letters M, N, P and Z represent numbers that are members independently selected from the group consisting of the integers between 1 and 5, inclusive.

In another preferred embodiment, the present invention provides a having a structure according to Formula XI:

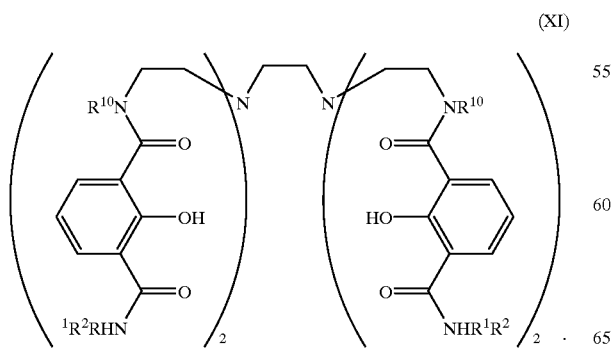

(XI)

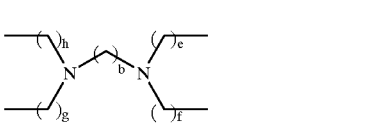

(XII)

In Formula XII, b, e, f, g and h are members independently selected from the numbers between 1 and 5, inclusive.

In a still further preferred embodiment, the invention provides a compound having a structure according to Formula XIII:

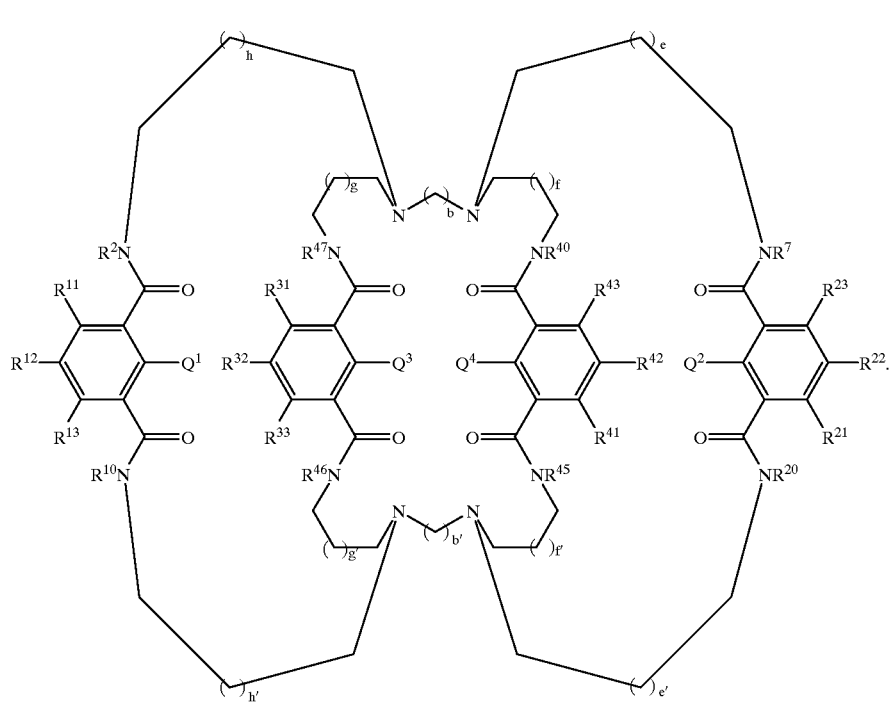

(XIII)

In Figure XIII, b and b' are members independently selected from the group consisting of the integers from 1 to 5, inclusive; e, e', f, f', g, g', h and h' are members independently selected from the group consisting of numbers from 0 to 3. IN each of Formulae X–XIII, the substituents (R") are substantially as described above.

In a still further preferred embodiment, the invention provides compounds having a structure according to Formula XIV:

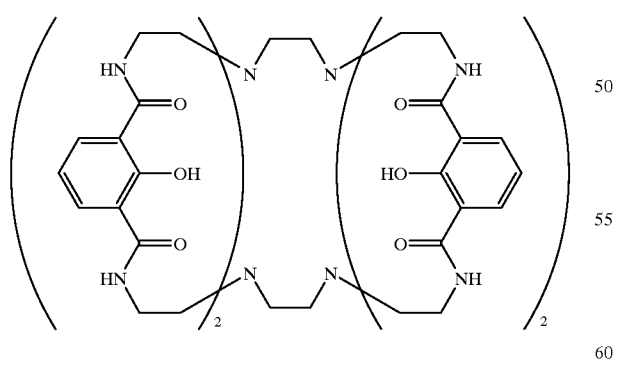

(XIV)

In another preferred embodiment, the backbone of the compound is a dendrimer. Thus, the invention provides compounds having a structure according to Formula XV:

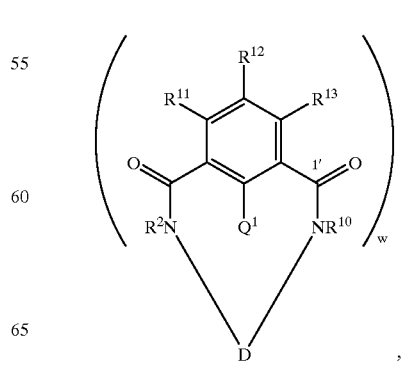

(XV)

In Formula XV, D represents the dendrimer; and w is a member selected from the group consisting of the integers from 4 to 100, inclusive, more preferably between 8 and 50, inclusive.

The PL of the invention can also form macrocyclic ligands, which are bound to the dendrimer or which incorporate constituents of the dendrimer into the macrocyclic framework. A representative of such compounds have has a structure according to Formula XVI:

(XVI)

, in which D and w are as set forth above. It will be apparent to one of skill that the dendrimer and the ligand in each of these structures can be linked by any type of spacer arm, including, for example an amine, such as the backbone amines of the present invention.

In a preferred embodiment of the compounds of Formulae XV and XVI, the dendrimer is a poly(propyleneimine) dendrimer, preferably of generation 2 to generation 10, inclusive.

In yet another preferred embodiment, the invention provides polymacrocyclic compounds. A representative structure of a compound of this embodiment of the invention is set forth in Formula XVII:

In yet another preferred embodiment, one or more of the above-recited R groups is a member selected from the group consisting of H and a primary alkyl amine, preferably a $C_1$ to $C_{10}$ alkyl chain bearing an amine moiety at the ω-position, more preferably a $C_2$ to $C_6$ alkyl chain bearing an amine moiety at the ω-position.

In a still further preferred embodiment, one or more of the above-recited R groups is a polyether, preferably a member selected from ethylene glycol, ethylene glycol oligomers and combinations thereof, having a molecular weight of from about 60 daltons to about 10,000 daltons, and more preferably of from about 100 daltons to about 1,000 daltons.

Representative polyether-based substituents include, but are not limited to, the following structures:

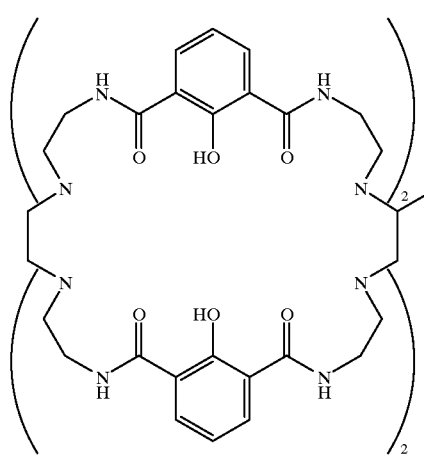
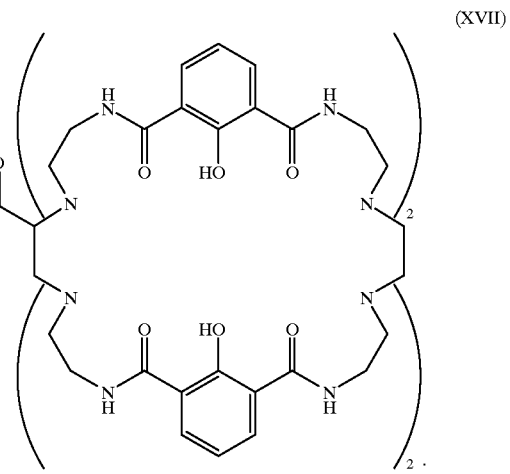

(XVII)

R Groups

For clarity of illustration, the discussion of the identities of the various R groups (e.g., $R^1$, $R^2$, $R^3$, etc.) set forth in the Formulae above is collected together in this section. This discussion is equally applicable to each of the formulae set forth herein. Moreover, although the discussion focuses on certain representative formulae, it is to be understood that this is a device used to simplify the discussion of the R groups and that it does not serve to limit the scope of the R groups.

Referring to Formulae I and II in combination and the resulting complexing agent with three phthalamidyl rings, the following discussion is generally relevant to any compound of the invention and any R group of any compound of the invention. Moreover, this discussion is specifically relevant to the R groups $R^1$, $R^2$, $R^3$, $R^5$, $R^6$, $R^7$, $R^8$, $R^9$, $R^{10}$, $R^{29}$, $R^{46}$ and $R^{47}$. It will be apparent to those of skill in the art that when additional phthalanmdyl rings, linker groups and backbones are included in a compound of the invention, the following discussion is equally relevant to them.

In one preferred embodiment, one or more of the above-recited R groups is a member independently selected from the group consisting of H, $C_1$ to $C_{10}$ alkyl and $C_1$ to $C_{10}$ substituted alkyl, and more preferably members independently selected from the group consisting of H, $C_2$ to $C_6$ alkyl and $C_2$ to $C_6$ substituted alkyl.

In another preferred embodiment, one or more of the above-recited R groups is a member independently selected from the group consisting of H, aryl, substituted aryl and combinations thereof.

In a further preferred embodiment, one or more of the above-recited R groups is a member independently selected from the group consisting of H and alkyl substituted with polycyclic aryl groups, preferably napthyl groups.

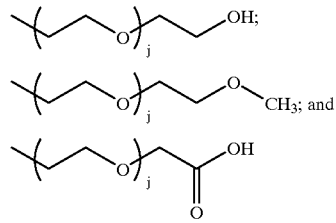

in which j is a number from 1 to 100, inclusive. Other functionalized polyethers are known to those of skill in the art, and many are commercially available from, for example, Shearwater Polymers, Inc. (Alabama).

In another preferred embodiment, one or more of the above-recited R groups comprise a reactive group for conjugating said compound to a member selected from the group consisting of molecules and surfaces. Representative useful reactive groups are discussed in greater detail in the succeeding section. Additional information on useful reactive groups is known to those of skill in the art. See, for example, Hermanson, BIOCONJUGATE TECHNIQUES, Academic Press, San Diego, 1996.

In a preferred embodiment, one or more of the above-recited R groups is a member selected from ω-carboxyl alkyl groups, ω-carboxyl substituted alkyl groups and combinations thereof, more preferably the R group has a structure according to Formula VII:

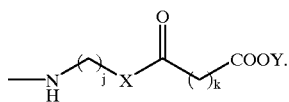

(VII)

In Formula VII, X is a member selected from O, S and NR$^{50}$. R$^{50}$ is a member selected from H, alkyl and substituted alkyl. Y is a member selected from H and a single negative charge; and j and k are members independently selected from the group consisting of integers from 1 to 18.

In a further preferred embodiment, one or more of the above-recited R groups has a structure according to Formula VIII:

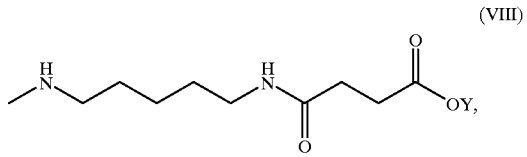

(VIII)

in which Y is substantially as recited above for Formula VII.

In yet another preferred embodiment, one or more of the R groups can combine characteristics of one or more of the above-recited groups. For example, one preferred R group combines both the attributes of a polyether and a reactive group:

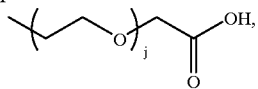

in which j is an integer between 1 and 100, inclusive. Other "chimeric" R groups include, but are not limited to, moieties such as sugars (e.g., polyol with reactive hydroxyl), amino acids, amino alcohols, carboxy alcohols, amino thiols, and the like.

In a still further preferred embodiment, the compounds of the invention have more than one type of R group on a single molecule. For example a single molecule can include an R group that is a polyether and an R group that is an amine. Many other such combinations of different substituents will be apparent to those of skill in the art. Representative structures according to this embodiment are set forth below:

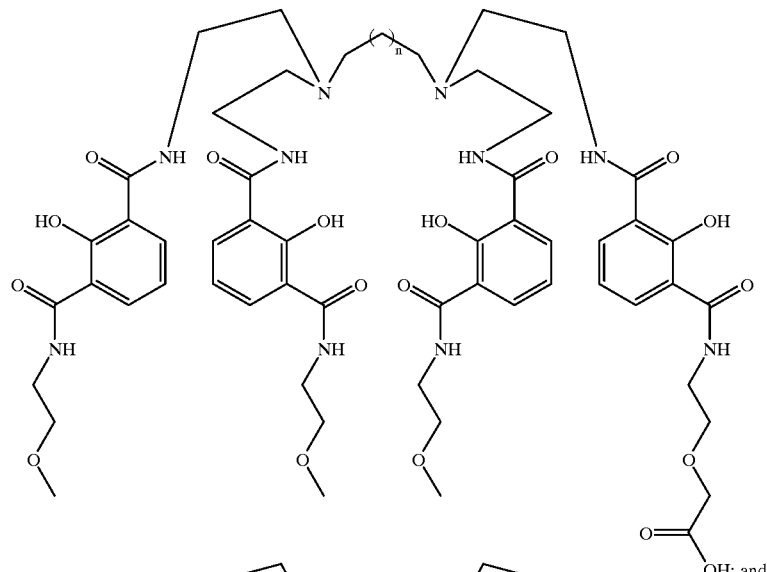

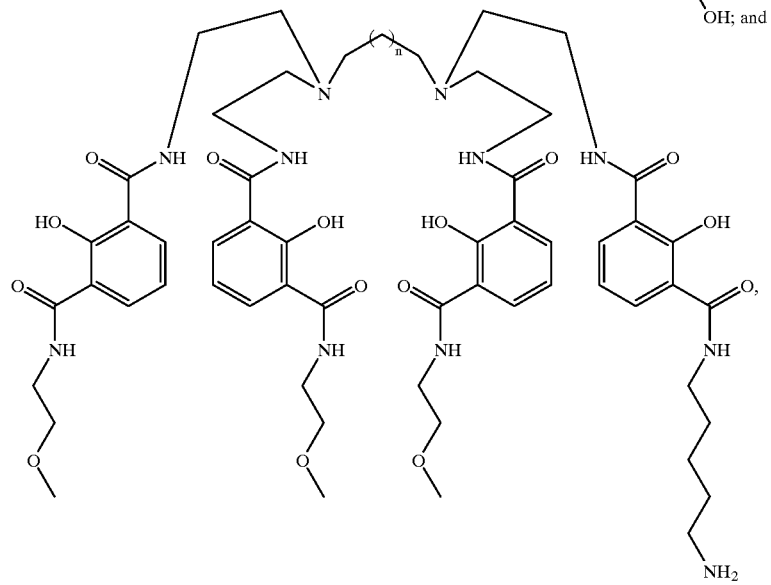

wherein, n is an integer between 0 and 6, and preferably between 1 and 3.

Figure 19A:
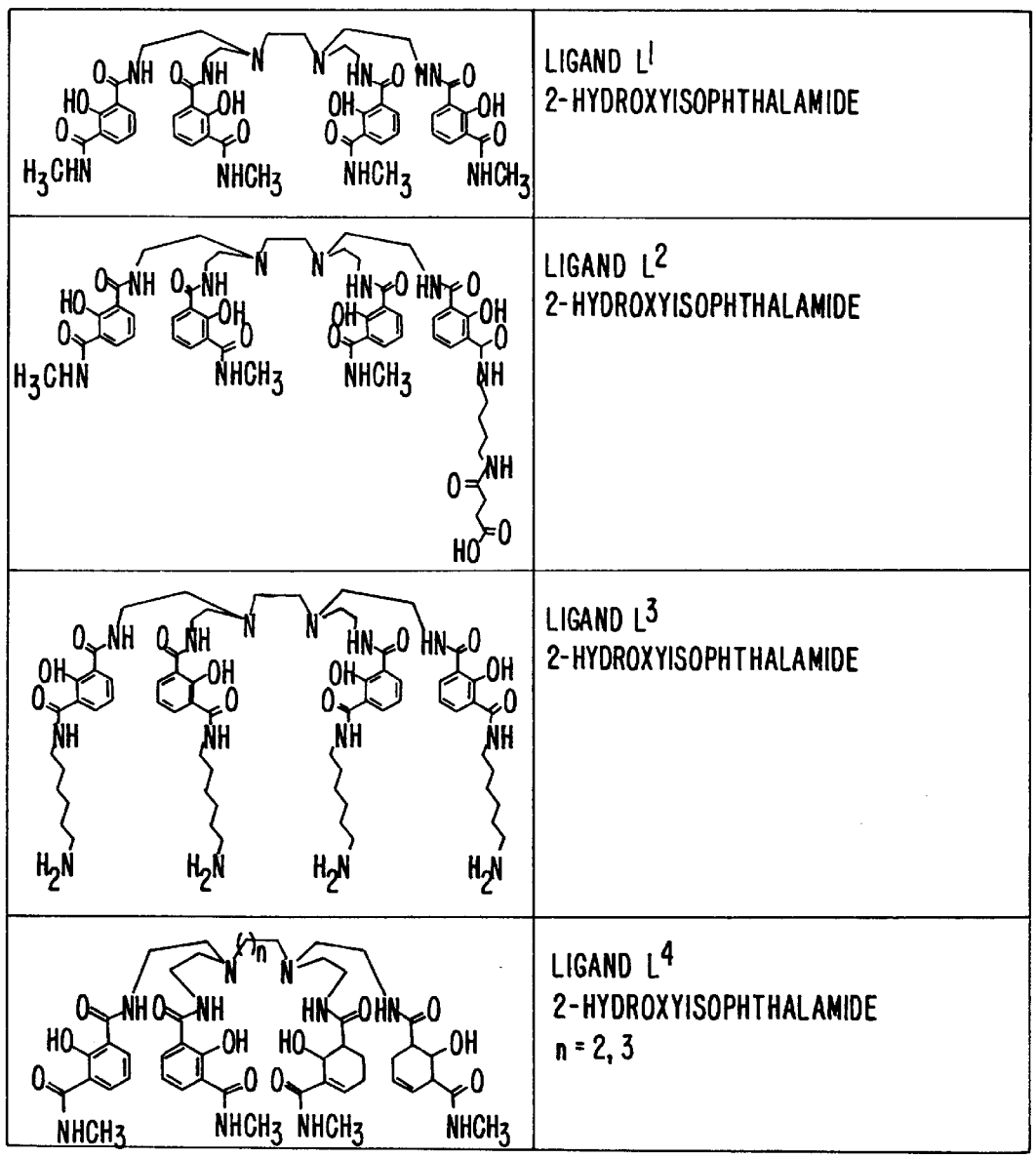
FIG. 19 is a table displaying exemplary compounds of the invention.
Figure 19B:
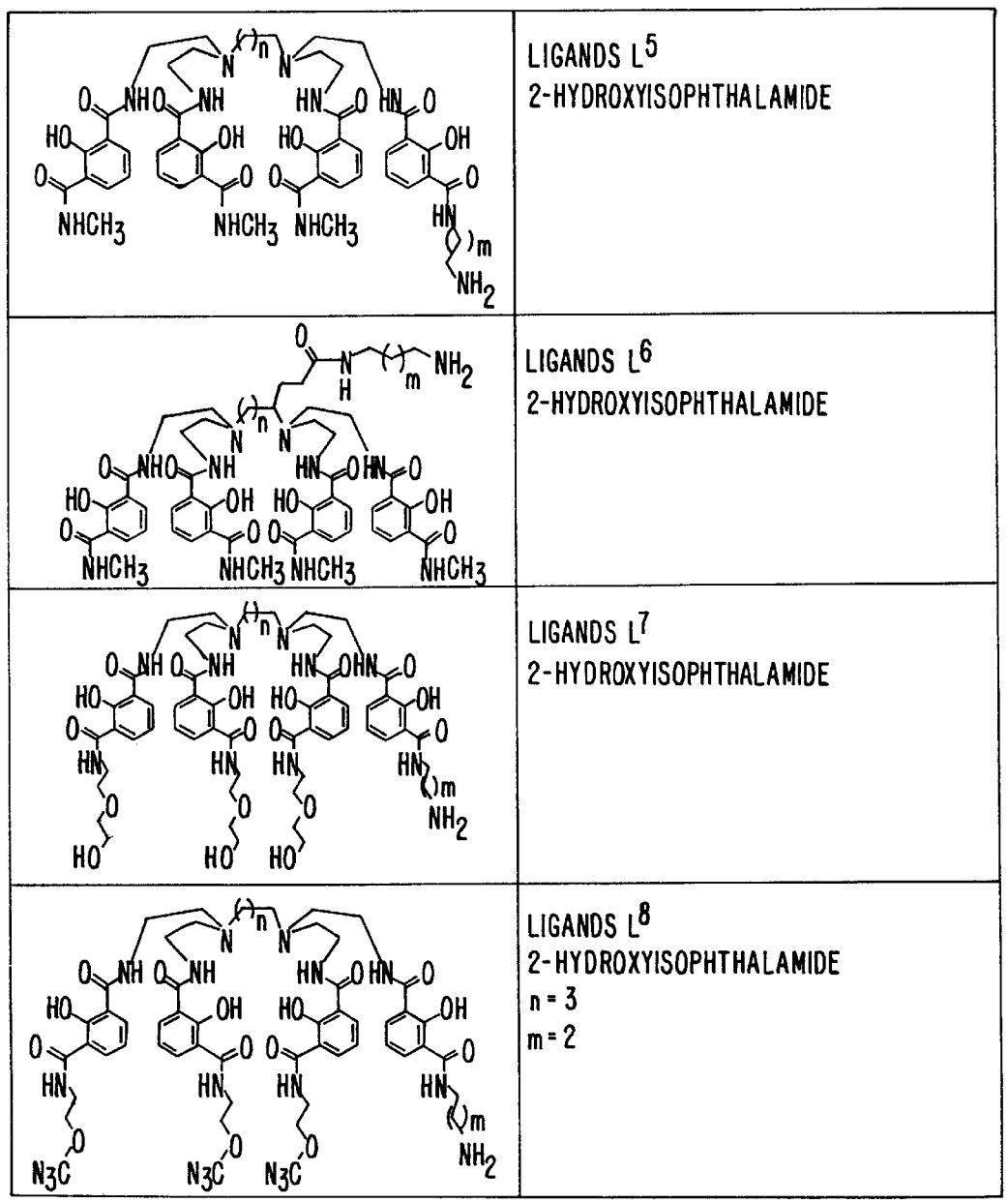
Figure 19C:
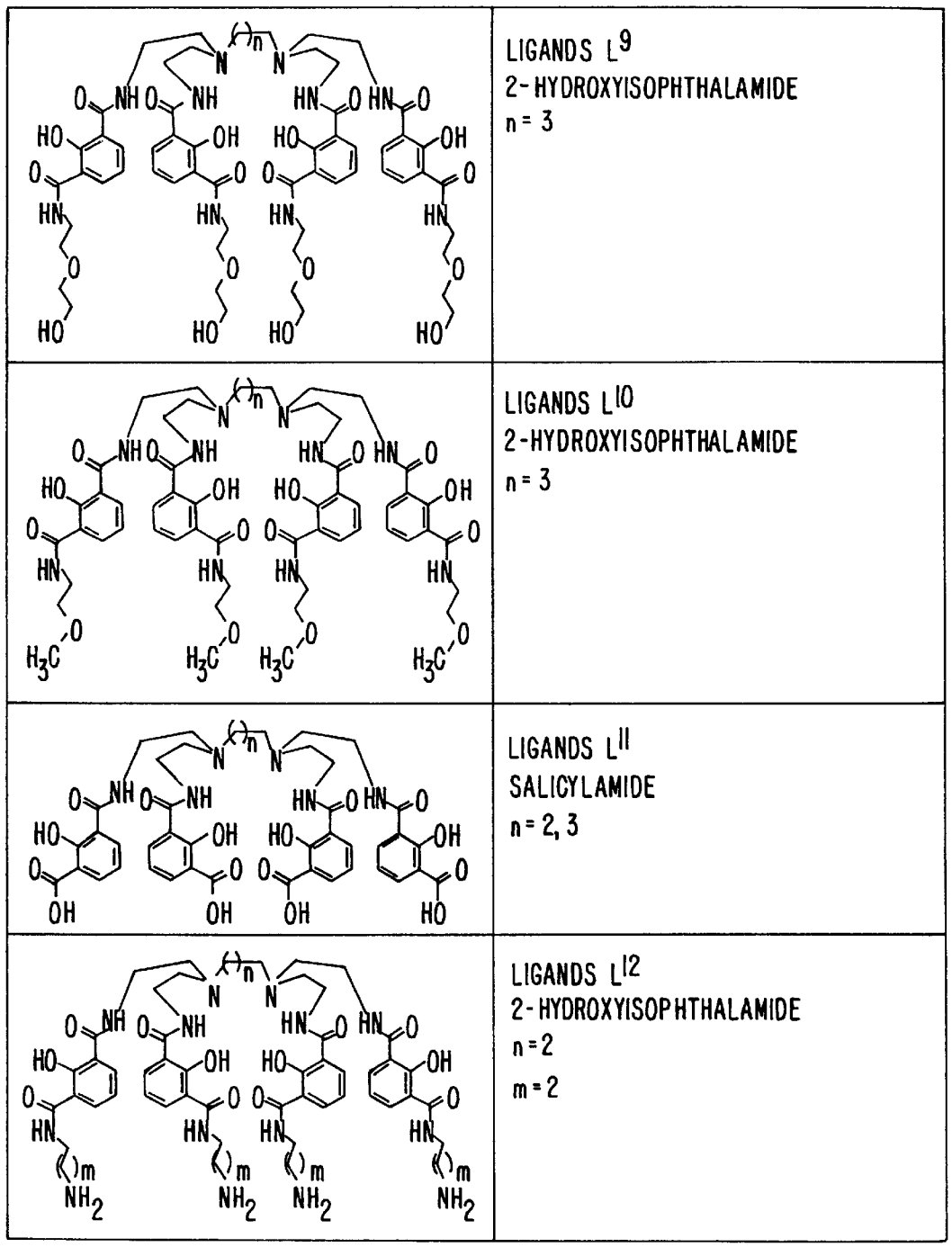

Structural illustrations of certain exemplary compounds of the invention are set forth in FIG. 19.

Exemplary lanthanide chelates of the invention have a structure according to Structure 1:

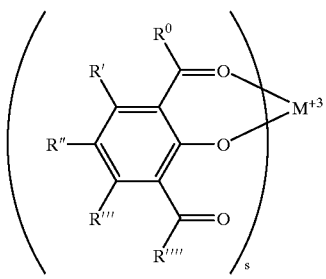

where s is between 1 and 5, inclusive. Exemplary preferred compounds are set forth in Table 1.

TABLE 1

| Denticity | Structure | $R^0$ | $R''''$ |
|---|---|---|---|
| 4 | acyclic | 3(M)Li | methylamine |
| 4 | macrocyclic | 5Li | 5Li |
| 6 | acyclic | TREN | methylamine |
| 6 | macrobicyclic | TREN | 2-AMN |
| 8 | acyclic | H22 | methylamine |
| 8 | macrotricyclic | H22 | H22 |

For all compounds in table 1, R', R'', and R''' are H and $R^0$ and R'''' are amides;
3(M)Li = 2,2-dimethyl-1,3-diaminopropane;
5LI = 1,5-diaminopentane;
TREN = tris(2-aminoethyl)amine;
2-AMN = 2-aminomethylnaphthalene;
H22 = tetrakis(2-aminoethyl)ethylenediamine In yet another preferred embodiment, the compounds of the invention are associated with another molecule by a weak interaction (e.g. van der Waals) to form a species, such as, for example, and inclusion complex. Preferred molecules interacting with the PLs include, but are not limited to dendrimers, macrocycles, cyclodextrins, and the like.

Reactive Functional Groups

Certain of the compounds of the invention bear a reactive functional group, such as a component of a linker arm, which can be located at any position on any aryl nucleus or on a chain, such as an alkyl chain, attached to an aryl nucleus, or on the backbone of the chelating agent. These compounds are referred to herein as "reactive ligands." When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions available with reactive ligands of the invention are those which proceed under relatively mild conditions. These include, but are not limited to nucleophilic substitutions (e.g., reactions of amines and alcohols with acyl halides, active esters), electrophilic substitutions (e.g. enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the reactive ligand. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Donor and Acceptor Moieties

One of the advantages of the compounds of the invention is that they can be used with a wide range of energy donor and acceptor molecules to construct fluorescence energy transfer probes. A vast array of fluorophores useful in conjunction with the PLs are known to those of skill in the art. See, for example, Cardullo et al., *Proc. Natl. Acad. Sci. USA* 85: 8790–8794 (1988); Dexter, D. L., *J. of Chemical Physics* 21: 836–850 (1953); Hochstrasser et al., *Biophysical Chemistry* 45: 133–141 (1992); Selvin, P., *Methods in Enzymology* 246: 300–334 (1995); Steinberg, I. *Ann. Rev. Biochem.,* 40: 83–114 (1971); Stryer, L. *Ann. Rev. Biochem.,* 47: 819–846 (1978); Wang et al., *Tetrahedron Letters* 31: 6493–6496 (1990); Wang et al., *Anal. Chem.* 67: 1197–1203 (1995).

A non-limiting list of exemplary donors that can be used in conjunction with the quenchers of the invention is provided in Table 2.

TABLE 2

Suitable moieties that can be selected
as donors or acceptors in FET pairs 4-acetamido-4'-isothiocyanatostilbene-2,2'disulfonic acid
acridine and derivatives:

acridine
acridine isothiocyanate
5-(2'-aminoethyl)aminonaphthalene-1-sulfonic acid (EDANS)
4-amio-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin 7-amino-4-methylcoumarin (AMC, Coumarin 120)
7-amino-4-trifluoromethylcouluarin (Coumaran 151)
cyanine dyes
cyanosine
4',6-diaminidino-2-phenylindole (DAPI)
5',5"-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-dissulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:

eosin
eosin isothiocyanate
erythrosin and derivatives:

erythrosin B
erythrosin isothiocyanate
ethidium
fluorescein and derivatives:

5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:

pyrene
pyrene butyrate
succinimidyl 1-pyrene butyrate
quantum dots
Reactive Red 4 (Cibacron ™ Brilliant Red 3B-A)
rhodamine and derivatives:

6-carboxy-X-rhodamine (ROX)
6-carboxyrhodamine (R6G)
lissamine rhodamine B sulfonyl chloride rhodamine (Rhod)
rhodamine B
rhodamine 123
rhodamine X isothiocyanate sulforhodamine B
sulforhodamine 101

TABLE 2-continued

Suitable moieties that can be selected
as donors or acceptors in FET pairs sulfonyl chloride derivative of sulforhodamine 101 (Texas Red)
N,N,N',N'-tetramethyl-6-carboxyrhodamine (TAMRA)
tetramethyl rhodamine tetramethyl rhodamine isothiocyanate (TRITC)
riboflavin
rosolic acid
lanthanide chelate derivatives There is a great deal of practical guidance available in the literature for selecting appropriate donor-acceptor pairs for particular probes, as exemplified by the following references: Pesce et al., Eds., FLUORESCENCE SPECTOROSCOPY (Marcel Dekker, New York, 1971); White et al., FLUORESCENCE ANALYSIS: A Practical Approach (Marcel Dekker, New York, 1970); and the like. The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In a FET pair, it is generally preferred that an absorbance band of the acceptor substantially overlap a fluorescence emission band of the donor. When the donor (fluorophore) is a component of a probe that utilizes fluorescence resonance energy transfer (FRET), the donor fluorescent moiety and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of FRET between the donor-acceptor pair can also be adjusted by changing ability of the donor and acceptor to dimerize or closely associate. If the donor and acceptor moieties are known or determined to closely associate, an increase or decrease in association can be promoted by adjusting the length of a linker moiety, or of the probe itself, between the two fluorescent proteins. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is preferably covalently bound to the probe species. The ligand then binds to another molecules (e.g., streptavidin) molecule, which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidotases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Presently preferred fluorophores of use in conjunction with the complexes of the invention, include, for example, xanthene dyes, including fluoresceins, and rhodamine dyes. Many suitable forms of these compounds are widely available commercially with substituents on their phenyl moieties, which can be used as the site for bonding or as the bonding functionality for attachment to an nucleic acid. Another group of preferred fluorescent compounds are the naphthylamines, having an amino group in the alpha or beta position. Included among such napbthylamino compounds are 1-dimethylaminonaphthyl-5-sulfonate, 1-anilino-8-naphthalene sulfonate and 2-p-touidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

For clarity of illustration, the discussion below focuses on attaching the complexes of the invention and other fluorophores to nucleic acids. The focus on nucleic acid probes is not intended to limit the scope of probe molecules to which the complexes of the invention can be attached. Those of skill in the art will appreciate that the complexes of the invention can also be attached to small molecules (e.g., small molecular bioactive agents), proteins, peptides, synthetic polymers, solid supports and the like using standard synthetic chemistry or modifications thereof.

In an exemplary embodiment, in which the probe is a nucleic acid probe, the acceptor molecule is a rhodamine dye. The rhodamine moiety is preferably attached to either the 3'- or the 5'-terminus of the nucleic acid, although internal sites are also accessible for derivitization of PLs and have utility for selected purposes. Whichever terminus the rhodamine derivative is attached to, the complex of the invention will generally be attached to its antipode, or at a position internal to the nucleic acid chain. The rhodamine acceptor is preferably introduced using a commercially available amidite. Different donor groups of the invention are also preferably introduced using a reactive derivative (e.g., amidite) of the donor. Alternatively, donor groups comprising reactive groups (e.g., isothiocyanates, active esters, etc.) can be introduced via reaction with a reactive moiety on a tether or linker arm attached to the nucleic acid (e.g., hexylamine).

In yet another preferred embodiment, the donor moiety can be attached at the 3'-terminus of a nucleic acid by the use of a derivatized synthesis support. For example, a complexing agent of the invention is tethered to a solid support that is derivatized with an analogue of the complex. Such derivatized supports are well known in the art and are exemplified by a TAMRA (tetramethylrhodamine carboxylic acid) derivative that is attached to a nucleic acid 3'-terminus using a commercially available solid support that is derivatized with an analogue of the TAMRA fluorophore (Biosearch Technologies, Inc.)

In view of the well-developed body of literature concerning the conjugation of small molecules to nucleic acids, many other methods of attaching donor/acceptor pairs to nucleic acids will be apparent to those of skill in the art. For example, rhodamine and fluorescein dyes are conveniently attached to the 5'-hydroxyl of an nucleic acid at the conclusion of solid phase synthesis by way of dyes derivatized with a phosphoramidite moiety (see, for example, Woo et al., U.S. Pat. No. 5,231,191; and Hobbs, Jr., U.S. Pat. No. 4,997,928).

More specifically, there are many linking moieties and methodologies for attaching groups to the 5'- or 3'-termini of nucleic acids, as exemplified by the following references: Eckstein, editor, Nucleic Acids and Analogues: A Practical Approach (IRL Press, Oxford, 1991); Zuckerman et al., *Nucleic Acids Research*, 15: 5305–5321 (1987) (3'-thiol group on nucleic acid); Sharma et al., *Nucleic Acids Research*, 19: 3019 (1991) (3'-sulfhydryl); Giusti et al.,*PCR Methods and Applications*, 2: 223–227 (1993) and Fung et al., U.S. Pat. No. 4,757,141 (5'-pbosphoamino group via Aminolink TM II available group); Agrawal et al., *Tetrahedron Letters*, 31: 1543–1546 (1990) (attachment via phosphoramidate linkages); Sproat et al., *Nucleic Acids Research*, 15: 4837 (1987) (5-mercapto group); Nelson et al., *Nucleic Acids Research*, 17: 7187–7194 (1989) (3'-amino group), and the like.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Synthesis

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

The compounds of the invention can be prepared as a single stereoisomer or as a mixture of stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY $5^{th}$ ED., Longman Scientific and Technical Ltd., Essex, 1991, pp. 809–816; and Heller, *Acc. Chem. Res.* 23: 128 (1990).

An exemplary synthetic scheme leading to a bi-capped complexing agent of the invention is set forth in Scheme 1 (FIG. 1). An isophthalic acid derivative is activated at both carboxyl positions by contacting the acid with an activating group, such as 2-mercaptothiazoline under dehydrating conditions to produce compound 1. The activated carboxylic acid derivative 1 is tethered to a backbone, such as a polyamine by reacting an excess of 1 with the backbone component to produce compound 2. The ligand 2 is converted into a macrocyclic analogue 3 by reaction with another backbone (e.g., linker) molecule, which may be the same as or different than the backbone utilized to form 2.

Another exemplary synthetic route is set forth in Scheme 2 (FIG. 8). 2-Methoxyisophthaloyl thiazoline 1, is reacted with a polyamine ligand, such as tris(2-aminoethyl)amine ("TRENSAM") under conditions of high dilution to acylate each of the amines of the ligand, thereby forming compound 7. Compound 7 is susbsequently reacted with an amine, such as methyl amine to form ligand 8.

Figure 9:
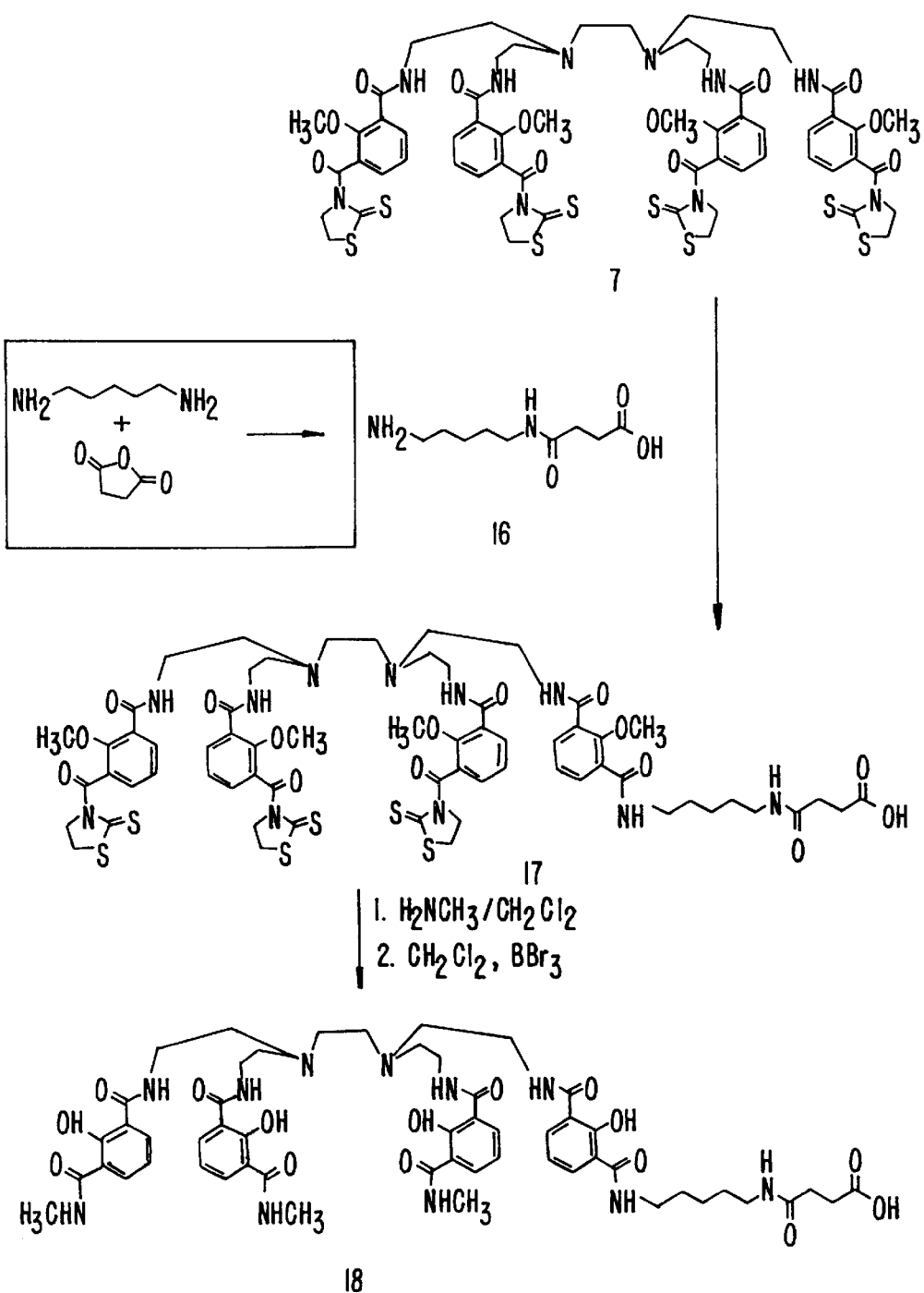
FIG. 9 is a representative synthetic scheme leading to an exemplary compound of the invention derivatized with a linker arm providing a locus for attaching the ligand to another species.

A further exemplary synthetic scheme is set forth in Scheme 3 (FIG. 9). Compound 7 (Scheme 2) is treated with a linker arm including both a reactive amine and a carboxylic acid group 16 to form compound 17. Compound 17 is converted into a complexing ligand by reaction with an amine, such as methyl amine to form compound 18.

Figure 10:
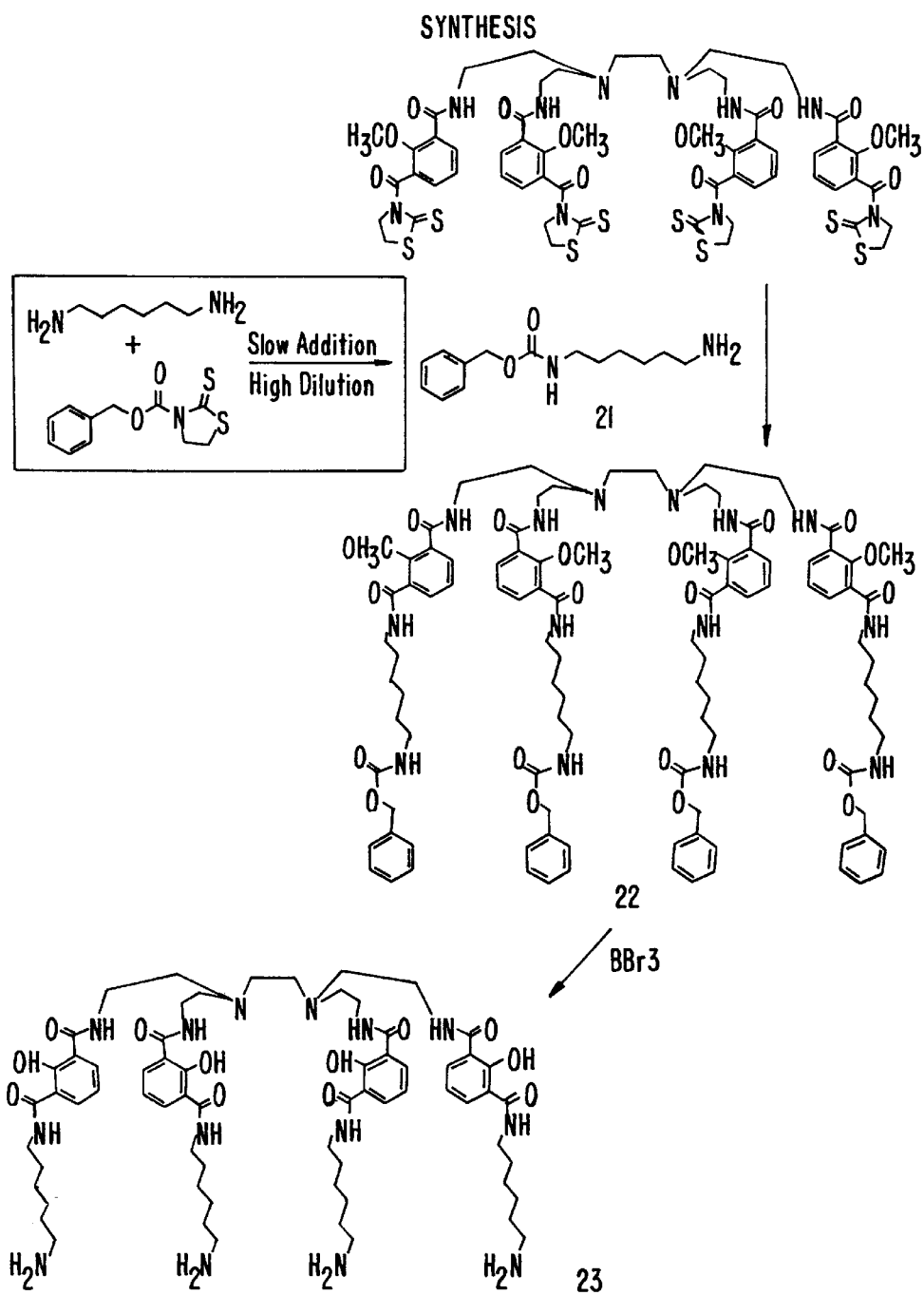
FIG. 10 is a representative synthetic scheme leading to exemplary compounds of the invention derivatized with alkyl amine groups.

Yet another exemplary synthetic scheme is set forth in Scheme 4 (FIG. 10). Compound 7 (Scheme 2) is treated with a mono-protected diamine 21, to form compound 23. An excess of the diamine is utilized to ensure that each of the available reactive groups is converted to the corresponding amide. It will be apparent to those of skill in the art that the degree of reactive group conversion can be controlled by altering conditions, such as the concentration of the reactants and the stoichiometry of compound 21 to compound 2.

Figure 11:
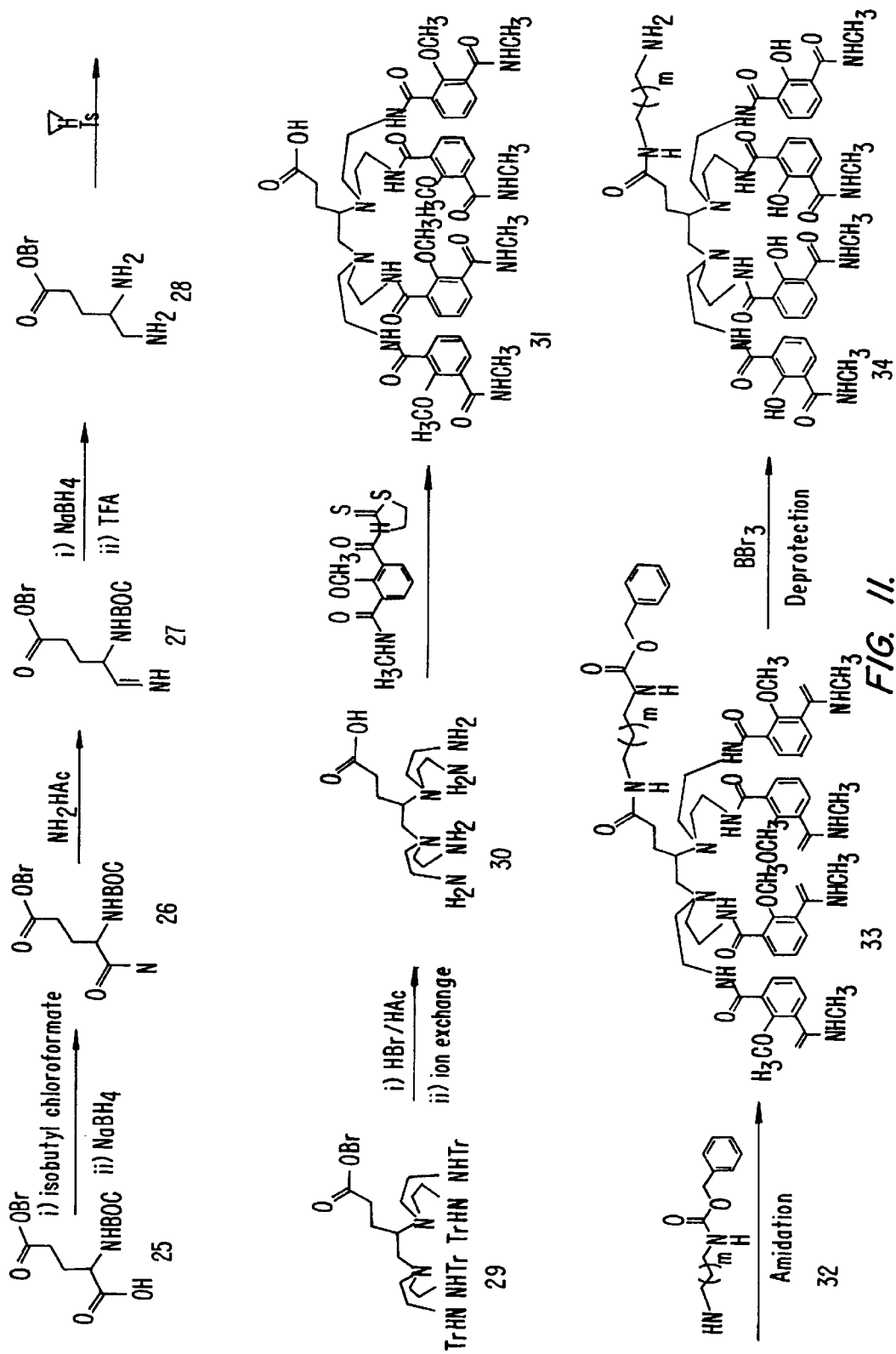
FIG. 11 is a representative synthetic scheme leading to exemplary compounds of the invention with backbones of varying length.
Figure 12:
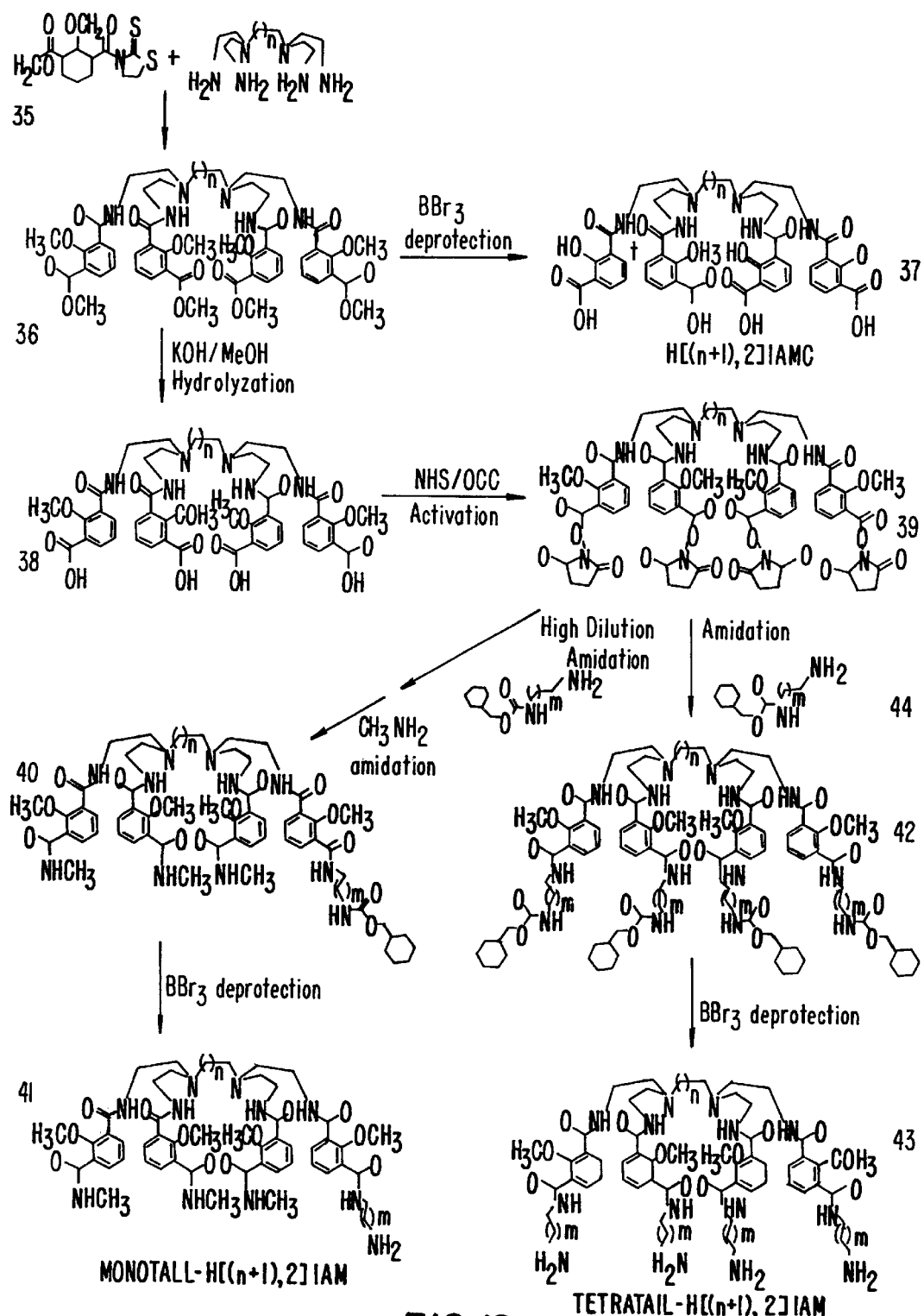
FIG. 12 is a representative synthetic scheme leading to an exemplary compound of the invention having a linker on the backbone providing a locus for attaching the compound to another molecule.

A linker arm can also be attached to the backbone of the chelating agent. For example, in Scheme 5 (FIG. 11), a chelator having an amine terminated linker arm integral to the backbone is prepared.

The above-recited synthetic schemes are intended to be exemplary of certain embodiments of the invention, those of skill in the art will recognize that many other synthetic strategies for producing the ligands of the invention are available without resort to undue experimentation.

The substituents on the isophthamidyl group and the on the backbone joining the isophthamidyl groups can themselves comprise chelating agents other than a hydroxyisophthamidyl group. Preferably, these chelators comprise a plurality of anionic groups such as carboxylate or phosphonate groups. In a preferred embodiment, these non-PL chelating agents are selected from compounds which themselves are capable of functioning as lanthanide chelators. In another preferred embodiment, the chelators are aminocarboylates (i.e. EDTA, DTPA, DOTA, NTA, HDTA, etc. and their phosphonate analogs such as DTPP, EDTP, HDTP, NTP, etc).

Many useful chelating groups, crown ethers, cryptands and the like are known in the art and can be incorporated into the compounds of the invention. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279–312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATIONS OF PROTEINS: FOOD, NUTRITIONAL, AND PHARMACOLOGICAL ASPECTS;" Feeney, et al., Eds., American Chemical Society, Washington, D.C., 1982, pp. 370–387; Kasina et al., *Bioconjugate Chem.*, 9: 108–117 (1998); Song et al., *Bioconjugate Chem.*, 8: 249–255 (1997).

In other embodiments substituents on the isophthalamidyl group or on the backbone are fluorescence sensitizers. Exemplary sensitizers include rhodamine 560, 575 and 590 fluoresceins, 2- or 4-quinolones, 2 or 4-coumarins, or derivatives thereof e.g. coumarin 445, 450, 490, 500 and 503, 4-trifluoromethylcoumarin (TFC), 7-diethyl-aminocumarin-3-carbohyddzide, etc., and especially carbostyril 124 (7-amino-4-methyl-2-quinolone), coumarin 120 (7-amino-4-methyl-2-coumarin), coumarin 124 (7-amino-4-(trifluoromethyl)-2-coumarin), aminomethyltrimethylpsoralen, napthalene and the like.

In a preferred embodiment, the sensitizer is a moiety that comprises a napthyl moiety.

After the PL is formed and purified, the fluorescent lanthanide complex is synthesized by any of a wide range of art-recognized methods, including, for example, by incubating a salt of the chelate with a lanthanide salt such as the lanthanide trihalide, triacetate, and the like.

The compounds of the invention, in their unconjugated form are useful as probes, indicators, separation media, and the like. Moreover, the compounds of the invention can be conjugated to a wide variety of compounds to create specific labels, probes, diagnostic and/or therapeutic reagents, etc. Examples of species to which the compounds of the invention can be conjugated include, for example, biomolecules such as proteins (e.g., antibodies, enzymes, receptors, etc.), nucleic acids (e g., RNA, DNA, etc.), bioactive molecules (e.g., drugs, toxins, etc.); solid subtrates such as glass or polymeric beads, sheets, fibers, membranes (e.g. nylon, nitrocellulose), slides (e.g. glass, quartz) and probes; etc.

In a preferred embodiment, the species to which the compound is conjugated is a biomolecule. Preferred biomolecules are those selected from the group consisting of antibodies, nucleic acids, enzymes, haptens, carbohydrates and antigens.

Assays and PL-Bearing Probes

In another preferred embodiment, the present invention provides a PL that is tethered to another molecule, such as a probe molecule and assays using these probes.

Assays

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

Assays based on specific binding reactions are used for detecting a wide variety of substances such as drugs, hormones, enzymes, proteins, antibodies, and infectious agents in various biological fluids and tissue samples. In general, the assays consist of an analyte, a recognition moiety for the analyte, and a detectable label. Competitive assay modalities generally utilize a binding partner in addition to these components. In an exemplary embodiment, the binding partner is a molecule that interacts with a recognition moiety to form a complex that is inherently less stable than a similar complex formed between the recognition moiety and the analyte, and is subsequently displaced by the incoming analyte.

Because the results of specific binding interactions are frequently not directly observable, a variety of fluorescent labels have been devised for determining the presence of an interaction. The fluorophores of the invention are detected by use of fluorescence spectroscopy or by the naked eye. An introduction to labels, labeling procedures and detection of labels, such as are useful in practicing the present invention, is found in Polak et al., INTRODUCTION TO IMMUNOCYCTOCHEMISTRY, $2^{nd}$ Ed., Springer Verlag, NY, (1977), and in Haugland, HANDBOOK OF FLUORESCENT PROBES AND Research CHEMICALS, a combined handbook and catalogue Published by Molecular Probes, Inc., Eugene, Oreg.(1996)

In certain embodiments, the assay is a competitive assay. In practice, the components of the assay (i.e., recognition moiety, binding partner and analyte) can have substantially any chemical structure, however in a preferred embodiment, the recognition moiety, the binding partner and the analyte are members independently selected from the group consisting of small molecular bioactive agents, biomolecules and combinations thereof. When a component of the assay is a biomolecule, the biomolecule is preferably a member selected from the group consisting of haptens, antibodies, antigens, carbohydrates, nucleic acids, peptides, enzymes and receptors.

In a competitive assay format, one or more than one of the components is labeled with a compound of the invention. For example, in one embodiment, the binding partner is labeled with a compound of the invention and its displacement from an immobilized recognition moiety is detected by the appearance of fluorescence in a liquid phase of the assay. In another competitive assay format, an immobilized enzyme is complexed with a substrate conjugated to a compound of the invention. The complex is then contacted with a putative antagonist. The displacement of fluorescence from the immobilized enzyme into a liquid phase of the assay is indicative of displacement of the substrate by the putative antagonist. These embodiments are offered by way of example only and it will be plain to one of skill in the art that many other competitive assay formats can utilize and benefit from the compounds of the invention.

In addition to ascertaining a binding event, it is frequently desired to quantitate the magnitude of the affinity between two or more binding partners. Thus, it is also within the scope of the present invention to utilize the compounds disclosed herein as a support for such assays.

Most typically, the amount of analyte present is measured by quantitating the amount of label fixed to a binding partner, analyte or recognition moiety following a binding event. Means of detecting and quantitating fluorescent labels are well known to those of skill in the art.

In another preferred embodiment, the affinity between two or more assay constituents is measured by quantifying a population selected from the group consisting of the analyte-recognition moiety complex, free analyte, free binding partner, binding partner-recognition moiety complex and combinations thereof.

The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. The binding assay can be performed, for example, in a 96-well filtration plate assembly (Millipore Corporation, Bedford, Mass.). One of the three binding partners (ie., the ligand, antagonist or receptor) is generally bound to the well or to a particulate material contained within the well.

Competition binding data can be analyzed by a number of techniques, including nonlinear least-squares curve fitting procedure. When the ligand is an antagonist for the receptor, this method provides the IC50 of the antagonist (concentration of the antagonist which inhibits specific binding of the ligand by 50% at equilibrium). The IC50 is related to the equilibrium dissociation constant (Ki) of the antagonist based on the Cheng and Prusoff equation: $Ki=IC50(1+L/Kd)$, where L is the concentration of the ligand used in the competitive binding assay, and Kd is the dissociation constant of the ligand as determined by Scatchard analysis. These assays are described, among other places, in Maddox el al., *J Exp Med.*, 158: 1211 (1983); Hampton et al., SEROLOGICAL METHODS , A LABORATORY MANUAL, APS Press, St. Paul, Minn., 1990.

The assays of the invention can be practiced with some or all components in solution. Alternatively, one or more components can be substantially insoluble in the assay medium. In a preferred embodiment, one or more members selected from the group consisting of the recognition moiety, the binding partner and the analyte are attached to a surface. Useful surface include, but are not limited to, glass or polymeric beads, sheets, fibers, membranes (e.g. nylon, nitrocellulose), slides (e.g. glass, quartz) and the like.

The assay can be performed in a large variety of ways. It is within the abilities of one of skill in the art to choose, for example, when to form the fluorescent complex by chelating the lanthanide, which assay component the chelate should be attached to and the like. In a preferred embodiment, the fluorescent complex is formed prior to displacing the binding partner from the binding partner-recognition moiety complex. In another preferred embodiment, the fluorescent complex is formed after displacing the binding partner from the binding partner-recognition moiety complex.

Following the displacement of the binding partner from the binding partner-recognition moiety complex, the remaining steps of the assay can be performed on the mixture that is formed by the displacement or one or more of the components of the mixture can be removed. In a preferred embodiment, the method further comprises separating the free binding partner from a member of the group consisting of the recognition-binding partner pair, the analyte-recognition moiety pair and combinations thereof.

In a preferred embodiment, the assays of the invention are immunological assays. Immlunological assays involve reactions between immunoglobulins (antibodies) which are capable of binding with specific antigenic determinants of various compounds and materials (antigens). Other types of reactions include binding between avidin and biotin, protein A and immunoglobulins, lectins and sugar moieties and the like. See, for example, U.S. Pat. No. 4,313,734, issued to Leuvering; U.S. Pat. No. 4,435,504, issued to Zuk; U.S. Pat. Nos. 4,452,901 and 4,960,691, issued to Gordon; and U.S. Pat. No. 3,893,808, issued to Campbell.

These assay techniques provide the ability to detect both the presence and amount of small quantities of analytes and are useful in, for example medical diagnostics and forensic applications. In the methods of the present invention, the analyte or its binding to the recognition moiety is generally detected by the use of a fluorescent label according to the invention.

Immunological assays are of three general types. In an exemplary competitive binding assays, labeled reagents and unlabeled analyte compounds compete for binding sites on a binding material. After an incubation period, unbound materials are washed off and the amount of labeled reagent bound to the site is compared to reference amounts for determination of the analyte concentration in the sample solution.

A second type of immunological assay is known as a sandwich assay and generally involves contacting an analyte sample solution to a surface comprising a first binding material immunologically specific for that analyte. A second solution comprising a binding material bearing a compound of the invention of the same type (antigen or antibody) as the first binding material is then added to the assay. The labeled binding material will bind to any analyte which is bound to the first binding material. The assay system is then subjected to a wash step to remove labeled binding material which failed to bind with the analyte and the amount of labeled material remaining is ordinarily proportional to the amount of bound analyte.

A third type of immunological assay technique involves agglutination reaction techniques and is exemplified by well-known assays for blood antigens and serum types. Immunological cross-reactivity between antibodies within serum and antigens presented on red blood cell surfaces is indicated by the formation of a three dimensional cross-linked network of red blood cells and antibodies. The agglutination of the serum/red blood cell mixture results in the formation of a pellet which can be visible to the naked eye, via the fluorescence of a compound of the invention attached to one or more components of the assay.

These assay procedures, enumerated above, were originally performed according to liquid phase immunochemistry techniques wherein enzymes and radiolabeled reactions were carried out in liquid solution in apparatus such as microtiter plates. More recently, techniques and procedures have been adapted for carrying out "solid" phase assays wherein enymatic and immunological reactions are carried out in solution on immobilizing substrates.

These types of assays, generally designated immunochromatographic immunoassays, can be developed in any number of formats employing principals of competitive, sandwich, or agglutination types of assays. They can also involve either flow across or flow along the immobilizing substrate. In general, the sandwich assays have the greatest utility for detection of large protein analytes or antibodies. The flow across type of assays have been used most extensively in sandwich type assays.

An exemplary immunochromatographic sandwich immunoassay procedure using the fluorescent agents of the invention employs a porous surface and an agent of the invention as a visual label attached to one member of a binding pair (e.g., antigen or antibody). The porous surface is generally a flat sheet and is usually comprised of either nylon, nitrocellulose, glass fiber, or the like. In a typical immnunochromatographic format a region or small area of the porous surface becomes a solid phase capturing surface by immobilizing a member of a binding pair directly onto the surface of a porous membrane or by indirectly attaching the member onto capture particles (i.e., latex, glass,) which are immobilized on the surface of a porous membrane. Direct immobilization of the binding pair to a porous membrane or capture particles occur through electrostatic interaction, (i.e., differences in ionic charge), hydrophobic interaction, or covalent binding. Where capture particles are used, the immobilization of capture particles to porous membranes can also occur through the same phenomena or through size exclusion preventing migration of the particles through the pores or fibers of the membrane. Many other types of assays can be run utilizing the compounds of the invention.

In a typical noncompetitive immunochromatographic assay, a test sample of a biological fluid such as blood, serum, plasma, saliva, urine, etc. must be in a sufficient volume and have a sufficient concentration of analyte to allow for sufficient interaction to occur between the analyte of interest, the labeled particles and the capturing solid phase. In order to increase the reaction kinetics, the concentration of particle labeled member of a binding pair and the concentration of binding pair at the surface of the porous membrane or capturing particles is optimized to produce as much specific binding as possible and at the same time minimize any nonspecific binding. The concentration of the particle labeled member must be of a concentration that does not produce prozone phenomena throughout the range of analyte concentrations that are of interest. Such concentration optimization is well within the abilities of one of skill.

Immunochromatographic assays can be in the form of strips or layers of the multilayered materials of the invention employing a hydrophobic support (e.g., Mylar, polystyrene. polypropylene, glass, etc.) wherein one or more compounds of the invention or moieties functionalized with a compound of the invention is either fixed directly or indirectly with a binder such as glue to the support. If it is desired, hydrophobic supports and housings can be employed to reduce evaporation of the fluid phase while the immunoreactants are being brought into contact with each other.

In an exemplary non-competitive assay in accordance with this aspect of the invention, an analyte is solubilized, deposited and bound onto the particulate material. The particulate material is then hydrated and sequentially exposed to primary antibodies and enzyme-conjugated secondary antibodies specific for the primary antibodies, with washing steps in between where appropriate. Enzyme levels are then determined by, for instance, substrate conversion protocols well known in the art, and the amount of primary antibodies can thus be measured by reference to a standard run in parallel.

Additionally, a binding domain of a receptor, for example, can serve as the focal point for a drug discovery assay, where, for example, the receptor is immobilized, and incubated both with agents (i.e., ligands) known to interact with the binding domain thereof, and a quantity of a particular drug or inhibitory agent under test. One of the incubation components is labeled with a compound of the invention. The extent to which the drug binds with the receptor and thereby inhibits receptor-ligand complex formation can then be measured. Such possibilities for drug discovery assays are contemplated herein and are considered within the scope of the present invention. Other focal points and appropriate assay formats will be apparent to those of skill in the art.

The compounds and methods of the invention can also be used to sequence nucleic acids and peptides. Fluorescent-labeled oligonucleotide primers have been used in place of radiolabeled primers for sensitive detection of DNA fragments (U.S. Pat. No. 4,855,225 to Smith et al.). Additionally, DNA sequencing products can be labeled with fluorescent dideoxynucleotides (U.S. Pat. No. 5,047,519 to Prober et al.) or by the direct incorporation of a fluorescent labeled deoxynucleotide (Voss et al. *Nucl. Acids Res.* 17:2517 (1989)). The compounds of the invention are useful in both of these formats. As currently practiced, fluorescent sequencing reactions circumvent many of the problems associated with the use of radionuclides.

As discussed above, the fluorescent complex can be formed at substantially any step of the assay. This is equally true in those embodiments, wherein one or more components of the assay mixture are removed following the displacement of the binding partner. In a preferred embodiment, the fluorescent complex is formed following the separation.

Compounds of the invention can be used to indicate the presence and amount of an enzyme in a mixture. For example, in certain embodiments, $Q^1$ is an enzymatically labile group and the presence of the labile group on the phenolic oxygen of the hydroxyisophthamidyl group will prevent the formation of a stable complex of a lanthanide ion. This situation is reversed, and a stable lanthanide complex is formed, when the hydroxyisophthamidyl chelate is contacted with an enzyme that is capable of cleaving the labile group, thus, freeing the phenolic oxygen anion. Similar to the embodiments discussed above, the assay mixture can be contacted with the enzyme at any time during the assay process. Additionally, if a component is separated from the reaction mixture (e.g., the liberated binding partner), the separated component and/or the remaining component can be contacted with the enzyme.

In a preferred embodiment, wherein $Q^1$ is an enzymatically labile group, the method further includes contacting a member selected from the group consisting of the binding partner-recognition moiety complex, the free binding partner and combinations thereof with an enzyme, thereby removing the enzymatically labile group.

An array of enzymatically removable groups is known in the art and it is within the abilities of one of skill in the art to select an appropriate enzymatically labile group for a particular application. In a preferred embodiment, the enzymatically labile group comprises a component of a member selected from the group consisting of phosphate, sulfate, acyl and glycoside groups. Enzymes capable of removing these groups include, for example, esterases, phosphatases, glycosidases and the like.

In another preferred embodiment, the removal of the enzymatically labile group and the subsequent formation of a fluorescent complex is used to detect the presence of an enzyme capable of removing the enzymatically labile group. See, for example, Drevin et al., U.S. Pat. No. 5,252,462, issued Oct. 12, 1993.

Although the compounds of the invention can be tethered to any component of the assay, they will most generally be attached to the binding partner. In this embodiment, the compounds of the invention can be attached to the binding partner through a reactive group on a phthalamidyl moiety, backbone or amide substitutent. Alternatively, they can be attached to the binding partner through a reactive group on the aromatic nucleus of one or more of the hydroxyisophthamidyl, moieties of the compounds. As discussed above, many suitable reactive groups are known to those of skill in the art and one of skill will be able to both choose and prepare a hydroxyisophthamidyl-chelate that is appropriately functionalized for a particular application.

It will generally be preferred that the linkage between the hydroxyisophthamidyl-chelates and the binding partner be stable under the conditions of the assay. Many stable linkages can be formed between the binding partner and the hydroxyisophthamidyl chelate including, for example, amides, amines, ethers, ureas, and the like. In a preferred embodiment, the linkage between the binding partner and a compound of the invention is a member selected from the group consisting of amide, thioamide, thoiurea and carbamate linkages. Suitable reactive groups and linkages are discussed in greater detail above.

In general, to determine the concentration of a target molecule, such as, for example, a nucleic acid, it is preferable to first obtain reference data in which constant amounts of probe and nucleic acid ligand are contacted with varying amounts of target. The fluorescence emission of each of the reference mixtures is used to derive a graph or table in which target concentration is compared to fluorescence emission. For example, a probe that: a) hybridizes to a target-free nucleic acid ligand; and b) has a stem-loop architecture with the 5' and 3' termini being the sites of fluorescent group and PL labeling, could be used to obtain such reference data. Such a probe gives a characteristic emission profile in which the fluorescence emission decreases as the target concentration increases in the presence of a constant amount of probe and nucleic acid ligand. Then, a test mixture with an unknown amount of target is contacted with the same amount of first nucleic acid ligand and second probe, and the fluorescence emission is determined. The value of the fluorescence emission is then compared with the reference data to obtain the concentration of the target in the test mixture.

Muliplex Analyses

Figure 20:
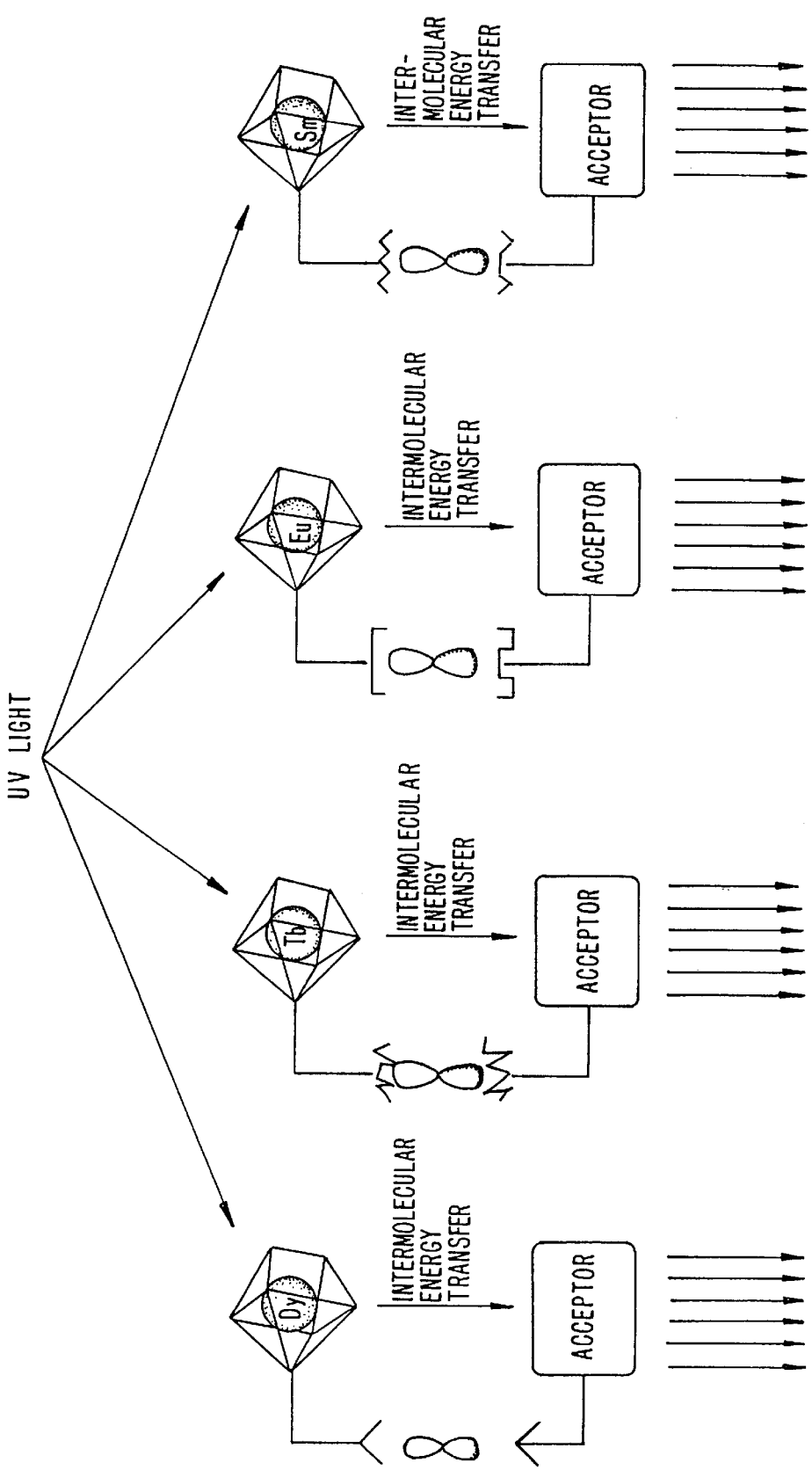
FIG. 20 is a schematic diagram of an exemplary multiplex assay of the invention.

In another preferred embodiment, the quenchers of the invention are utilized as a component of one or more probes used in an assay designed to detect multiple species in a mixture. An assays used to detect two or more species by using at least two probes bearing different fluorophores is referred to herein as a "multiplex analysis." A schematic diagram of such a multiplex analysis using a PL is set forth in FIG. 20.

Probes that include the compounds of the invention are also useful in performing multiplex-type analyses and assays. In a typical multiplex analysis, two or more distinct species (or regions of one or more species) are detected using two or more probes, wherein each of the probes is labeled with a different fluorophore. Preferred multiplex analyses relying on fluorescent energy transfer ideally meet several criteria. The fluorescent species should be bright and spectrally well-resolved and the energy transfer between the fluorescent species and the acceptor should be efficient.

Because of the ready availability of PLs of the invention having different emission characteristics, the compounds of the invention are particularly well suited for use in multiplex applications. Access to PLs having a range of absorbance characteristics allows for the design of FET probes in which the acceptor absorbance properties and the PL emission properties are matched, thereby providing a useful level of spectral overlap.

The simultaneous use of two or more probes using FET is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228–1229 (1998)). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. *Nature Biotechnology* 16: 49–53 (1998)) have described the simultaneous use of four differently labeled molecular beacons for allele discrimination, and Lee et al., *BioTechniques* 27: 342–349 (1999) have described seven color homogenous detection of six PCR products.

The PLs of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., Salmonella), nucleic acids (e.g., DNA, RNA, and analogues thereof), polysaccharides, lipopolysaccharides, lipids, fatty acids, non-biological polymers and small bioactive molecules (e.g., toxins, drugs, pesticides, metabolites, hormones, alkaloids, steroids).

Recognition Moieties

As used herein, the term "recognition moiety" refers to molecules that can interact with an analyte via either attractive or repulsive mechanisms. In a preferred embodiment, a recognition moiety is conjugated to a compound of the invention. In another exemplary embodiment, the analyte and the recognition moiety form an intimately associated pair by, for example, covalent bonding, ionic bonding, ion pairing, van der Waals association and the like. In another exemplary embodiment, the analyte and recognition moiety interact by a repulsive mechanism such as incompatible steric characteristics, charge-charge repulsion, hydrophilic-hydrophobic interactions and the like. It is understood that there is overlap between the generic terms "recognition moiety" and "analyte." In a particular application, a species may be an analyte, while in a different application, the species serves as a recognition moiety. In certain embodiments, the compounds of the invention serve as recognition moieties (e.g., when the analyte is a metal ion).

Recognition moieties can be selected from a wide range of small bioactive molecules (e.g., drugs, pesticides, toxins, etc.), organic functional groups (e.g., amines, carbonyls, carboxylates, etc.), biomolecules, metals, metal chelates and organometallic compounds.

When the recognition moiety is an amine, in preferred embodiments, the recognition moiety will interact with a structure on the analyte which reacts by interacting (e.g., binding, complexing) with the amine (e.g. carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by, for example, complexation (e.g., metal ions). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds which are being screened for their ability to interact with an analyte of choice. As such, drug moieties which are useful as recognition moieties in the instant invention include drugs from a broad range of drug classes having a variety of pharmacological activities.

Classes of useful agents include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine) ;diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, α-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or antithyroid agents (e.g. methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

The above enumerated, and other molecules, can be attached to the compounds of the invention, to solid substrates and the like by methods well-known to those of skill in the art. Ample guidance can be found in literature devoted to, for example, the fields of bioconjugate chemistry and drug delivery. For example, one of skill, faced with a drug comprising an available amine will be able to choose from among a variety of amine derivatizing reactions, locate an appropriately functionalized partner (e.g., a carboxylic acid terminated thiol) for the organic layer and react the partners under conditions chosen to effect the desired coupling (e.g., dehydrating agents, e.g., dicyclohexylcarbodiimide). See, for example, MODIFICATION OF PROTEINS: FOOD, NUTRITIONAL, AND PHARMACOLOGICAL ASPECTS, Feeney et al., Eds., American Chemical Society, Washington, D.C., 1982, pp. 370–387; POLYMERIC DRUGS AND DRUG DELIVERY SYSTEMS, Dunn et al., Eds., American Chemical Society, Washington, D.C., 1991.

When the recognition moiety is a chelating agent, crown ether or cyclodextrin, host-guest chemistry will dominate the interaction between the recognition moiety and the analyte. The use of host-guest chemistry allows a great degree of recognition moiety-analyte specificity to be engineered into a compound or assay of the invention. The use of these compounds to bind to specific compounds is well known to those of skill in the art. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279–312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARAMACOLOGICAL ASPECTS;" Feeney, et al., Eds., American Chemical Society, Washington, D.C., 1982, pp. 370–387; Kasina et al., *Bioconjugate Chem.*, 9: 108–117 (1998); Song et al., *Bioconjugate Chem.*, 8: 249–255 (1997).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity. See, for example, Szejtli, CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978.

Cyclodextrins are able to form inclusion complexes with an array of bioactive molecules including, for example, drugs, pesticides, herbicides and agents of war. See, Tenjarla et al., *J. Pharm. Sci.*, 87: 425–429 (1998); Zughul et al., *Pharm. Dev. Technol.*, 3: 43–53 (1998); and Albers et al., *Crit. Rev. Ther. Drug Carrier Syst.*, 12: 311–337 (1995). Importantly, cyclodextrins are able to discriminate between enantiomers of compounds in their inclusion complexes. Thus, in one preferred embodiment, the invention provides for the detection of a particular enantiomer in a mixture of enantiomers. See, Koppenhoefer et al., *J. Chromatogr., A* 793: 153–164 (1998).

The cyclodextrin or any other recognition moiety can be attached to a compound of the invention, solid support and the like either directly or through a spacer arm. See, Yamamoto et al., *J. Phys. Chem. B*, 101: 6855–6860 (1997). Methods to attach cyclodextrins to other molecules are well known to those of skill in the chromatographic and pharmaceutical arts. See, Sreenivasan, K. J., *Appl. Polym. Sci.*, 60: 2245–2249 (1996).

In another exemplary embodiment, the recognition moiety is a polyaminocarboxylate chelating agent, such as ethylenediaminetetraacetic acid (EDTA) or diethylenetriaminepentaacetic acid (DTPA). These recognition moieties can be attached, for example, to any amine-terminated component of a compound of the invention, solid support or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a compound of the invention, solid support or a crosslinking agent by any reactive peptide residue available on the surface of the protein. In preferred embodiments, the reactive groups are amines or carboxylates. In particularly preferred embodiments, the reactive groups are the ϵ-amine groups of lysine residues.

Recognition moieties which are antibodies can be used to recognize analytes which are proteins, peptides, nucleic acids, saccharides or small bioactive materials, such as drugs, herbicides, pesticides, industrial chemicals and agents of war. Methods of raising antibodies for specific molecules are well-known to those of skill in the art. See, U.S. Pat. No. 5,147,786, issued to Feng et al. on Sep. 15, 1992; U.S. Pat. No. 5,334,528, issued to Stanker et al. on Aug. 2, 1994; U.S. Pat. No. 5,686,237, issued to Al-Bayati, M. A. S. on Nov. 11, 1997; and U.S. Pat. No. 5,573,922, issued to Hoess et al. on Nov. 12, 1996. Methods for attaching antibodies agents to surfaces are also known in the art. See, Delamarche et al. *Langmuir,* 12: 1944–1946 (1996).

A recognition moiety can be conjugated to a compound of the invention by any of a large number of art-known attachment methods, as discussed above. In one embodiment, the recognition moiety is tethered directly to the hydroxyisophthamidyl chelate through a group on the aromatic hydroxyisophthamidyl nucleus, backbone or amide substituent. In another exemplary embodiment, a reactive bifunctional crosslinking agent is attached reactive group on a PL and this conjugate is subsequently bound to the recognition moiety via the reactive group on the crosslinking component and a group of complementary reactivity on the recognition moiety. Many useful crosslinking agents can be purchased commercially (Pierce Rockford, Ill.) or can be synthesized using techniques known in the art. Alternatively, the recognition moiety and cross-linking agent are coupled prior to attaching the hydroxyisophthamidyl chelate to the recognition moiety.

Analytes

The materials and methods of the present invention can be used to detect any analyte, or class of analytes, which interact with a recognition moiety in a detectable manner. The interaction between the analyte and recognition moiety can be any physicochemical interaction, including covalent bonding, ionic bonding, hydrogen bonding, van der Waals interactions, repulsive electronic interactions, attractive electronic interactions and hydrophobic/hydrophilic interactions.

In a preferred embodiment, the interaction is an ionic interaction. In this embodiment, an acid, base, metal ion or metal ion-binding ligand is the analyte. In a still further preferred embodiment, the interaction is a hydrogen bonding interaction. In particularly preferred embodiments, the hybridization of a nucleic acid to a nucleic acid having a complementary sequence is detected. In another preferred embodiment, the interaction is between an enzyme or receptor and a small molecule or peptide which binds thereto.

In another embodiment, the analyte competes for the recognition moiety with another agent which has been bound to the recognition moiety prior to introducing the analyte of interest. In this embodiment, it is the process or result of the analyte displacing the pre-bound agent which causes the detectable levels of fluorescence from the compound of the invention. Suitable combinations of recognition moieties and analytes will be apparent to those of skill in the art.

In presently preferred embodiments, the analyte is a member selected from the group consisting of acids, bases, organic ions, inorganic ions, pharmaceuticals, herbicides, pesticides and biomolecules. Each of these agents, where practicable, can be detected as a vapor or a liquid. These agents can be present as components in mixtures of structurally unrelated compounds, racemic mixtures of stereoisomers, non-racemic mixtures of stereoisomers, mixtures of diastereomers, mixtures of positional isomers or as pure compounds. Within the scope of the invention is a device and a method to detect a particular analyte of interest without interference from other substances within a mixture.

Organic ions which are substantially non-acidic and non-basic (e.g., quaternary alkylammonium salts) can be detected by a labeled recognition moiety of the invention. For example, a PL-labeled recognition moiety with ion exchange properties is useful in the present invention. A specific example is the exchange of a cation such as dodecyltrimethylammonium cation for a metal ion such as sodium. Recognition moieties that form inclusion complexes with organic ions are also of use. For example, crown ethers and cryptands can be used to form inclusion complexes with organic ions such as quaternary ammonium cations.

Inorganic ions such as metal ions and complex ions (e.g., $SO_4^{-2}$, $PO_4^{-3}$) can also be detected using the PLs and methods of the invention. Metal ions can be detected, for example, by their complexation or chelation by PLs or chelating agents bound to a compound of the invention. In this embodiment, the recognition moiety can be a simple monovalent moiety (e.g., carboxylate, amine, thiol) or can be a more structurally complex agent (e.g., ethylenediaminepentaacetic acid, crown ethers, aza crowns, thia crowns).

Complex inorganic ions can be detected by their ability to compete with PLs for bound metal ions in ligand-metal complexes. When a ligand bound to a PL forms a metal-complex having a thermodynamic stability constant which is less than that of the complex between the metal and the complex ion, the complex ion will cause the dissociation of the metal ion from the immobilized ligand. If the metal ion is the complexed lanthanide, the fluorescence will be decreased. Methods of determining stability constants for compounds formed between metal ions and ligands are well known to those of skill in the art. Using these stability constants, chelates that are specific for particular ions can be manufactured. See, Martell, A. E., Motekaitis, R. J., DETERMINATION AND USE OF STABILITY CONSTANTS, 2d Ed., VCH Publishers, New York 1992.

In a preferred embodiment, the affinity of an analyte for a particular metal ion is exploited by using a compound of the invention that includes that particular metal ion. The metal ion generally must have available at least one empty coordination site to which the analyte can bind. Alternatively, at least one bond between the metal and the metal-immobilizing agent must be sufficiently labile in the presence of the analyte to allow the displacement of at least one bond of the immobilizing reagent by the analyte. The interaction between the analyte and the metal ion can be detected using a number of art-recognized techniques, including, for example, UV/V is and fluorescence spectroscopy.

Other combinations of analytes and recognition moieties will be apparent to those of skill in the art.

Probes

The invention provides probes including PL moieties conjugated to, for example, a target species, a ligand for a target species (e.g., nucleic acid, peptide, etc.), a small molecule (e.g., drug, pesticide, etc.), and the like.

Nucleic Acid Probes

The PLs of the invention are useful in conjunction with nucleic-acid probes and they can be used as components of detection agents in a variety of DNA amplification/ quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the PL-derivatized nucleic acids can be used in probes of substantially any format, including, for example, format selected from molecular beacons, scorpion probes, sunrise probes, conformationally assisted probes, light up probes and TaqMan™ probes.

Thus in a further aspect, the present invention provides a method for detecting a nucleic acid target sequence. The method includes: (a) contacting the target sequence with a detector nucleic acid; (b) hybridizing the target binding sequence to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a fluorophore; and ii) a PL of the invention. Moreover, prior to its hybridization to a complementary sequence, the detector nucleic acid is preferably in a conformation that allows fluorescence energy transfer between the fluorophore and the PL when the fluorophore is excited. Furthermore, in each of the methods described in this section, a change in fluorescence is detected as an indication of the presence of the target sequence, and that change in fluorescence is preferably detected in-real time.

In another aspect, the invention provides a further method for detecting the presence of a nucleic acid target sequence. The method includes: (a) hybridizing to the target sequence a detector nucleic acid comprising a single-stranded target binding sequence and an intramolecularly associated secondary structure 5' to the target binding sequence, wherein at least a portion of the target sequence forms a single stranded tail which is available for hybridization to the target sequence; (b) in a primer extension reaction, synthesizing a complementary strand using the intramolecularly associated secondary structure as a template, thereby dissociating the intramolecularly associated secondary structure and producing a change in a fluorescence parameter; (c) detecting the change in the fluorescence parameter, thereby detecting the nucleic acid target sequence.

In this method, and unless otherwise noted, the other methods described in this section, the detector nucleic acid can assume substantially any intramolecularly associated secondary structure, but this structure is preferably a member selected from hairpins, stem-loop structures, pseudoknots, triple helices and conformationally assisted structures. Moreover, the intramolecularly base-paired secondary structure preferably comprises a portion of the target binding sequence. Moreover, the intramolecularly associated secondary structure preferably includes a totally or partially single-stranded endonuclease recognition site.

The complementary strand can be prepared by any art-recognized method for preparing such strands, but is preferably synthesized in a target amplification reaction, and more preferably by extension of the target sequence using the detector nucleic acid as a template.

In another aspect, the invention provides a method for detecting amplification of a target sequence. The method includes the use of an amplification reaction including the following steps: (a) hybridizing the target sequence and a detector nucleic acid. The detector nucleic acid includes a single-stranded target binding sequence and an intramolecularly associated secondary structure 5' to the target binding sequence. At least a portion of the target sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In yet a further aspect, the invention provides a method of ascertaining whether a first nucleic acid and a second nucleic acid hybridize. In this method, the first nucleic acid includes a PL according to the invention. The method includes: (a) contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

A probe bearing both a PL and a fluorophore can be used or, alternatively, one or more of the nucleic acids can be singly labeled with a PL or fluorophore. When a nucleic acid singly labeled with a PL is the probe, the interaction between the first and second nucleic acids can be detected by observing the quenching of the native nucleic acid fluorescence or, more preferably, the quenching of the fluorescence of a fluorophore attached to the second nucleic acid.

In addition to their general utility in species designed to probe nucleic acid amplification, detection and quantification, the present PLs can be used in substantially any nucleic acid probe format now known or later discovered. For example, the PLs of the invention can be incorporated into probe motifs, such as Taqman probes (Held et al., *Genome Res.* 6: 986–994 (1996), Holland et al., *Proc. Nat. Acad. Sci. USA* 88: 7276–7280 (1991), Lee et al., *Nucleic Acids Res.* 21: 3761–3766 (1993)), molecular beacons (Tyagi et al., *Nature Biotechnology* 14:303–308 (1996), Jayasena et al., U.S. Pat. No. 5,989,823, issued Nov. 23, 1999)) scorpion probes (Whitcomb et al., *Nature Biotechnology* 17: 804–807 (1999)), sunrise probes (Nazarenko et al., *Nucleic Acids Res.* 25: 2516–2521 (1997)), conformationally assisted probes (Cook, R., copending and commonly assigned U.S. Provisional Application 60/138,376, filed Jun. 9, 1999), peptide nucleic acid (PNA)-based light up probes (Kubista et al., WO 97/45539, December 1997), double-strand specific DNA dyes (Higuchi et al, *BioTechnology* 10: 413–417 (1992), Wittwer et al, *BioTechniques* 22: 130–138 (1997)) and the like. These and other probe motifs with which the present PLs can be used are reviewed in NONISOTOPIC DNA PROBE TECHNIQUES, Academic Press, Inc. 1992.

The nucleic acids for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor molecule to the terminal 3'-position of the nucleic acid probe by a linking moiety.

The nucleic acid can comprise DNA, RNA or chimeric mixtures or derivatives or modified versions thereof. Both the probe and target nucleic acid can be present as a single strand, duplex, triplex, etc. In addition to being labeled with an molecular energy transfer donor and a molecular energy transfer acceptor moiety, the nucleic acid can be modified at the base moiety, sugar moiety, or phosphate backbone with other groups such as radioactive labels, minor groove binders, intercalating agents an the like.

For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

In another embodiment, the nucleic acid comprises at least one modified sugar moiety selected from the group including, but not limited to, arabinose, 2-fluoroarabinose, xylulose, and hexose.

In yet another embodiment, the nucleic acid comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

Phosphodiester linked nucleic acids of the invention can be synthesized by standard methods known in the art, e.g. by use of an automated DNA synthesizer (such as are commercially available from P.E. Biosystems, etc.) using commercially available amidite chemistries. Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448–7451 (1988)). Other methods of synthesizing both phosphodiester- and modified phosphodiester-linked nucleic acids will be apparent to those of skill in the art.

Nucleic acid probes of the invention can be synthesized by a number of approaches, e.g., Ozaki et al., *Nucleic Acids Research,* 20: 5205–5214 (1992); Agrawal et al., *Nucleic Acids Research,* 18: 5419–5423 (1990); or the like. The nucleic acid probes of the invention are conveniently synthesized on an automated DNA synthesizer, e.g. a P.E. Biosystems, Inc. (Foster City, Calif.) model 392 or 394 DNA/RNA Synthesizer, using standard chemistries, such as phosphoramidite chemistry (see, for example, disclosed in the following references: Beaucage et al., *Tetrahedron,* 48: 2223–2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679. Alternative chemistries resulting in non-natural backbone groups, such as phosphorothioate, phosphoramidate, and the like, can also be employed.

When the nucleic acids are synthesized utilizing an automated nucleic acid synthesizer, the stabilizing moiety, energy transfer donor and energy transfer acceptor moieties are preferably introduced during automated synthesis. Alternatively, one or more of these moieties can be introduced either before or after the automated synthesis procedure has commenced. In another exemplary embodiment, one or more of these moieties is introduced after the automated synthesis is complete.

The donor moiety is preferably separated from the PL by at least about 10 nucleotides, and more preferably by at least about 15 nucleotides. The donor moiety is preferably attached to either the 3'- or 5'-terminal nucleotides of the probe. The PL moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine:water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Peptide Probes

Peptides, proteins and peptide nucleic acids that are labeled with a fluorophore and a PL of the invention can be used in both in vivo and in vitro enzymatic assays.

Thus, in another aspect, the present invention provides a method for determining whether a sample contains an enzyme. The method comprises: (a) contacting the sample with a peptide construct; (b) exciting the fluorophore; and (c) determining a fluorescence property of the sample, wherein the presence of the enzyme in the sample results in a change in the fluorescence property.

Peptide constructs useful in practicing the invention include those with the following features: i) a fluorophore; ii) a PL of the invention; and iii) a cleavage recognition site for the enzyme. Moreover, the peptide construct is preferably of a length and orientation and in a conformation allowing fluorescence energy transfer between the fluorophore and the PL when the fluorophore is excited.

When the probe is used to detect an enzyme, such as a degradative enzyme (e.g., protease), and a degree of fluorescence resonance energy transfer that is lower than an expected amount is observed, this is generally indicative of the presence of an enzyme. The degree of fluorescence resonance energy transfer in the sample can be determined, for example, as a function of the amount of fluorescence from the donor moiety, the amount of fluorescence from the acceptor moiety, the ratio of the amount of fluorescence from the donor moiety to the amount of fluorescence from the acceptor moiety or the excitation state lifetime of the donor moiety.

The assay also is useful for determining the amount of enzyme in a sample by determining the degree of fluorescence resonance energy transfer at a first and second time after contact between the enzyme and the tandem construct, and determining the difference in the degree of fluorescence resonance energy transfer. The difference in the degree of fluorescence resonance energy transfer reflects the amount of enzyme in the sample.

The assay methods also can also be used to determine whether a compound alters the activity of an enzyme, ie, screening assays. Thus, in a further aspect, the invention provides methods of determining the amount of activity of an enzyme in a sample from an organism. The method includes: (a) contacting a sample comprising the enzyme and the compound with a peptide construct comprising (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of fluorescence resonance energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that affect the activity of proteases are natural subjects of combinatorial chemistry. Screening compounds produced by combinatorial chemistry requires convenient enzymatic assays.

The most convenient assays for proteases are based on fluorescence resonance energy transfer from a donor fluorophore to an acceptor placed at opposite ends of a short peptide chain containing the potential cleavage site (see, Knight C. G., *Methods in Enzymol.* 248:18–34 (1995)). Proteolysis separates the fluorophore and acceptor, resulting in increased intensity in the emission of the donor fluorophore. Existing protease assays use short peptide substrates incorporating unnatural chromophoric amino acids, assembled by solid phase peptide synthesis.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent PL-bearing probes, wherein the fluorophore and the PL are linked by a randomized peptide linker moiety can be generated using recombinant engineering techniques or synthetic chemistry techniques. Screening the members of the library can be accomplished by measuring a signal related to cleavage, such as fluorescence energy transfer, after contacting the cleavage enzyme with each of the library members of the tandem fluorescent peptide construct. A degree of fluorescence resonance energy transfer that is lower than an expected amount indicates the presence of a linker sequence that is cleaved by the enzyme. The degree of fluorescence resonance energy transfer in the sample can be determined, for example, as a function of the amount of fluorescence from the donor moiety, the amount of fluorescence from the acceptor donor moiety, or the ratio of the amount of fluorescence from the donor moiety to the amount of fluorescence from the acceptor moiety or the excitation state lifetime of the donor moiety.

In the tandem constructs of the invention, the donor and acceptor moieties are connected through a linker moiety. The linker moiety, preferably, includes a peptide moiety, but can be another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the fluorophore and the PL of the invention. The separation is measurable as a change in FRET.

When the cleavage agent of interest is a protease, the linker can comprise a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMERS'S DISEASE, ed. Masters et al. pp. 190–198(1994).

Solid Support Immobilized PL Analogues

The PLs of the invention can be immobilized on substantially any polymer, biomolecule, and solid or semni-solid material having any useful configuration. Moreover, any conjugate comprising one or more PLs can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a PL of the invention or a species including a PL of the invention. For clarity of illustration, the following discussion focuses on attaching a reactive PL to a solid support. The following discussion is also broadly relevant to attaching a species that includes within its structure a reactive PL to a solid support, and the attachment of such species and reactive PL analogues to other molecules and structures.

The PLs are preferably attached to a solid support by forming a bond between a reactive group on the PL and a reactive group on the surface of the solid support or a linker attached to the solid support, thereby derivatizing the solid support with one or more PL analogues. The bond between the solid support and the PL is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxy-benzyl alcohol resin, arminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Moreover, for applications in which an appropriate solid support is not commercially available, a wide variety of reaction types are available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a PL of complementary reactivity, such as a PL active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene.

When the support is constructed of a siliceous material such as glass, the surface can be derivatized by reacting the surface Si—OH, SiO—H, and/or Si—Si groups with a functionalizing reagent.

In a preferred embodiment, wherein the substrates are made from glass, the covalent bonding of the reactive group to the glass surface is achieved by conversion of groups on the substrate's surface by a silicon-modifying reagent such as:

$$(R^aO)_3\text{—Si—}R^b\text{—}X^a \qquad (2)$$

where $R^a$ is an alkyl group, such as methyl or ethyl, $R^b$ is a linking group between silicon and $X^a$, and $X^2$ is a reactive group or a protected reactive group. Silane derivatives having halogens or other leaving groups beside the displayed alkoxy groups are also useful in the present invention.

In another preferred embodiment, the reagent used to functionalize the solid support provides for more than one reactive group per each reagent molecule. Using reagents, such as the compound below, each reactive site on the substrate surface is, in essence, "amplified" to two or more functional groups:

$$(R^2O)_3\text{—Si—}R^b\text{—}(X^a)_n \qquad (3)$$

where $R^a$ is an alkyl group (e.g.,methyl, ethyl), $R^b$ is a linking group between silicon and $X^a$, $X^a$ is a reactive group or a protected reactive group and n is an integer between 2 and 50, and more preferably between 2 and 20. The amplification of a PL by its attachment to a silicon-containing substrate is intended to be exemplary of the general concept of PL amplification. This amplification strategy is equally applicable to other aspects of the invention in which a PL analogue is attached to another molecule or solid support.

A number of siloxane functionalizing reagents can be used, for example:

1. Hydroxyalkyl siloxanes (Silylate surface, functionalize with diborane, and $H_2O_2$ to oxidize to the alcohol)
   a. allyl trichlorosilane→→3-hydroxypropyl
   b. 7-oct-1-enyl trichlorchlorosilane→→8-hydroxyoctyl
2. Diol (dihydroxyalkyl) siloxanes (silylate surface and hydrolyze to diol)
   a. (glycidyl trimethoxysilane→→(2,3-dihydroxypropyloxy)propyl
3. Aminoalkyl siloxanes (amines requiring no intermediate functionalizing step)
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine.

It will be apparent to those of skill in the art that an array of similarly useful functionalizing chemistries is available when support components other than siloxanes are used. Thus, for example alkyl thiols, functionalized as discussed above in the context of siloxane-modifying reagents, can be attached to metal films and subsequently reacted with a PL to produce the immobilized compound of the invention.

R groups of use for $R^b$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups and combinations thereof.

Nucleic Acid Capture Probes

In one embodiment, an immobilized nucleic acid comprising a PL is used as a capture probe. The nucleic acid probe can be attached directly to a solid support, for example by attachment of the 3'- or 5'-terminal nucleotide of the probe to the solid support. More preferably, however, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length.

In yet another preferred embodiment, the solid support is also used as the synthesis support in preparing the probe. The length and chemical stability of the linker between the solid support and the first 3'-unit of nucleic acid play an important role in efficient synthesis and hybridization of support bound nucleic acids. The linker arm should be sufficiently long so that a high yield (>97%) can be achieved during automated synthesis. The required length of the linker will depend on the particular solid support used. For example, a six atom linker is generally sufficient to achieve a >97% yield during automated synthesis of nucleic acids when high cross-linked polystyrene is used as the solid support. The linker arm is preferably at least 20 atoms long in order to attain a high yield (>97%) during automated synthesis when CPG is used as the solid support.

Hybridization of a probe immobilized on a solid support generally requires that the probe be separated from the solid support by at least 30 atoms, more preferably at least 50 atoms. In order to achieve this separation, the linker generally includes a spacer positioned between the liner and the 3'-terminus. For nucleic acid synthesis, the linker arm is usually attached to the 3'-OH of the 3'-terminus by an ester linkage which can be cleaved with basic reagents to free the nucleic acid from the solid support.

A wide variety of linkers are known in the art, which may be used to attach the nucleic acid probe to the solid support. The linker may be formed of any compound, which does not significantly interfere with the hybridization of the target sequence to the probe attached to the solid support. The linker may be formed of, for example, a homopolymeric nucleic acid, which can be readily added on to the linker by automated synthesis. Alternatively, polymers such as functionalized polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkages between the solid support, the linker and the probe are preferably not cleaved during synthesis or removal of base protecting groups under basic conditions at high temperature. These linkages can, however, be selected from groups that are cleavable under a variety of conditions. Examples of presently preferred linkages include carbamate, ester and amide linkages.

Acrylamide-Immobilized Probes

In another preferred embodiment, a species is within a matrix, such as an acrylamide matrix and the species bears a PL, or the presence of the immobilized species is ascertained using a probe bearing a PL. In a preferred embodiment, the immobilization is accomplished in conjunction with the "acrydite" process invented and commercialized by Mosaic Technologies (Cambridge, Mass., see, Rehman et al., *Nucleic Acids Research,* 27: 649–655 (1999)). The acrydite method allows immobilization of alkene labeled capture probes within a polymerized polyacrylamide network. When target mixes are run past the immobilized probe band under electrophoresis conditions, the target nucleic acid is captured substantially quantitatively. However, detection of this event currently requires a second probe. In one embodiment, probes bearing a PL, and/or a fluorphore, are immobilized in an acrylamide matrix and subsequently contacted with the target mix. By using fluorescent probes as capture probes, signals from target mixes can be directly detected in real time.

Microarrays

The invention also provides microarrays including immobilized PLs and compounds functionalized with PLs. Moreover, the invention provides methods of interrogating microarrays using probes that are functionalized with PLs. The immobilized species and the probes are selected from substantially any type of molecule, including, but not limited to, small molecules, peptides, enzymes nucleic acids and the like.

Nucleic acid microairays consisting of a multitude of immobilized nucleic acids are revolutionary tools for the generation of genomic information, see, Debouck et al., in supplement to *Nature Genetics,* 21:48–50 (1999). The discussion that follows focuses on the use of PLs in conjunction with nucleic acid microarrays. This focus is intended to be illustrative and does not limit the scope of materials with which this aspect of the present invention can be practiced.

Thus, in another preferred embodiment, the compounds of the present invention are utilized in a microarray format. The PLs, or species bearing PLs can themselves be components of a microarray or, alternatively they can be utilized as a tool to screen components of a microarray.

Thus, in a preferred embodiment, the present invention provides a method of screening a microarray. The method includes contacting the members of the microarray with a PL-bearing probe and interrogating the microarray for regions of fluorescence. The fluorescent regions are indicative of the presence of an interaction between the PL-bearing probe and a microarray component. In another version of this method, the microarray is interrogated for regions in which fluorescence is quenched, again indicating the presence of an interaction between the PL-bearing probe and a component of the microarray.

In another preferred embodiment, the array comprises immobilized PL-bearing FET probes as the interrogating species. In this embodiment, the probe "turns on" when hybridized to its target. Such arrays are easily prepared and read, and can be designed to give quantitative data. Arrays comprising PL-bearing probes are valuable tools for expression analysis and clinical genomic screening.

In another preferred embodiment, the immobilized PL-bearing probe is not a FET probe. A microarray based on such as format can be used to probe for the presence of interactions between an analyte and the immobilized probe by, for example, observing the quenching of analyte fluorescence upon interaction between the probe and analyte.

In a further preferred embodiment, the microarrays comprise n probes that comprise identical or different nucleic acid sequences. Alternatively, the microarray can comprise a mixture of n probes comprising groups of identical and different nucleic acid sequences identical nucleic acid sequences). In a preferred embodiment, n is a number from 2 to 100, more preferably, from 10 to 1,000, and more preferably from 100 to 10,000. In a still further preferred embodiment, the n probes are patterned on a substrate as n distinct locations in a manner that allows the identity of each of the n locations to be ascertained.

In yet another preferred embodiment, the invention also provides a method for preparing a microarray of n PL-bearing probes. The method includes attaching PL-bearing probes to selected regions of a substrate. A variety of methods are currently available for making arrays of biological macromolecules, such as arrays nucleic acid molecules. The following discussion focuses on the assembly of a microatray of PL-bearing probes, this focus is for reasons of brevity and is intended to be illustrative and not limiting.

One method for making ordered arrays of PL-bearing probes on a substrate is a "dot blot" approach. In this method, a vacuum manifold transfers a plurality, e.g., 96, aqueous samples of probes from 3 millimeter diameter wells to a substrate. The probe is immobilized on the porous membrane by baking the membrane or exposing it to UV radiation. A common variant of this procedure is a "slot-blot" method in which the wells have highly-elongated oval shapes.

Another technique employed for making ordered arrays of probes uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39–81 (1990).

An alternate method of creating ordered arrays of probes is analogous to that described by Pirrung et al. (U.S. Pat. No. 5,143,854, issued 1992), and also by Fodor et al., (*Science*, 251: 767–773 (1991)). This method involves synthesizing different probes at different discrete regions of a particle or other substrate. This method is preferably used with relatively short probe molecules, e.g., less than 20 bases. A related method has been described by Southern et al. (*Genomics*, 13: 1008–1017 (1992)).

Khrapko, et al., *DNA Sequence*, 1: 375–388 (1991) describes a method of making an nucleic acid matrix by spotting DNA onto a thin layer of polyacrylamide. The spotting is done manually with a micropipette.

The substrate can also be patterned using techniques such as photolithography (Kleinfield et al., *J. Neurosci.* 8:4098–120 (1998)), photoetching, chemical etching and microcontact printing (Kumar et al., *Langmuir* 10:1498–511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y., *J. Am. Chem. Soc.* 117:3274–75 (1995). Similarly, using photolithography, patterns with features as small as 1 µm are produced. See, Hickman et al., *J. Vac. Sci. Technol.* 12:607–16 (1994). Patterns which are useful in the present invention include those which include features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the probes. In general, each of these substrate features is isolated from the other wells by a raised wall or partition and the wells do not fluidically communicate. Thus, a particle, or other substance, placed in a particular well remains substantially confined to that well. In another preferred embodiment, the patterning allows the creation of channels through the device whereby an analyte or other substance can enter and/or exit the device.

In another embodiment, the probes are immobilized by "printing" them directly onto a substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art. See, for example, Kleinfield et al., *J. Neurosci.* 8:4098–120 (1998). Following removal of the photoresist, a second CAP, having a structure different from the first probe can be bonded to the substrate on those areas initially covered by the resist. Using this technique, substrates with patterns of probes having different characteristics can be produced. Similar substrate configurations are accessible through microprinting a layer with the desired characteristics directly onto the substrate. See, Mrkish et al. *Ann. Rev. Biophys. Biomol. Struct.* 25:55–78 (1996).

Spacer Groups

As used herein, the term "spacer group," refers to constituents of PL-bearing probes. The spacer group links donor and/or acceptor moieties and other groups to the nucleic acid, peptide or other polymeric component of the probe. The spacer groups can be hydrophilic (e.g., tetraethylene glycol, hexaethylene glycol, polyethylene glycol) or they can be hydrophobic (e.g., hexane, decane, etc.).

In a preferred embodiment, the immobilized construct includes a spacer between the solid support reactive group and the PL analogue. The linker is preferably selected from $C_6$–$C_{30}$ alkyl groups, $C_6$–$C_{30}$ substituted alkyl groups, polyols, polyethers (e.g., poly(ethyleneglycol)), polyamines, polyamino acids, polysaccharides and combinations thereof.

In certain embodiments, it is advantageous to have a moiety of the probe attached to the polymeric component by a group that provides flexibility and distance from the polymeric component. Using such spacer groups, the properties of the moiety adjacent to the polymeric component is modulated. Properties that are usefully controlled include, for example, hydrophobicity, hydrophilicity, surface-activity, the distance of the donor and/or PL moiety from the nucleic acid and the distance of the donor from the PL.

In an exemplary embodiment, the spacer serves to distance the PL from a nucleic acid. Spacers with this characteristic have several uses. For example, a PL held too closely to the nucleic acid may not interact with the donor group, or it may interact with too low of an affinity. When a PL is itself sterically demanding, the interaction leading to quenching can be undesirably weakened, or it may not occur at all, due to a sterically-induced hindering of the approach of the two components.

When the construct comprising the PL is immobilized by attachment to, for example, a solid support, the construct can also include a spacer moiety between the reactive group of the solid support and the PL analogue, or other probe component bound to the solid support.

In yet a further embodiment, a spacer group used in the probes of the invention is provided with a group that can be cleaved to release a bound moiety, such as a PL, fluorophore, minor groove binder, intercalating moiety, and the like from the polymeric component. Many cleaveable groups are known in the art. See, for example, Jung et al., *Biochem. Biophys. Acta*, 761: 152–162 (1983); Joshi et al., *J. Biol. Chem.*, 265: 14518–14525 (1990); Zarling et al., *J. Immunol.*, 124: 913–920 (1980); Bouizar et al., *Eur. J. Biochem.*, 155: 141–147 (1986); Park et al., *J. Biol. Chem.*, 261: 205–210 (1986); Browning et al., *J. Immunol.*, 143: 1859–1867 (1989). Moreover a broad range of cleavable, bifunctional (both homo- and hetero-bifunctional) spacer arms are commercially available from suppliers such as Pierce.

An exemplary embodiment utilizing spacer groups is set forth in Formulae VII and VIII, above. In these formulae, $R^b$ is either stable or it can be cleaved by chemical or photochemical reactions. For example, $R^b$ groups comprising ester or disulfide bonds can be cleaved by hydrolysis and reduction, respectively. Also within the scope of the present invention is the use of $R^b$ groups which are cleaved by light such as, for example, nitrobenzyl derivatives, phenacyl groups, benzoin esters, etc. Other such cleaveable groups are well-known to those of skill in the art.

Kits

In another aspect, the present invention provides kits containing one or more of the PLs or PL-bearing compositions of the invention. In one embodiment, a kit will include a reactive PL derivative and directions for attaching this derivative to another molecule. In another embodiment, the kit include a PL-labeled nucleic acid that optionally is also labeled with a second fluorophore or quencher and directions for using this nucleic acid in one or more assay formats. Other formats for kits will be apparent to those of skill in the art and are within the scope of the present invention.

The invention provides kits for practicing the methods noted above. The kits can include any of the compositions noted above, and optionally further include additional components such as instructions to practice the methods, one or more containers or compartments (e.g., to hold the assay components, nucleic acids, antibodies, inhibitors or the like), a robotic armature for mixing kit components or the like.

The invention also provides integrated systems for performing the methods disclosed herein. For example, in the performing assays, in one embodiment, the delivery of individual compounds or compound components is accomplished by means of a robotic armature which transfers fluid from a source to a destination, a controller which controls the robotic armature, a label detector, a data storage unit which records label detection, and an assay component such as a microtiter dish comprising a well. When a labeled compound is used, it is detected by means of the label detector.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous ligation reactions.

Optical Amplification

Optical signals are important for transmitting information. However, when an optical signal is transmitted through an optical fiber, attenuation will always occur to a certain extent, such that it is necessary to amplify the signal after a certain distance (typically in the order of about 50–100 km). Conventionally, for that purpose an electronic amplifier is used. At the amplifier station, the optical signal must then be converted into an electrical signal, which is amplified in an electronic amplifer, after which the amplified electrical signal is converted back into an optical signal. This involves not only the disadvantage that an amplifier station has a rather complicated structure with rather a large number of parts, among which optical/electrical converters and electrical/optical converters, but this also implies that the bandwidth and bit-rate of the overall system is limited by the electronic components. Therefore, optical fiber amplifiers have recently been developed, i.e. amplifiers which amplify the optical signal directly and do not need a conversion into an electrical signal. Such devices are disclosed in, for example, Yan et al., U.S. Pat. No. 5,982,973, issued Nov. 9, 1999; Kleinerman, U.S. Pat. No. 5,928,222, issued Jul. 27, 1999; Desurvire, *Physics Today*, January 1994, 20–27; Sloof et al., *J. Appl. Phys.* 83: 497 (1998).

Thus, in another embodiment, the present invention provides a substrate for the transmission and amplification of light, said substrate comprising a compound of the invention. The compound of the invention can be incorporated into the substrate in any manner known in the art, including, but not limited to, covalent attachment, coating, doping, and the like.

The substrate can include any material useful for a particular application, including, but not limited to, glass, organic polymers, inorganic polymers and combinations thereof.

Also provided is a method for amplifying light transmitted by the substrate derivatized with a compound of the invention, as described above. The method comprises transmitting light through such a substrate, thereby amplifying the light.

The substrates and methods of the invention can be used in fiber optic devices, sensors (see, for example, Kopelman et al., U.S. Pat. No. 5,627,922; and Pinkel et al., U.S. Pat. No. 5,690,894), fiber optic "refrigerators" and the like.

Medical Applications

The compounds of the invention can also be used to treat malignant tumors via photodynamic therapy (PDT). Additionally, the complexes of the invention be used in vivo and in vitro as chelating agents for: (1) certain paramagnetic metal ions to achieve higher contrast in magnetic resonance imaging (MRI); and (2) radioactive metal ions for tumor imaging in single-photon-emission tomography (SPECT) or position emission tomography (PET) and/or in radioisotope-mediated radiation therapy. Thus, appropriately radiolabeled phthalamide chelates can be imaged noninvasively in nuclear medicine employing SPECT or PET. See, for example, Margerum et al., U.S. Pat. No. 6,010,681; and Woodburn et al., U.S. Pat. No. 6,022,526.

Separations

In another preferred embodiment, the specificity of the compounds of the invention for particular ions in solution is exploited to separate those ions from other solutes, including ions for which a compound of the invention has a lower affinity or specificity. In a preferred embodiment, the PLs are used to separate one lanthanide ion from another. Many examples of ion selective or ion specific chelating agents are known in the art. See, for example, Izatt, et al. Synthesis of Macrocycles Wiley-Interscience, New York, 1987; and Martell et al., Determination and Use of Stability Constants, $2^{nd}$ Ed., VCH Publishers, New York, 1992.

The materials, methods and devices of the present invention are further illustrated by the examples which follow. These examples are offered to illustrate, but not to limit the claimed invention.

EXAMPLES

Example 1 illustrates the synthesis of exemplary ligands of the invention and the formation of their metal complexes. The synthetic scheme for the compounds of Example 1 is set forth in FIG. 1.

Example 2 details the x-ray structure determination of the compounds of the invention. Molecular models based on the x-ray crystallographic data are set forth in FIG. 4 and FIG. 5.

Example 3 details the spectrophotometric titration of exemplary compounds of the invention.

Example 4 details the determination of the quantum yield of exemplary compounds of the invention.

Example 5 illustrates high resolution luminescence measurements of exemplary compounds of the invention.

Example 6 illustrates the synthesis of the ligand H22IAM, its analogues and metal chelates. The synthetic scheme for the compounds of Example 6 is set forth in FIG. 8.

Example 7 illustrates the synthesis of exemplary bicapped ligands of the invention and their metal chelates.

Example 8 sets forth studies on the photophysical and stability properties of complexes with the ligand H22IAM in aqueous solution.

Example 9 describes studies on the photophysical and stability properties of complexes with the ligands H22IAM and bicapped H22IAM in DMSO.

Example 10 illustrates the synthesis of the ligand H22IAM-mono-(N-5aminopentylsuccinamic acid), 18. This ligand has been designed to connect the luminescent lanthanide complex to an immunoreactive species such as antibodies. One of the four 2-hydroxyisophthalamide groups is substituted with a linker terminated with a carboxylic group. The synthetic scheme is set forth in FIG. 9.

Example 11 illustrates the synthesis of the Ligand H22tetra(6-amino-1-hexaneamido)IAM, 23. This ligand has been designed to connect the luminescent lanthanide complex to a biomolecule, such as an immunoreactive species (e.g., antibodies). The four 2-hydroxyisophthalamide groups are substituted with a linker terminated with primary amines. The synthesis of 23 is set forth in FIG. 10.

Figure 21:
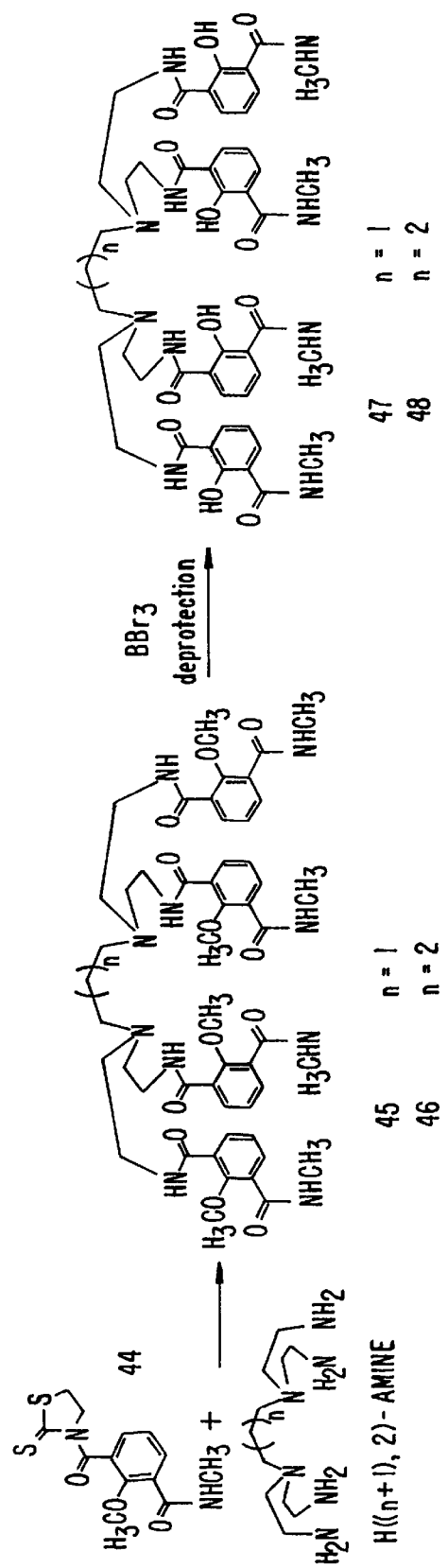
FIG. 21 is a synthetic scheme leading to compounds of the invention having backbones of variable length.

Example 12 illustrates the synthesis of compounds of the invention having backbones of variable length. The synthetic scheme is set forth in FIG. 21.

Example 1

Example 1 illustrates the synthesis of exemplary ligands of the invention and the formation of their metal complexes. The synthetic scheme for the compounds of Example 1 is set forth in FIG. 1.

1.1 Materials and Methods

Unless otherwise noted, starting materials were obtained from commercial suppliers and used without further purification. Flash column chromatography was performed using Merck silica gel 40–70 mesh. Microanalyses were performed by the Microanalytical Services Laboratory, College of Chemistry, University of California, Berkeley. Mass spectra were recorded at the Mass Spectrometry Laboratory, College of Chemistry, University of California, Berkeley. $^1$H and $^{13}$C NMR spectra were recorded on an AMX 300 or AMX 400 Bruker superconducting Fourier transform spectrometer or on a DRX 500 Brucker superconducting digital spectrometer. Infrared spectra were measured using a Nicolet Magna IR 550 Fourier transform spectrometer. The UV/Visible spectra were recorded on a double-beam Perkin-Elmer Lambda 9 UV-Visible spectrophotometer.

1.2 Snthesis of 2-Methoxyisophthalic acid-bis(2-mercaptothiazolide) (1)

2-Methoxyisophthalic acid (0.02 mol), 2-mercaptothiazoline (0.04 mol), and 4-dimethylaminopyridine (20 mg) were dissolved in 150 mL of $CH_2Cl_2$ under a nitrogen atmosphere. 1,3-Dicyclohexylcarbodiimide (0.04 mol) was added to the reaction mixture which gradually became yellow in color. After stirring for 5 hours the reaction mixture was filtered and the filtrate evaporated to dryness to afford a yellow oil. Recrystallization from hot ethyl acetate gave a bright yellow microcrystalline solid. Yield: 55%. IR (film from $CDCl_3$) v1229, 1684, 2955 cm$^{-1}$. $^1$H NMR (300 MHz, $CDCl_3$, 25° C.): δ3.42 (t, J=7.3 Hz, 2H, $CH_2$), 3.89 (s, 3H, $CH_3$), 4.60 (t, J=7.3 Hz, 2H, $CH_2$), 7.13 (t, J=7.7 Hz, 1H, ArH), 7.43 (d, J=7.6 Hz, 2H, ArH). $^{13}$C NMR (400 MHz, $CDCl_3$, 25° C.): δ29.2, 55.6, 62.9, 123.1, 128.1, 131.9, 154.7, 167.1, 200.8. Anal. Calcd (Found) for $C_{15}H_{14}N_2O_3S_4$.0.25 $H_2O$: C, 44.70 (44.75); H, 3.63 (3.53); N, 6.95 (6.82).

1.3 Synthesis of Me$_3$(TRENIAM)-tris(2-mercaptothiazolide) (2)

Tris(2-aminoethyl)amine (TREN) (1.7 mmol) dissolved in 100 mL of $CH_2Cl_2$ was added dropwise to 1 (15.1 mmol) dissolved in 600 mL of $CH_2Cl_2$. The reaction mixture was evaporated to dryness to give a yellow oil. The oil was purified by flash silica column chromatography with 0–4% MeOH/$CH_2Cl_2$. The solvent was evaporated to give the product as a yellow foam. Yield: 70%. IR (film from $CDCl_3$) v1635, 2939, 3386 cm$^{-1}$. $^1$H NMR (500 MHz, $CDCl_3$, 25° C.): δ2.83 (s, 6H, $CH_2$), 3.42 (br t, 6H, $CH_2$), 3.84 (s, 9H, $CH_3$), 4.63 (br t, 6H, $CH_2$), 7.18 (t, J=7.7 Hz, 3H, ArH), 7.39 (d, J=5.7 Hz, 3H, ArH), 7.73 (br t, 3H, NH), 8.01 (d, J=6.0 Hz, 3H, ArH). $^{13}$C NMR (500 MHz, $CDCl_3$, 25° C.): δ29.2, 38.2, 53.6, 55.7, 63.2, 124.4, 127.1, 129.1, 132.2, 134.1, 155.6, 165.0, 167.3, 201.4. Anal. Calcd (Found) for $C_{42}H_{45}N_7O_9S_6$: C, 51.26 (51.26); H, 4.61 (4.71); N, 9.96 (10.09).

1.4 Synthesis of Me$_3$(bicappedTRENSAM) (3)

2 (7.0 mmol) dissolved in 400 mL of $CHCl_3$ and TREN (6.9 mmol) dissolved in 400 mL of $CHCl_3$ were added using laboratory pumps to a 5-L round-bottom flask filled with 2800 mL of $CHCl_3$ and fitted with a mechanical overhead stirrer. The mixture was heated during the addition to ~40° C. under a nitrogen atmosphere. After 24 hrs, the reaction mixture was purified on a silica column, eluted with 0–10% MeOH/$CH_2Cl_2$ gradient. The solvent was evaporated to give the product as a colorless glass. Yield: 46%. IR (film from $CDCl_3$) v1522, 1652, 2939 cm$^{-1}$. $^1$H NMR (500 MHz, $CDCl_3$, 25° C.): δ3.45 (s, 24H, $CH_2$), 3.47 (s, 9H, $CH_3$), 7.15 (t, J=7.7 3H, ArH), 7.54 (br t, 6H, NH), 7.80 (d, J=7.7 Hz, 6H, ArH). $^{13}$C NMR (500 MHz, $CDCl_3$, 25° C.): δ39.4, 56.2, 62.5, 124.2, 128.2, 133.1, 155.7, 166.1. (+)-FABMS: m/z: 773 [M$^+$+H]. Anal. Calcd. (Found) for $C_{39}H_{48}N_8O_9$.2MeOH: C, 58.84 (58.68); H, 6.74 (6.73); N, 13.39 (13.19).

1.5 Synthesis of H$_3$(bicapedTRENSAM).2HBr (4)

3 (0.3 mmol) was dissolved in 30 mL of dry, degassed $CH_2Cl_2$. To the cooled solution was added BBr$_3$ (42.3 mmol) via syringe under a nitrogen atmosphere. After stirring for ~36 hrs the solution was evaporated to dryness to get a pale orange solid. The solid was slowly quenched with MeOH and added to 100 mL of boiling water. The solution was boiled for 3.5 hrs and then allowed to cool, precipitating a white solid. The solid was collected by filtration and oven dried. Yield: 80%. $^1$H NMR (300 MHz, DMSO-d$_6$, 25° C.): δ3.67 (s, 24H, $CH_2$), 6.97 (t, J=7.9 Hz, 3H, ArH), 8.00 (d, J=7.8 Hz, 6H, ArH), 9.10 (br s, 6H, NH). $^{13}$C NMR (500 MHz, DMSO-d$_6$, 25° C.): δ36.2, 57.1, 117.6, 118.9, 134.1, 159.6, 169.0. (+)-FABMS: m/z: 731 [M$^+$+H]. Anal. Calcd. (Found) for $C_{36}H_{44}N_8O_9Br_2$.3H$_2$O: C, 45.68 (45.81); H, 5.32 (5.47); N, 11.84 (11.66).

1.6 Synthesis of [Eu(bicappedTRENSAM)$_2$]Br(DMF)(H$_2$O)$_{10}$ 4 (0.50 mmol) was dissolved in 5 mL of DMSO and 10 mL of water to which the lanthanide salt (0.24 mmol, Ln(NO$_3$)$_3$ or LnCl$_3$) was added. The suspension was heated to reflux until all the solids dissolved (20 min), after which an excess of pyridine (0.5 mL) was added. The mixture was refluxed for 5 hrs and then cooled to room temperature. The solution was evaporated to dryness and the residue was suspended in iPrOH, sonicated, and filtered. Yield: 80%. (+)-FABMS: m/z: 1612 [M$^+$+2H]. Anal. Calcd. (Found) for $C_{75}H_{109}N_{17}O_{29}$BrEu: C, 46.13 (46.32); H, 5.63 (5.65); N, 12.19 (12.24).

1.7 Synthesis of [Tb(bicappedTRENSAM)$_2$]$^+$5

The same procedure was used as described in the synthesis of the Eu$^{3+}$ complex. Yield: 80%. (+)-FABMS: m/z: 1619 [M$^+$+H].

1.8 Results

The macrobicycle ligands were synthesized under high dilution conditions by reaction of the appropriate poly (thiazolide) intermediate with one equivalent of polyamine (Karpishin ET AL., *J. Am. Chem. Soc.* 115: 182 (1993)). This provided the protected ligand as a colorless foams which were deprotected using BBr$_3$. When illuminated at 254 and 365 nm in aqueous solution, the ligand is highly luminescent, emitting blue light.

Synthesis of the metal complexes is performed by suspending the ligand in aqueous solution (or a DMSO/water mixture) followed by addition of the appropriate lanthanide salt. After refluxing for about 30 minutes, an excess of base is added (pyridine or triethylamine) and the reaction is continued for several more hours. The formation of the metal complexes can be monitored by irradiation of the aqueous reaction mixtures with a UV lamp (254 and 365 nm). When illuminated, the reaction mixture of the $Tb^{3+}$ complex emits bright green light, while that of the $Eu^{3+}$ complex emits red light. Both colors are readily visible with the naked eye. The luminescence of both the $Eu^{3+}$ and $Tb^{3+}$ complexes remains very bright after isolation and drying of the compounds. The replacement of the blue fluorescence of the ligand by green or red luminescence when $Tb^{3+}$ or $Eu^{3+}$ are added to the solution suggests that there is efficient energy transfer from the ligand to the metal ion. As coordinated water is known to be very efficient at quenching the excited states of $Eu^{3+}$ ($^5D_0$) and $Tb^{3+}$ ($^5D_4$), the strong luminescence in aqueous solvent suggests that the ligands offer good protection against the binding of water in the first coordination sphere of the lanthanide cation (Bünzli, J.-C. G. *Luminescent Probes;* Bünzli, J.-C. G. and Choppin, G. R., Ed.; Elsevier: Amsterdam, 1989, pp 245).

Example 2

Example 2 details the x-ray structure determination of exemplary compounds of the invention. Molecular models based on the x-ray crystallographic data are set forth in FIG. 4 and FIG. 5.

2.1 X-ray Data Collection, Structure Solutions, and Refinement

All X-ray structure data sets were collected on a Siemens SMART Area Detector diffractometer (SMART, Area-Detector Software Package; Siemens Industrial Automation, Inc.: Madison, 1994). Crystals were mounted on quartz capillaries in Paratone oil and were cooled in a nitrogen stream on the diffractometer. Peak integrations were performed using Siemens SAINT software package (SAINT, SAX Area-Detector Integration Program v. 4.024; Siemens Industrial Automation, Inc.: Madison, 1994). Space group determinations were done by the software XPREP. The structures were solved by direct methods and refined using the SHELXTL software package (PC version, SHELXTL, Crystal Structure Analysis Determination Package; Siemens Industrial Automation, Inc.: Madison, 1994). All hydrogen atoms were fixed at calculated positions and their thermal parameters refined isotropically; all non-hydrogen atoms were refined anisotropically.

2.2 Results

Figure 2:
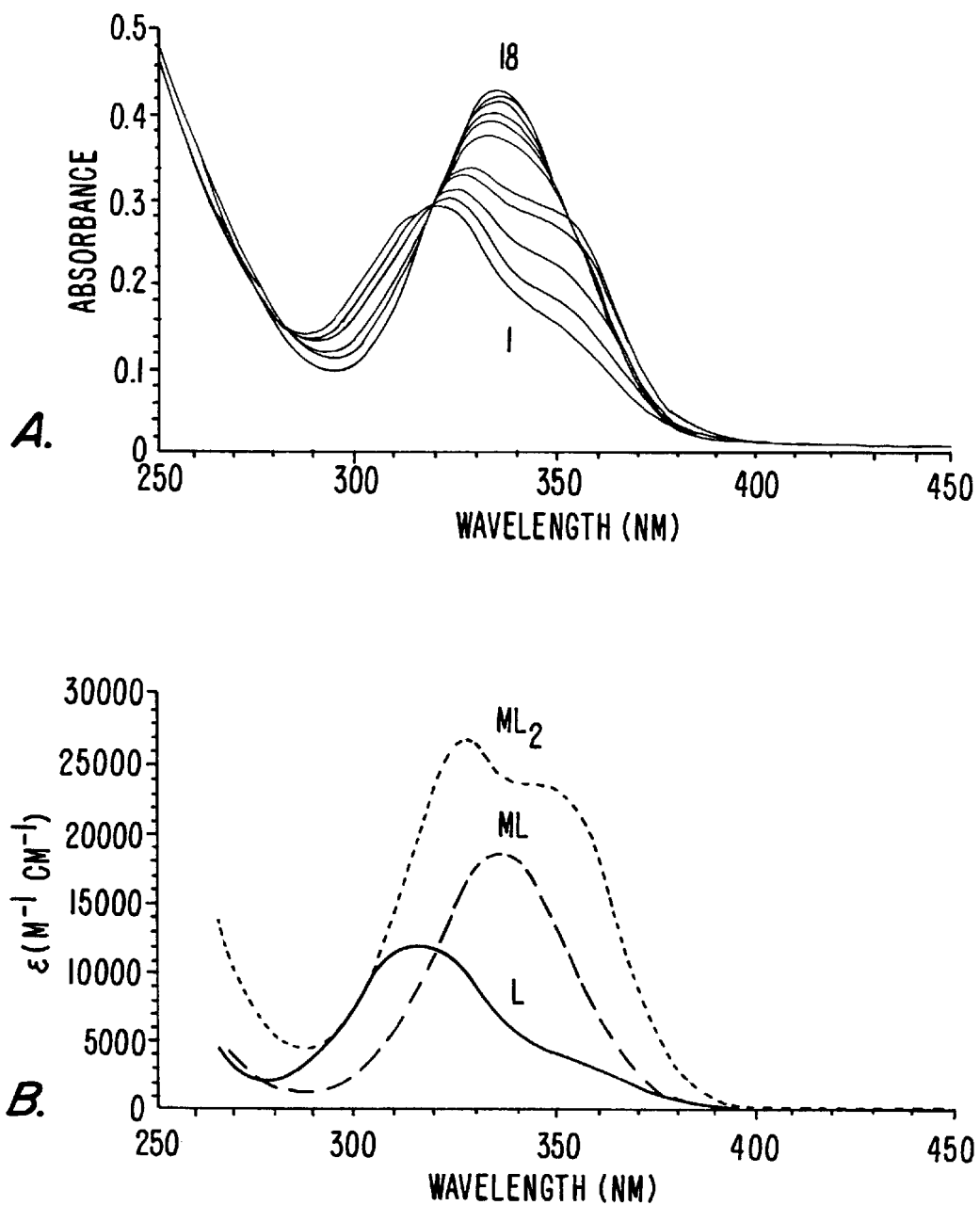
In FIG. 2A, spectra 1 to 18 correspond to increasing concentrations of lanthanide ion.
In FIG. 2B, the solid line is bicapped TRENSAM, the dotted line is Eu[bicapped TRENSAM]$_2$, and the dashed line is Eu[bicapped TRENSAM].
Figure 4:
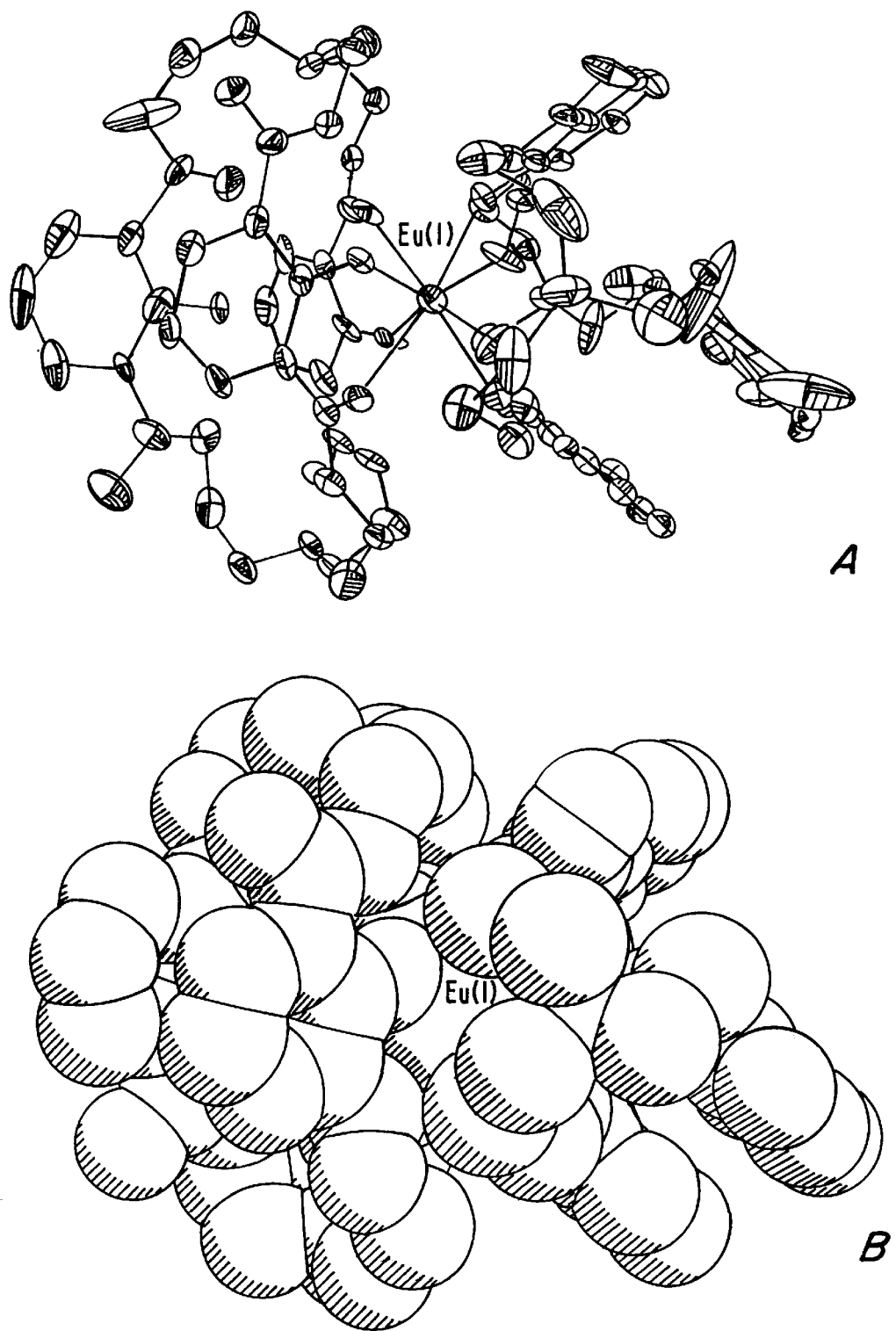
FIGS. 4(A–B) are structural diagrams, ORTEP (A) at 20% probability ellipsoids and space-filling (B), for [Eu(bicappedTRENSAM)$_2$]$^+$. Hydrogens, solvent, and counterion are omitted for clarity.
Figure 5:
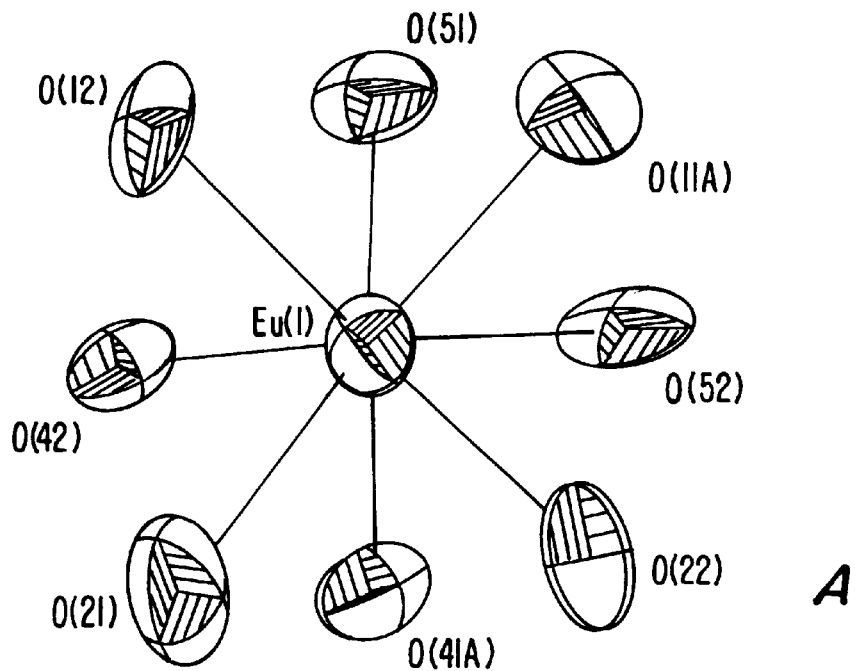
FIGS. 5(A–B) are structural diagrams (ORTEP) of the metal center in [Eu(bicappedTRENSAM)$_2$]$^+$. The metal center coordination polyhedron is a slightly distorted square antiprism (A) with each face of the antiprism formed by one of the bicapped TRENAMSAM ligands (B). 50% probability ellipsoids shown.
Figure 5:
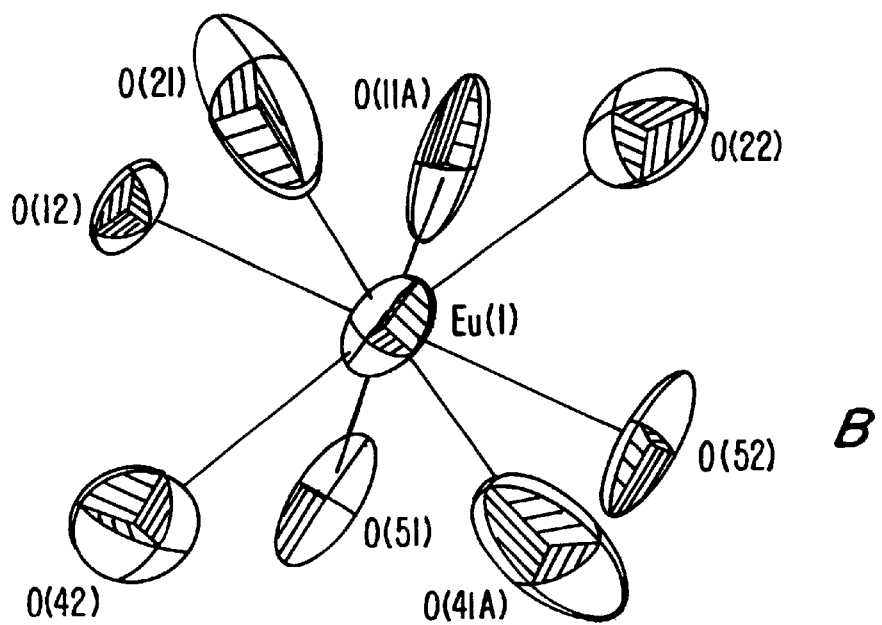

The synthesis of the lanthanide complexes using an excess of ligand allowed for the isolation of exclusively the $ML_2$ complex. Crystals of [Eu(bicapped TRENSAM)$_2$]$^+$ suitable for X-ray diffraction were grown from diffusion of acetone into a wet DMF solution of the complex. The structure shows the wrapping of two ligands of bicapped TRENSAM around the hemispheres of the metal center (FIG. 4). The ligands approach the metal in an orthogonal fashion, about 90° offset from one another. The $Eu^{3+}$ metal center is eight coordinate using two of the three binding units from each of two different cryptates. The coordination polyhedron around $Eu^{3+}$ can be described as a slightly distorted square-antiprism with each face of the antiprism made up of one of the macrobicycles (FIG. 5). See, Kepert, D. L. *Inorganic Stereochemistry;* Springer-Verlag: Berlin, 1982. The third arm of each macrobicycle does not coordinate, in a fashion similar to that seen in some metal-oxo macrobicyclic complexes like $MoO_2$[bicapped TRENCAM] (Albrecht, M.; Franklin, S. J.; Raymond, K. N. *Inorg. Chem.* 1994, 33, 5785). The non-coordinating isophthalamide ligands participate in an intramolecular π-π stacking interaction with one of the bound chelators, which may contribute to protecting the metal center from solvent coordination. This non-coordinating chelate may also be responsible for one of the two main bands that appear at low energy on the UV-Vis spectra of this complex (FIG. 2). The space filling model indicates that the assembly of the two ligands around the metal ion provides very effective protection against deactivation of the excited state of the lanthanide metal ions by solvent molecules. The structure also shows that the complex is stabilized in part due to the strong intramolecular hydrogen bond formed between the carboxylamide proton and the deprotonated 2-hydroxyl oxygen of each isophthalamide chelate (Cohen, S. M.; Raymond, K. N. manuscript in preparation 1998)

Example 3

Example 3 details the spectrophotometric titration of exemplary compounds of the invention.

3.1 Spectrophotometric Titrations

Figure 3:
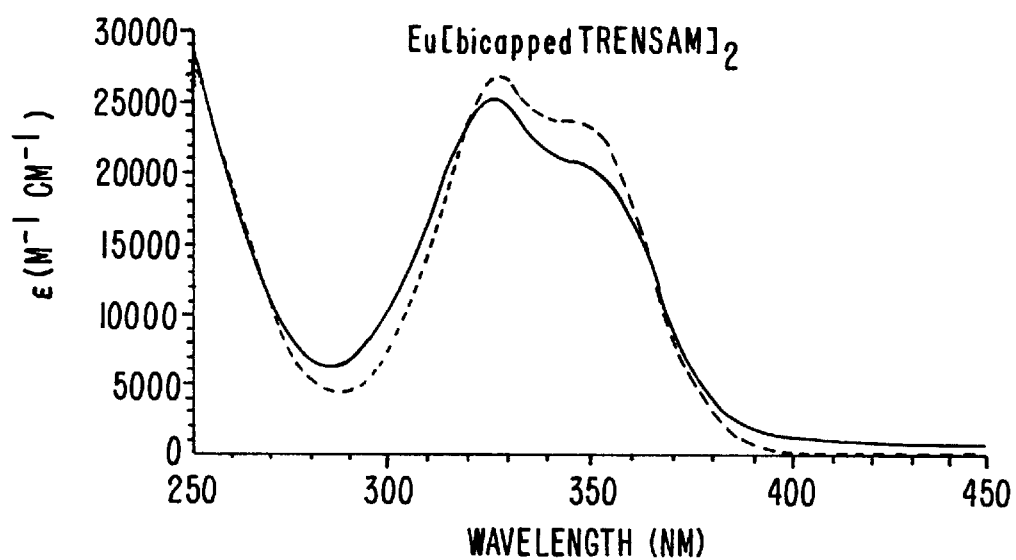
FIG. 3 is an overlay plot of an experimental electronic spectrum (solid line) and calculated electronic spectrum (dotted line) of Eu[bicappedTRENSAM]$_2$.

Batch titration samples were prepared in Millipore purified water with MES buffer, 0.1 M KCl, adjusted to pH=5.78 with KOH. The samples were incubated at 37° C. for 15 hours before measurement to ensure thermodynamic equilibrium had been reached. The ligand concentration was $2.32 \times 10^{-5}$ M for all samples and the $EuCl_3$ was titrated from 0 to 2.2 equivalents. The spectra were recorded on a double-beam Perkin-Elmer Lambda 9 UV-Visible spectrophotometer in 1.0 cm quartz Suprasil cell. The samples were kept at a constant temperature of 25.0±0.2° C. using a Neslab RTE-111 water bath. The treatment of the data was performed with the using the software package SPECFIT $2.10.^{86.1}$ 3.2 Results A batch titration of bicapped TRENSAM with $Eu^{3+}$ was performed in order to evaluate the solution behavior and stability of these complexes. The concentration of the ligand was kept constant and increasing amounts of lanthanide ion were added to a series of samples. The experimental spectra for this titration are shown in FIG. 2A. The spectra show the emergence of new bands with increasing metal concentration. From the experimental spectra it is readily apparent that two different types of metal complexes are formed, one with a single absoption band and one with a double absorption band. Using the program Specfit factor analysis revealed three absorbing species present during the titration (Gampp, H.; Maeder, M.; Meyer, C. J.; Zuberbüler, A. D. *Talanta* 1986, 33, 943). The spectrum for the free ligand was measured independently and the calculated spectrum for the metal species (ML, and $ML_2$) were deconvoluted as shown in FIG. 2B. A comparison of the calculated and observed spectra for the $ML_2$ complex (which was synthesized independently in the presence of excess ligand) further confirms the accuracy of the mathematical treatment of the experimental data (FIG. 3). The stability constants of Ln[bicapped TRENSAM]$_n$ (log$\beta_{11}$ and log$\beta_{12}$ of $Eu^{3+}$ with bicapped TRENSAM) are 7.8 for the ML complex and 14.4 for the $ML_2$ complex, respectively. These stabilities are sufficient for use in fluoroimmunoassay systems (Bünzli, J.-C. G. *Luminescent Probes;* Bünzli, J.-C. G. and Choppin, G. R., Ed.; Elsevier: Amsterdam, 1989, pp 219).

Example 4

Example 4 details the determination of the quantum yield of exemplary compounds of the invention.

4.1 Quantum Yield Determination

The quantum yield of sample solutions containing bicapped TRENSAM, and $Tb^{3+}$[bicappedTRENSAM]$_n$ were determined in water (Millipore purified) relative to quinine sulfate in 0.05 M $H_2SO_4$ (refractive index: 1.338, absolute quantum yield: 0.54). See, Meech, S. R.; Phillips, D. C. *J. Photochem.* 1983, 23, 193. The quantum yields of both $Eu^{3+}$[bicappedTRENSAM]$_n$ complexes were determined with the solutions from the spectrophotometric titration (vide supra) (stoichimetry ratio M:L=0.5 for the $Eu^{3+}$ [bicappedTRENSAM]$_2$ complex and M:L=1.0 for the $Eu^{3+}$ [bicappedTRENSAM] complex). Measurements under ligand excitation conditions were performed on a Spex FluoroMax spectrofluorimeter with an excitation beam-centered 0.100 cm quartz Suprasil luminescence cell. The relative quantum yield ($Q_x/Q_r$) was calculated using Equation 1.

$$Q_x/Q_r = [A_r(\lambda_r)/A_x(\lambda_x)] \cdot [I(\lambda_r)/I(\lambda_x)] \cdot [n^2_x/n^2_r] \cdot [D_x/D_r] \quad \text{Equation 1}$$

The subscript r refers to the reference and x to the samples. The remaining terms in the equation are defined as follows: A is the absorbance at the excitation wavelength, I is the intensity of the excitation light at the same wavelength, n is the refractive index, and D is the integrated luminescence intensity. Measured samples were prepared at concentrations between $1 \times 10^{-3} – 1 \times 10^{-4}$ M.

Example 5

Example 5 illustrates high resolution luminescence measurements of exemplary compounds of the invention.

5.1 High-resolution Luminescence Measurements

High resolution luminescence spectra were measured on a previously described instrumental setup (Bünzli, J.-C. G.; Milicic-Tang, A. *Inorg. Chim. Acta* 1996, 252, 221). Samples were measured as finely powdered samples (La, Eu, Tb)and as monocrystals (Eu). Bidistilled water was used for aqueous; the pH of the solutions was around 6.5. Luminescence spectra were corrected for the instrumental function but not excitation spectra.

5.2 Results

Figure 6:
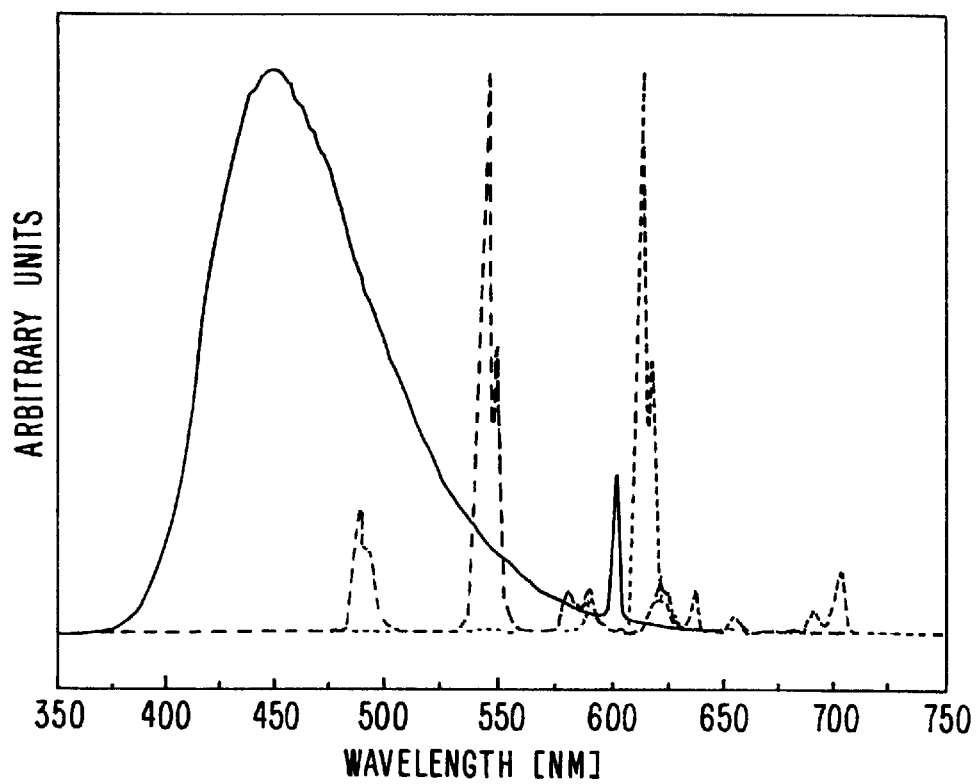
FIG. 6 is an overlay plot of emission spectra of free bicapped TRENSAM (solid line, 4.24·10$^{-4}$ M in water (Millipore purified)), of [Tb(bicappedTRENSAM)$_2$]$^+$ (dashed line, 1.3·10$^{-5}$ M in water (Millipore purified)) and of [Eu(bicappedTRENSAM)$_2$]$^+$ (dotted line, 1.08·10$^{-4}$ M in water (Millipore purified)) with 0.1 M KCl, 0.05 MES buffer, adjusted to pH 5.78 with KOH.
Figure 7:
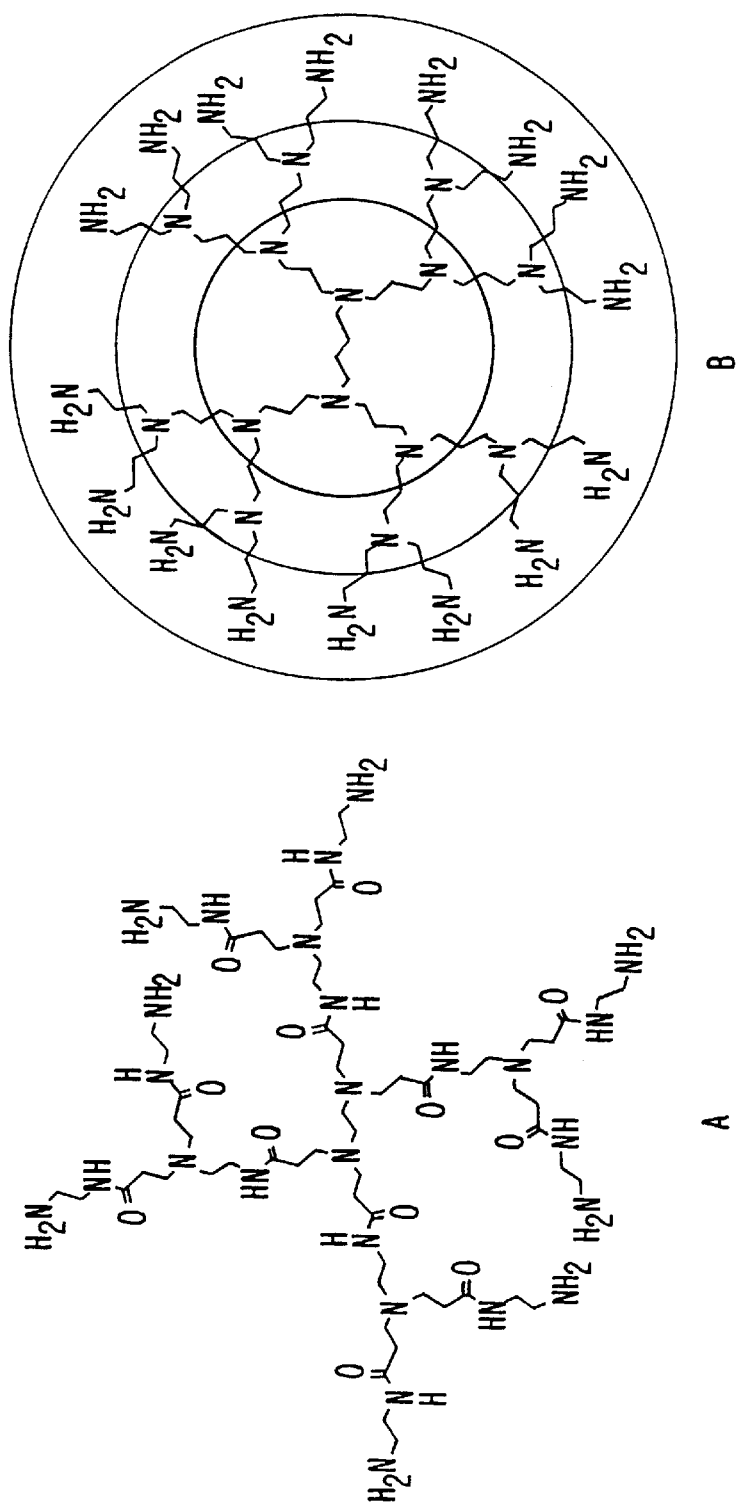
FIGS. 7(A–B) are structural Formulae of representative dendrimers of use in the present invention.

The free ligand bicapped TRENSAM, as well as the $Eu^{3+}$ and $Tb^{3+}$ metal complexes formed with this ligand, are extremely fluorescent in water. FIG. 6 shows the emission spectra in aqueous solution of [Eu(bicappedTRENSAM)$_2$]$^+$, [Tb(bicappedTRENSAM)$_2$]$^+$, and free bicapped TRENSAM excited at 320, 338, and 302 nm, respectively. The emission spectrum of the free ligand bicapped TRENSAM reveals an intense broad fluorescence band centered around 398 mn which gives rise to the blue emitted light. However, upon addition of the metal ion the spectra of the complexes are comprised of only intense narrow lines originating from metal centered f→f transitions. In addition, the broad ligand fluorescence band vanishes completely upon metal complexation, which suggests an efficient conversion of the UV light absorbed by the ligand into the visible red ($Eu^{3+}$) or green ($Tb^{3+}$) luminescence of the lanthanide ions.

High resolution, solid state measurements were performed on a crystalline sample of the [Eu (bicappedTRENSAM)$_2$]$^+$ complex. Analysis of the $^5D_0 \rightarrow {}^7F_J$ transitions in terms of crystal field splitting shows the $^7F_1$ level split into three, almost equally spaced components, pointing to a low site symmetry. $^7F_2$ is split into three components and $^7F_4$ into 5–6 components, which, combined with the very low intensity of the $^5D_0 \rightarrow {}^7F_0$ points to a $D_2$ site symmetry (number of allowed transitions: 0, 3, 3 and 6 for J=0, 1, 2, and 4). The luminescence data therefore confirm the X-ray analysis of the coordination polyhedron around $Eu^{3+}$, described as a distorted square antiprism ($D_{4d} \rightarrow D_4 \rightarrow D_2$). The emission spectrum of a $10^{-4}$ M aqueous solution presents essentially the same features as the emission spectrum of the solid sample at 295 K and the $^5D_0 \leftarrow {}^7F_0$ excitation spectrum shows a single, broad band centered at 17 243 cm$^{-1}$ (fwhh=11.9 cm$^{-1}$), pointing to an $Eu^{III}$ environment in solution similar to the one in the solid state.

The quantum yields of the Eu(bicappedTRENSAM)$_n$ complexes have been determined in water with 0.1 M KCl, 0.05 MES buffer, adjusted to pH 5.78 with KOH. Both Eu(bicappedTRENSAM)$_n$ complexes are highly luminescent with quantum yields for the EuL and EuL$_2$ complexes of approximately 1% and 10%, respectively. The quantum yield measured in water for Tb(bicappedTRENSAM)$_2$ was determined to be at least 36%. The quantum yield of the free ligand in water was measured to be about 9%.

The quantum yields of these complexes are much higher than those found for polypyridine complexes used in recently developed single-step, luminescent assay systems, where the quantum yield in water is 2% (Mathis, G. *Clin. Chem.* 1993, 39, 1953; Mathis, G. *Clin. Chem.* 1995, 41, 1391). In addition, bicapped TRENSAM is unusual in that it forms highly luminescent complexes with both $Tb^{3+}$ and $Eu^{3+}$. In most ligand systems that have been investigated, strong luminescence is only observed with either $Tb^{3+}$ or $Eu^{3+}$, but not both. The origin of why this ligand produces such luminescent complexes with both metal ions will require further spectroscopic measurements. These experiments will determine the overall electronic structure of the complex and in particular the positions of the donating energy levels of the ligand and of the accepting metal orbitals (Petoud, S.; Bünzli, J.-C. G.; Schenk, K. J.; Piguet, C. *Inorg. Chem.* 1997, 36, 1345).

Example 6

Example 6 illustrates the synthesis of the ligand H22IAM, its analogues and metal chelates. The synthetic scheme for the compounds of Example 6 is set forth in FIG. 8.

6.1 Synthesis of tetrakis(thiazoline)Me$_4$H22IAM, 7

Tetrakis(2-aminoethyl)ethylenediamine (H22) (2.8 mmol) was dissolved in 150 mL of $CH_2Cl_2$ was added dropwise to 1 (82.9 mmol) dissolved in 600 mL of $CH_2Cl_2$. The reaction mixture was evaporated to dryness to get a yellow oil. The oil was purified by flash silica column chromatography (0–15% MeOH in $CH_2Cl_2$ gradient). The solvent was evaporated to give the product 7 as a yellow foam. Yield: 83.8%. IR (film from $CH_2Cl_2$) ν1522, 1653, 2942 cm$^{-1}$. $^1$H NMR (500 MHz, CDCl$_3$, 25° C.) δ2.67 (s, 4H, CH$_2$), 2.71 (t, J=6.2 Hz, 8H, CH$_2$), 3.39 (br t, 8H, CH$_2$), 3.48 (s, J=5.8 Hz, 8H, CH$_2$), 3.76 (s, 12H, OCH$_3$), 4.59 (t, J=7.2 Hz, 8H, CH$_2$), 7.14 (t, J=7.7 Hz, 4H, ArH), 7.35 (d, J=5.8 Hz, 4H, ArH), 7.79 (br t, 4H, NH), 7.97 (d, J=6.0 Hz, 4H, ArH). $^{13}$C NMR (500 MHz, CDCl$_3$, 25° C.) δ29.1, 37.9, 50.6, 53.5, 55.7, 63.1, 124.3, 127.2, 129.1, 132.0, 133.9, 155.6, 164.9, 167.3, 201.4. Calcd. (Found) for $C_{58}H_{64}N_{10}O_{12}S_8 \cdot 2CH_2Cl_2$: C, 47.43 (47.45); H, 4.51 (4.52); N, 9.22 (9.54).

6.2 Synthesis of Me$_4$H22IAM, 8

7 (1.1 mmol) was dissolved in 10 mL of $CH_2Cl_2$. To this solution was added 1.5 mL of aqueous methylamine (40% by weight), followed by vigorous shaking of the biphasic mixture. Within 30 sec all the yellow color was gone. The mixture was evaporated to dryness and the remaining residue purified by flash silica column chromatography (0–15% MeOH in $CH_2Cl_2$ gradient). Removal of solvent and oven drying gave 8 as a white foam. Yield: 84.1%. IR (film from CDCl$_3$) ν1539, 1652, 3296 cm$^{-1}$. $^1$H NMR (500 MHz, CDCl$_3$, 25° C.) δ2.74 (br m, 12H, CH$_2$), 2.87 (d, J=4.5 Hz, 12H, NCH$_3$), 3.40 (br d, 8H, CH$_2$), 3.70 (s, 12H, OCH$_3$), 7.02 (t, J=7.5 Hz, 4H, ArH), 7.50 (br d, 4H, NH), 7.62 (d, J=7.5 Hz, 4H, ArH), 7.72 (d, J=8.0 Hz, 4H, ArH), 7.83 (br t, 4H, NH). $^{13}$C NMR (500 MHz, CDCl$_3$, 25° C.) δ26.7, 37.7, 51.7, 53.3, 63.1, 124.5, 127.4, 128.7, 133.1, 133.5, 155.6, 165.5, 166.2. Calcd. (Found) for C$_{50}$H$_{64}$N$_{10}$O$_{12}$.2H$_2$O: C, 58.13 (58.30); H, 6.63 (6.59); N, 13.56 (13.75).

63 Synthesis of H$_4$H22IAM.2HBr, 9

8 (0.9 mmol) was dissolved in 40 mL of dry, degassed CH$_2$Cl$_2$. The solution was cooled in an ice bath and BBr$_3$ (48.0 mmol) was added via syringe under a nitrogen atmosphere. The pale yellow slurry was stirred for 48 hrs, after which the solution was slowly quenched with MeOH. The mixture was diluted with water (total volume 100 mL) and boiled until all the yellow color was gone. The resulting colorless solution was boiled to a volume of 50 mL and then cooled, affording a white solid. The product was collected by filtration and oven dried. Yield: 74%. $^1$H NMR (500 MHz, DMSO-d$_6$, 25° C.) δ2.81 (d, J=4.5 Hz, 12H, NCH$_3$), 3.48 (br s, 8H, CH$_2$), 3.76 (br s, 12H, CH$_2$), 6.92 (t, J=7.5 Hz, 4H, ArH), 7.97 (d, J=7.6 Hz, 4H, ArH), 8.02 (d, J=7.6 Hz, 4H, ArH), 8.87 (br s, 4H, NH), 8.97 (br s, 4H, NH), 10.09 (br s, 4H, OH). $^{13}$C NMR (500 MHz, DMSO-d$_6$, 25° C.) δ26.5, 35.0, 52.9, 116.6, 118.5, 119.8, 132.0, 134.6, 160.2, 166.9, 169.4. Calcd. (Found) for C$_{46}$H$_{58}$N$_{10}$O$_{12}$Br$_2$.5H$_2$O: C, 46.32 (46.34); H, 5.75 (5.70); N, 11.74 (11.66). (+)-FABMS: m/z: 941 [M$^+$+H].

6.4 Synthesis of [Eu(H22IAM)]$^+$, 10

8 (0.09 mmol) and EuCl$_2$.7H$_2$O (0.09 mmol, 99.999%) are suspended in a mixture of 5 mL H$_2$O and 1.5 mL MeOH and heated. At reflux temperature the solution is clear and 1.4 mL of pyridine are added. A white solid started to precipitate. The reacting mixture is red when irradiated by UV light at 354 nm. After 20 hours of reaction, the solvent is reduced and the mixture is cooled at 4° C. After filtration of the white solid and drying in a vacuum oven, 95 mg of product are collected. Yield: 81.7%. Calcd. (Found) for EuC$_{46}$H$_{54}$N$_{10}$O$_{12}$.1Br.4H$_2$O: C, 44.45 (44.67); H, 5.03 (5.01); N, 11.27 (11.09).

6.5 Synthesis of [Tb(H22IAM)]$^+$, 11

8 (0.18 mmol) and Tb(NO$_3$)$_3$.6H$_2$O (0.18 mmol, 99.999%) are suspended in a mixture of 11.0 mL H$_2$O and 2.5 mL MeOH. The procedure was similar to what was described for the synthesis of [Eu(H22IAM)]$^+$. Calcd. (Found) for TbC$_{46}$H$_{52}$N$_{10}$O$_{12}$.1Br.5H$_2$O: C, 43.66 (43.70); H, 4.94 (4.97); N, 11.08 (11.20).

6.6 Synthesis of [La(H22IAM)]$^+$, 12

8 (0.05 mmol) and LaCl$_2$.7H$_2$O (0.05 mmol, 99.999%) are suspended in a mixture of 2.5 mL H$_2$O and 1 mL MeOH. The procedure was similar to what was described for the synthesis of [Eu(H22IAM)]$^+$. 46 mg of white product was collected after isolation and drying. Yield: 74.8%. Calcd. (Found) for LaC$_{46}$H$_{54}$N$_{10}$O$_{12}$.1Br.4H$_2$O: C, 44.92 (44.91); H, 5.08 (5.09); N, 11.39 (11.15).

Example 7

Example 7 illustrates the synthesis of exemplary bicapped ligands of the invention and their metal chelates.

7.1 Synthesis of Me$_4$Bicaped H22IAM, 13

7 (2.3 mmol) dissolved in 400 mL of CHCl$_3$ and H22 amine (2.2 mmol) dissolved in 400 mL of CHCl$_3$ were added using laboratory pumps to a 5-L round-bottom flask filled with 2400 mL of CHCl$_3$ and fitted with a mechanical overhead stirrer and a small reflux condenser. The reaction mixture was heated to 55° C. and kept under a nitrogen atmosphere. After ~31 hrs, the mixture was evaporated to dryness and the remaining residue purified by flash silica column chromatography (0–20% MeOH in CHCl$_3$ gradient). The solvent was evaporated to give the product as an pale amber foam. This compound exists as two conformational isomers as indicated by $^1$H and $^{13}$C NMR (this is also found with protected bicapped H22TAM). Only the spectra for the major isomer are reported. Yield: 44.0%. $^1$H NMR (500 MHz, CDCl$_3$, 25° C.) δ2.69 (br s, 32H, CH$_2$), 2.80 (s, 8H, CH$_2$), 3.42 (br s, 12H, OCH$_3$), 7.00 (br t, 4H, ArH), 7.53 (br s, 8H, NH, 7.65 (d, J=7.5 Hz, 8H, ArH). $^{13}$C NMR (500 MHz, CDCl$_3$, 25° C.) δ37.9, 51.2, 53.2, 62.8, 124.4, 128.1, 132.8, 155.4, 165.7. Calcd. (Found) for C$_{56}$H$_{72}$N$_{12}$O$_{12}$.1MeOH.0.5CH$_2$Cl$_2$: C, 58.54 (58.18); H, 6.58 (6.81); N, 14.25 (14.16). (+)-FABMS: m/z: 1106 [M$^{30}$+H], 1144 [M$^+$+K].

7.2 Synthesis of H$_4$Bicapped H22IAM.4HBr, 14

13 (0.74 mmol) was dissolved in 40 mL of dry, degassed CH$_2$Cl$_2$. The solution was cooled in an ice bath and BBr$_3$ (48.0 mmol) was added via syringe under N$_{2(g)}$. The pale yellow slurry was stirred for 24 hrs, after which the solution was slowly quenched with MeOH. The mixture was diluted with MeOH (total volume 100 mL) and boiled until most of the yellow color was gone. The resulting slurry was boiled to a volume of 50 mL and then cooled to affording a beige solid. The product was collected by filtration and oven dried. The ligand undergoes some undetermined conformational dynamics at room temperature which broaden both the $^1$H and $^{13}$C NMR spectrum. Yield: 91%. $^1$H NMR (500 MHz, DMSO-d$_6$, 90° C.), δ3.45/3.77 (br s, 40H, CH$_2$), 6.70 (br t, 4H, ArH), 7.85 (br d, 8H, ArH), 8.64 (br s, 8H, NH). $^{13}$C NMR (500 MHz, DMSO-d$_6$, 25° C.) δ16.8, 37.0 (br), 52.6 (br), 109.4, 118.2, 133.8 (br), 159.9, 167.8 (br). Calcd. (Found) for C$_{52}$H$_{68}$N$_{12}$O$_{12}$Br$_4$.4H$_2$O: C, 43.23 (42.11); H, 5.30 (5.44); N, 11.63 (11.26). (+)-FABMS: m/z: 1050 [M$^+$+H].

7.3 Synthesis of Tb[bicapped]H22IAM, 15

14 (0.50 mmol) was dissolved in 5 mL of DMSO and 10 mL of water to which Tb(NO$_3$)$_3$.6H$_2$O (0.24 mmol, 99.999%) was added. The suspension was heated to reflux (30 min), after which an excess of triethylamine (0.5 mL) was added. The mixture was refluxed for 5 hrs and then cooled to room temperature. The solution was evaporated to remove the water and the remaining solution was diluted with THF to precipitate a white solid. The solid was collected by filtration and oven dried. Yield: 80%. (+)-FABMS: m/z: 1203 [M$^+$+H].

Example 8

Example 8 sets forth studies on the photophysical and stability properties of complexes with the ligand H22IAM in aqueous solution.

8.1 Conditions for the Aqueous Measurements at Low Concentration

To avoid hydrolysis of the lanthanide, it is desirable to use a phosphate buffer when measurements of solution of lanthanide complex are performed below the concentration of $10^{-7}$ M. The reported measurements were measured in solution buffered at pH=7.4 (physiological pH) with 0.01 M potassium phosphate buffer (8.02 mL of K$_2$HPO$_4$+1.98 mL of KH$_2$PO$_4$ diluted to 1000 mL). The phosphate buffer is commonly used in fluoroimmunoassay technology. The pH domain of this buffer is compatible with the measurement conditions of time-resolved fluoroimmunoassays as well as for the conjugation with antibodies.

The strong blue luminescence of the ligand H22IAM can be detected with the naked eye. The maximum of the emission is located around 425 nm. The excitation spectra of the compound reveals to excitation bands at 240 and 340 nm, the latter being more efficient for the excitation of the complex. The maximum of the broad absorption band is located at 340 nm.

Figure 13:
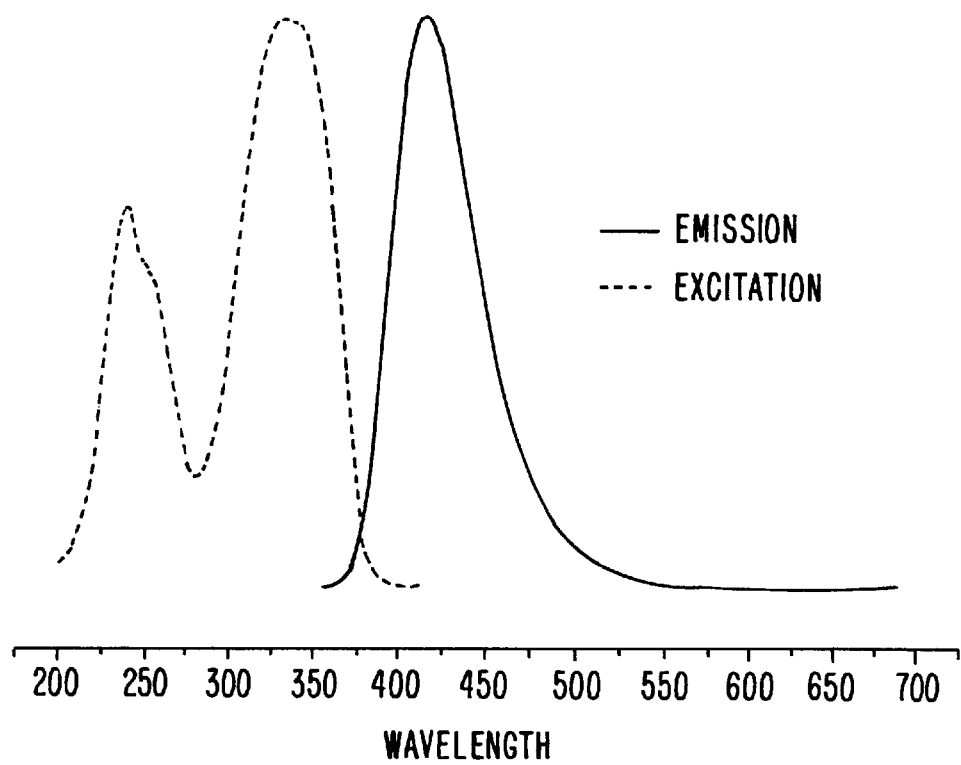
FIG. 13 is a normalized excitation (dotted line, $\lambda_{an}$=417 mn) and emission (full line, $\lambda_{ex}$=350 nm) spectra of the ligand H22IAM ~$10^{-6}$ M in Millipore water.

FIG. 13 is a normalized excitation (dotted line, $\lambda_{an}$=417 nm) and emission (full line, $\lambda_{ex}$=350 nm) spectra of the ligand H22IAM ~$10^{-6}$ M in Millipore water.

Figure 14:
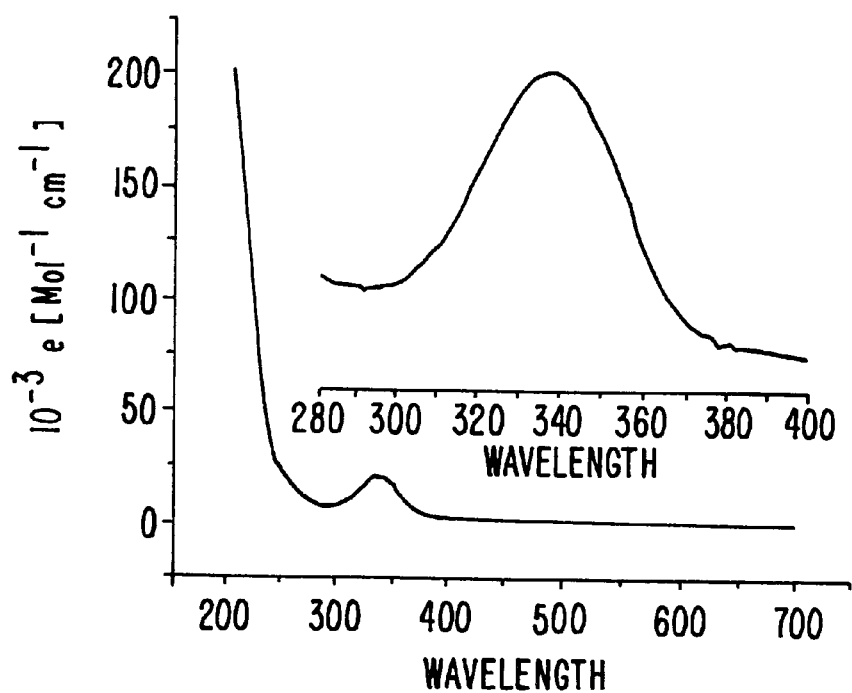
FIG. 14 is a UV/V is spectrum of [Tb(H22IAM)]+ $8.2 \cdot 10^{-7}$M in Millipore water, 1.000 cm cell.

FIG. 14 is a UV/vis spectrum of [Tb(H22IAM)]$^+$ 8.2·$10^{-7}$M in Millipore water, 1.000 cm cell.

No significant emission band arising from the ligand can be observed in the luminescence spectra of the complexes [Tb(H22IAM)]$^+$ and [Eu(H22IAM)]$^+$. This observation indicates that an efficient ligand to metal energy transfer takes place in both Eu$^{3+}$ and Tb$^{3+}$ complexes.

Figure 15:
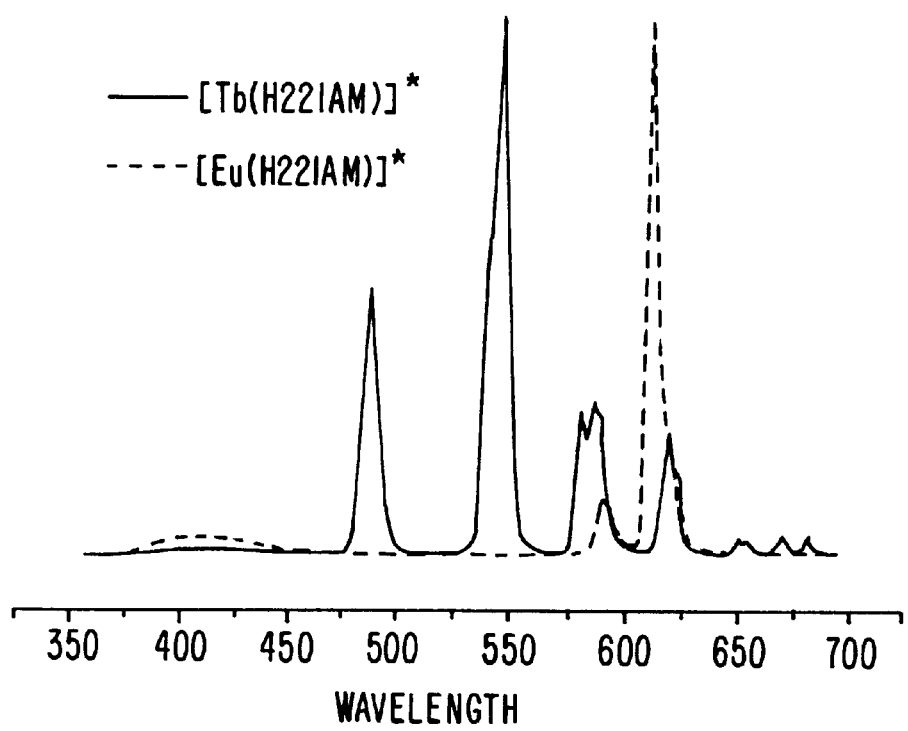
FIG. 15 is a normalized emission spectra of [Tb(H22IAM)]+ and [Eu(H22IAM)]+ in millipore water. [Tb(H22IAM)]+ $8.2 \cdot 10^{-7}$ M, $\lambda_{ex}$=354 nm; [Eu(H22IAM)]+ ~$10$–$6$ M, $\lambda_{ex}$=350 nm.

FIG. 15 is a normalized emission spectra of [Tb(H22IAM)]$^+$ and [Eu(H22IAM)]$^+$ in Millipore water. [Tb(H22IAM)]$^+$8.2·$10^{-7}$ M, $\lambda_{ex}$=354 nm; [Eu(H22IAM)]$^+$ ~$10^{-6}$ M, $\lambda_{ex}$=350 nm.

8.2 Quantum Yields

Table 3 displays the absolute quantum yields of [Tb(H22IAM)]$^+$, at 8.2·$10^{-7}$ M in aerated Millipore water, measured by comparison with quinine sulfate in H$_2$SO$_4$ 0.05 M (absolute quantum yield: 0.5460). Samples and reference were measured at the same absorption and at the same $\lambda_{ex}$. The solutions were prepared 48 hours before the experiment. The solution A was protected from light and the solution B was exposed to the ambient light during the 48 hour delay.

TABLE 3

| Solution | $\lambda_{exc}$/nm | $Q_{Abs}$ |
|---|---|---|
| A | 354 | 0.6045 |
| A | 318 | 0.6051 |
| B | 354 | 0.5557 |
| B | 318 | 0.5111 |

The high value of quantum yield obtained with the complex [Tb(H22IAM)]$^+$ indicates a very efficacy of the energy transfer occurring from the ligand to the Tb$^{3+}$ cation.

8.3 Lifetimes

A preliminary measurement of the lifetime of the Tb$^{3+}$ in a 8.2·$10^{-7}$ M solution of [Tb(H22IAM)]$^+$ was performed using a laser excitation and a fast acquisition system. A unique lifetime value of 2.56 ms was obtained under ligand excitation ($\lambda_{ex}$=352 nm, $\lambda_{an}$=545 nm). This result indicates that the Tb$^{3+}$ cation is well protected by the ligand H22IAM against water coordination, preventing non-radiative deactivation.

8.4 Stability in Water

Figure 16:
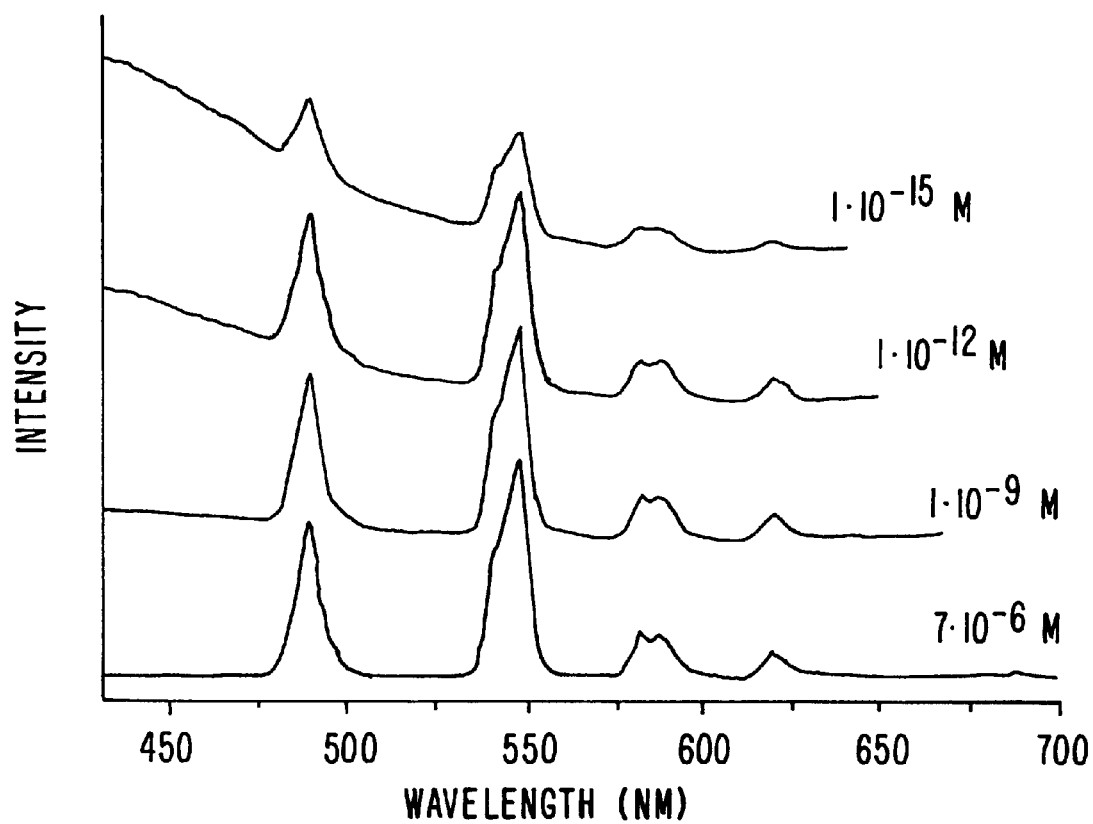
FIG. 16 is an overlay plot of emission spectra of the complex [Tb(H22IAM)]$^+$ in phosphate buffer 0.01 M at various concentration. $\lambda_{ex}$=347 mn.

An estimate of the stability of the [Tb(H22IAM)]$^+$ complex can be obtained by performing a dilution experiment. The luminescence of a molecule is mostly dependent on its quantum yield an to its extinction coefficient. As the lanthanide cations have extremely low extinction coefficient, a ligand coordinated to the lanthanide must be able to act as an "antenna". An "antenna" is a molecule able to absorb a high quantity of UV light and to transfer the resulting energy to the lanthanide cation. This implies that the luminescence of the lanthanide cation can only be observed if the complex is still formed in solution and can be used to estimate the stability of the luminescent lanthanide complex. A stock solution of [Tb(H22IAM)]$^+$ in phosphate buffer was successively diluted and the emission spectra was recorded. The results are set forth in FIG. 16, which contains emission spectra of the complex [Tb(H22IAM)]$^+$ in phosphate buffer 0.01 M at various concentration. $\lambda_{ex}$=347 mn.

These results indicate that the luminescence of the complexes can be detected in a $10^{-15}$ M solution, indicating a very high thermodynamic stability of this complex. This behavior can not be the results of a kinetic inertness since the complexes were synthesized in water.

Example 9

Example 9 describes studies on the photophysical and stability properties of complexes with the ligands H22IAM and bicapped H22IAM in DMSO.

9.1 Quantum Yields

In order to obtain quantitative values on the energy transfer and quenching solvent effect, the relative quantum yields of [Tb(H22IAM)]$^+$ and [Tb(bicapped H22IAM)]$^+$ were determined in DMSO using [Tb(bicapped TRENSAM)$_2$]$^+$ as a reference. The results are reported in Table 3, which displays the relative quantum yields of [Tb(H22IAM)]$^+$ 9.98·$10^{-5}$ M and [Tb(bicappedH22IAM)]$^+$ 9.19·$10^{-5}$ M determined in DMSO by using [Tb(bicapped TRENSAM)$_2$]$^+$ 1.071·$10^{-4}$ M as a reference. Sample and reference were measured at the same absorption and at the same $\lambda_{ex}$ except a where the sample was excited at 378 nm and the reference at 372 nm.

TABLE 3

| Compound | $\lambda_{exc}$/nm | $A(\lambda_{exc})$ | $Q_{Rel}$ |
|---|---|---|---|
| Tb(bicappedTRENSAM)$_2$ | 335 | 0.2316 | 1.0000 |
| | 365 | 0.0926 | 1.0000 |
| | 372 | 0.0462 | 1.0000 |
| Tb(H22IAM) | 335 | 0.2401 | 4.6672 |
| | 365 | 0.1644 | 3.6027 |
| | 372 | 0.0937 | 3.2873 |
| | 378 | 0.0462 | 3.4055[a] |
| Tb(bicappedH22IAM) | 365 | 0.0794 | 1.7757 |
| | 372 | 0.0456 | 1.3610 |

The comparison of the quantum yields of [Ln(H22IAM)]$^+$ and [Ln(bicappedH22IAM)]$^+$ revealed better luminescence properties for the more stable complex formed with [Ln(H22IAM)]$^+$. One other interesting result was obtained from the emission spectrum of the [Tb(bicappedTRENSAM)$_2$]$^+$ complex. In addition to the typical transition arising from the $^5D_4$ levels of the Tb$^{3+}$, a broad band arising from the ligands' electronics levels can be observed at higher energy. This observation reveals the ligand→Ln energy transfer is not totally efficient in DMSO unlike in water where no emission arising from the ligand was observed.

9.2 Stability in DMSO

In order to estimate the stability of [Tb(H22IAM)]$^+$ and [Tb(bicappedH22IAM)]$^+$ in DMSO, the emission spectra of these compounds were measured at different concentrations.

Figure 17:
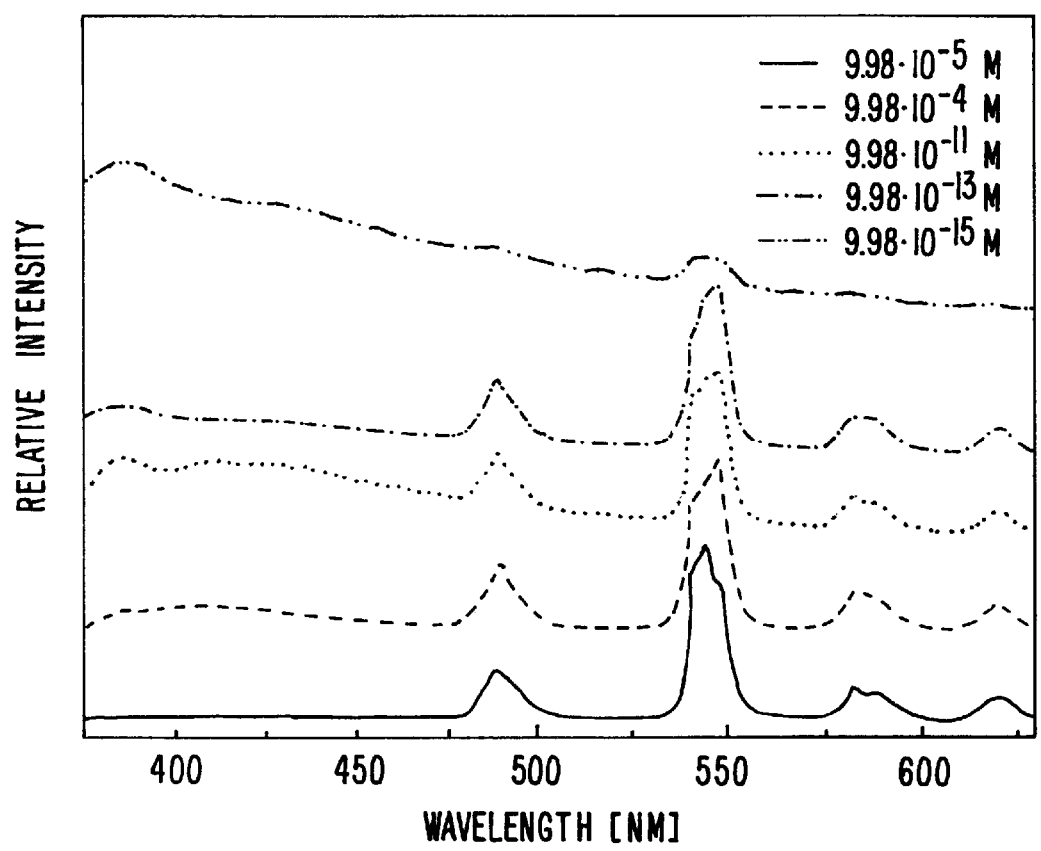
FIG. 17 is an overlay plot of normalized emission spectra of [Tb(H22IAM)]$^+$ at various concentrations. $\lambda_{ex}$=335 nm ($9.98 \cdot 10^{-5}$ M) and $\lambda_{ex}$=347 nm for all others concentrations.
Figure 18:
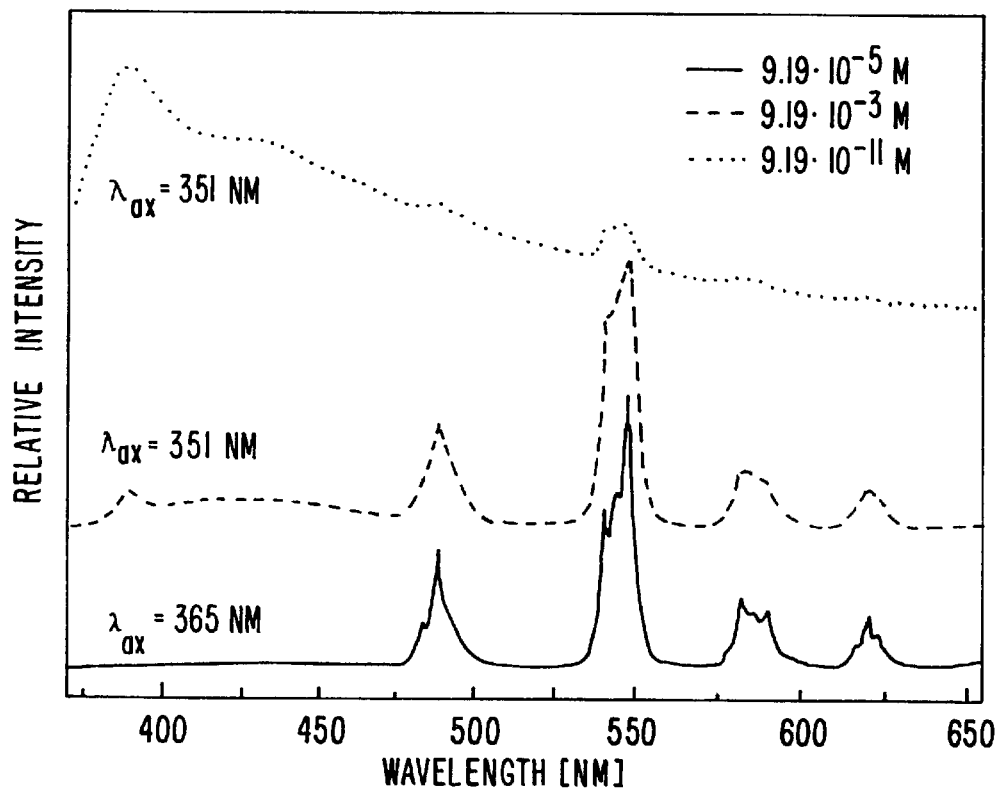
FIG. 18 is an overlay plot of normalized emission spectra of [Tb(bicappedH22IAM)]$^+$ at various concentrations. $\lambda_{ex}$=365 nm ($9.19 \cdot 10^{-5}$ M) and $\lambda_{ex}$=351 nm for all other concentrations.

The results of these studies are displayed in FIG. 17, which displays normalized emission spectra of [Tb(H22IAM)]$^+$ at various concentrations. $\lambda_{ex}$, =335 nm (9.98·$10^{-5}$ M) and $\lambda_{ex}$=347 nm for all others concentrations. The signal arising from the Tb$^{3+}$ could be discriminated and amplified by a time-resolved measurement, and FIG. 18, which displays normalized emission spectra of [Tb(bicappedH22IAM)]$^+$ at various concentrations. $\lambda_{ex}$=365 nm (9.19·$10^{-5}$ M) and $\lambda_{ex}$=351 nm for all other concentrations. The signal arising from the Tb$^{3+}$ could be discriminated and amplified by a time-resolved measurement.

Example 10

Example 10 illustrates the synthesis of the ligand H22IAM-mono-(N-5-aminopentylsuccinamic acid), 18. This ligand has been designed to connect the luminescent lanthanide complex to an immunoreactive species such as antibodies. One of the four 2-hydroxyisophthalamide groups is substituted with a linker terminated with a carboxylic group. The synthetic scheme is set forth in FIG. 9.

10.1 Synthesis of 10-Amino-4-oxo-5-aza-decanoic acid, 16

To a solution of 1,5-pentanediamine (2.5 g, 24 mmol) in dry methanol (20 mL), a solution of succinic acid anhydride (2 g, 20 mmol) in dry methylene chloride (20 mL) was added dropwise in 2 hrs, the product was precipitated as white solid and collected by filtration. Yield 80%. $^1$H NMR (500 MHz, $D_2O$, 25° C.) δ1.280 (quint., J=7.5, 2H, $CH_2$), 1.449 (quint., J=7.5, 2H, $CH_2$), 1.577 (quint., J=7.5, 2H, $CH_2$) 2.337 (s, 4H, $CH_2$), 2.886 (t, J=7.5, 2H, $CH_2$), 3.072 (t, J=7.5, 2H, $CH_2$). $^{13}$C NMR (500 MHz, $D_2O$, 25° C.) δ22.73, 26.22, 27.66, 32.34, 33.13, 38.76, 39.37, 175.72, 180.90.

10.2 $Me_4$H22IAM-mono-(N-5-aminopentyl)succinamic acid derivative, 18

Figure 8:
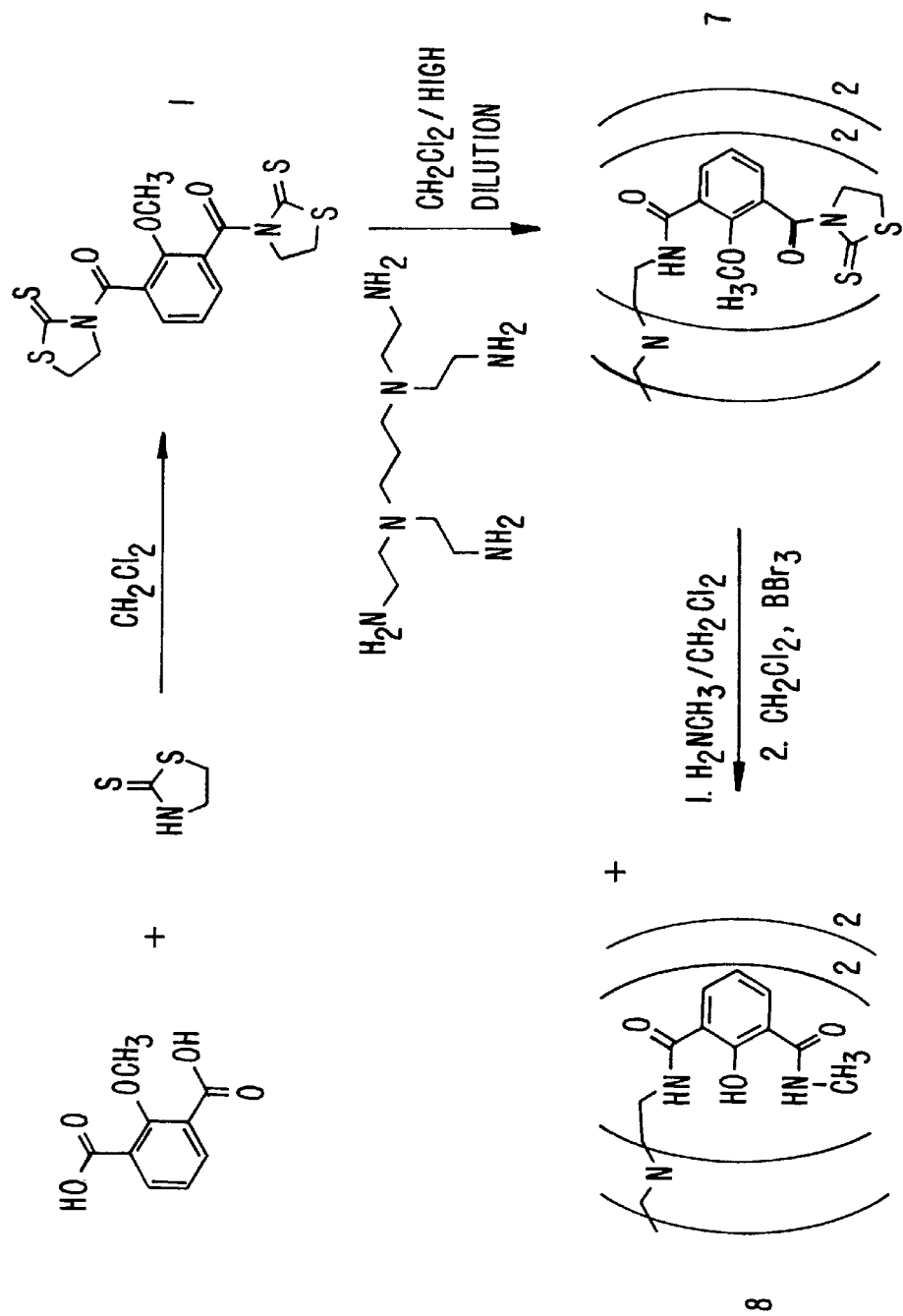
FIG. 8 is a representative synthetic scheme leading to an exemplary tetrapodal ligand of the invention.

To a solution of $Me_4$H22IAMtetrakis(thiazolide) (7, FIG. 8). (5.4 g, 4 mmol) in $CH_2Cl_2$ (500 mL), 16 (0.2 g, 1 mmol) in $CH_2Cl_2$ (200 mL) was added dropwise over 24 hrs and the mixture was stirred for another 24 hrs, then methylamine (0.1 mL, 40% aqueous solution) was added. The characteristic yellow color of the thiazolide disappeared; the solution was evaporated to dryness and the appropriate fractions were separated on a gradient flash silica gel chromatography column (5–10% $CH_3OH$ in $CH_2Cl_2$) to give 0.59 g (51%) pure product as white foam. (+)-FABMS: m/Z: 1154.7 [$MH^+$]. $^1$H NMR (500 MHz, $CDCl_3$, 25° C.) δ1.246 (br s, 2H, $CH_2$), 1.371 (br s, 2H, $CH_2$), 1.469 (br s, 2H, $CH_2$), 2.263 (br s, 2H, $CH_2$), 2.355 (br s, 2H, $CH_2$), 2.737 (br s, 12H, $NCH_2$), 2.858 (s, 4H, $CH_2$), 3.015 (br s, 2H, $CH_2$), 3.275 (br s, 2H, $CH_2$), 3.439 (s, 8H, $NCH_2$), 3.694 (s, 12H, $OCH_3$), 6.930 (s, 1H, NH), 7.020(t, J=7.5, 4H, ArH), 7.5–7.6 (m, 8H, 4NH+4ArH), 7.722 (d, 4H, J=7.0, ArH), 7.94–8.0 (m, 4H, NH). 13C NMR (500 MHz, $CDCl_3$, 25° C.), δ=21.50, 23.8, 26.57, 28.63, 30.66, 31.24, 37.19, 38.90, 39.43, 44.91, 50.88, 52.95, 62.99, 63.03, 124.31, 127.34, 127.40, 128.41, 128.45, 128.66, 132.91, 133.39, 155.46, 155.52, 165.62, 166.12, 173.02, 175.10, 176.51.

10.3 H22IAM-mono-(N-5-aminopentyl-succinamic acid) derivative, 19

18 (0.58 g, 0.5 mmol) was dissolved in dry degassed $CH_2Cl_2$ (20 mL). The solution was cooled in an ice bath and $BBr_3$ (1 mL, 11.4 mmol) was added via syringe under nitrogen. The resulted pale yellow slurry was stirred for 48 hrs, after which the volatile product was removed under vacuum and the residue quenched with methanol (30 mL). The methanol solution was diluted with water (40 mL) and boiled until a colorless transparent solution was obtained; its volume was reduced to 10 mL. The solution was cooled, and a white solid started to precipitate, 46 mg of product was collected by filtration and vacuum dried. The filtrate of this solution was collected by centrifugation and additional 213 mg of solid was obtained after drying. Yield: 40%. (+)-FABMS: m/Z: 1097.7. $^1$H NMR (500 MHz, DMSO-$d_6$, 25° C.) δ1.24–1.60 (m, 6H, $CH_2$), 2.812 (m, 4H, $CH_2$), 3.476 (br s, 12H, $NCH_2$), 3.702 (br s, 8H, $NCH_2$), 6.923 (t, J=7.7, 4H, ArH), 7.684 (br s, 1H, NH), 7.95–8.04 (m, 8H, ArH), 8.818 (br s, 4H, NH), 8.943 (br s, 4H, NH). $^1$H NMR (500 MHz, $D_2O$, 25° C.) δ1.297 (quint, J=7.2, 2H, $CH_2$), 1.444 (quint, J=7.2, 2H, $CH_2$), 1.579 (quint, J=7.2, 2H, $CH_2$), 2.664 (s, 4H, $CH_2$), 2.889 (t, J=7.2, 2H, $CH_2$), 3.099 (t, J=7.2, 2H, $CH_2$), 3.437 (br s, 8H, $NCH_2$) 3.653 (br s, 12H, $NCH_2$), 6.5–6.7 (m, 4H, ArH), 7.3–7.5 (m, 8H, ArH). Calcd. (Found) for $C_{54}H_{69}N_{11}O_{15}(HBr)_2.9H_2O$: C, 45.16 (45.14); H, 5.49 (6.25); N, 10.46 (10.73).

10.4 Tb[H22IAM-mono-(N-5-aminopentyl-succinamic acid) derivative], 19

18 (0.042 mmol) and $Tb(NO_3)_3.6H_2O$ (0.042 mmol, 99.999%) were suspended in 30 mL of MeOH. The suspension was heated until reflux and became clear. The solvent was reduced to 7 ml and a large excess of pyridine was added. A white solid that strongly emits a green color under UV irradiation (354 nm) precipitated instantaneously. The suspension was maintained under reflux for 15 hours. After cooling of the solution to 4° C. and filtration of the product, 46 mg of solid were collected after being dried in vacuum oven. Yield: 63%. Calcd. (Found) for $TbC_{54}H_{68}N_{11}O_{15}Br_2(NO_3).7H_2O$: C, 40.09 (39.95); H, 5.11 (4.76); N, 10.39 (10.42).

10.5 Eu[H22IAM-mono-N-5-aminopentyl-succinamic acid derivative], 20

18 (0.014 mmol) was suspended in 12 mL of $H_2O$ containing $EuCl_3.7H_2O$ (0.014 mmol, 99.999%). The suspension was heated until reflux. When the solution was clear, an excess of pyridine was added (30 drops). A white precipitate appeared instantaneously and was redissolved upon further pyridine addition. After 15 hours of reflux, the solvent was removed and the white solid was redissolved in MeOH. The solid was obtained by addition of pyridine and a strong red emission was observed upon UV irradiation (354 nm). 11.4 mg of compound was collected after filtration and drying. Yield: 53%. Calcd (Found) for $EuC_{54}H_{68}N_{11}O_{15}Br_2Cl.5H_2O$: C, 41.89 (41.55); H, 5.08 (5.07); N, 9.95 (10.24).

Example 11

Example 11 illustrates the synthesis of the Ligand H22tetra(6-amino-1-hexaneamido)IAM, 23. This ligand has been designed to connect the luminescent lanthanide complex to an immunoreactive species such as antibodies. The four 2-hydroxyisophthalamide groups are substituted with a linker terminated with primary amines. The synthesis of 23 is set forth in FIG. 10.

11.1 Synthesis of 6-(Z-amino)-1-hexylamine, 21

A solution of 1,6-hexanediamine (0.050 mmol) in $CH_2Cl_2$ (50 mL) was neutralized with 1.0 equivalent of hydrochloric acid. To this half neutralized amine solution, a solution of Z-thiazolide in $CH_2Cl_2$ (50 mL) was added slowly in 8 hrs with stirring. The resulted solution was washed with 2 M KOH solution (100 mL) and then evaporated to dryness. The residue was then purified by chromatography (3–15% $CH_3OH$ in $CH_2Cl_2$ gradient), 6-(Z-amino)-1-hexaneamine was obtained as a white semisolid. Yield: 52%. $^1$HNMR (500 MHz, $CDCl_3$, 25° C.) δ1.3193 (br s, 4H, $CH_2$), 1.4255 (br d, 2H, $CH_2$), 1.4875 (br d,), 2.6671 (t, 2H, J=7.0, 2H, $CH_2$), 3.1765 (q, 2H, J=6.5, 2H, $CH_2$), 4.8532 (br s, 1H, NH), 5.0827 (s, 2H, $OCH_2$), 7.28–7.38 (m, 5H, ArH).

11.2 $Me_4$H22tetra(6-Z-amino)-1-hexaneamido)IAM, 22

To a solution of Me4H22tetrakis(thiazolide)IAM (7, FIG. 8) (0.8 mmol) in $CH_2Cl_2$ (50 mL), 21 (4 mmol) was added, the mixture was stirred until the characteristic yellow color of the tetrathiazolide disappears. The reaction mixture was evaporated to dryness, the appropriate fractions were collected from of a gradient flash silica gel column (2–7% $CH_3OH$ in $CH_2Cl_2$) and were evaporated to dryness to gave 0.89 g (59%) pure product as white foam. (+)-FABMS: m/Z: 1874.9 [$MH^+$]. $^1$H NMR (500 MHz, $CDCl_3$, 25° C.) δ1.333 (br s, 16H, $CH_2$), 1.465 (br t, 8H, J=6.5, $CH_2$), 1.556 (br t, 8H, J=6.5, $CH_2$), 2.688 (s, 4H, $CH_2$), 2.720 (t, 8H, J=6.0, $CH_2$), 3.132 (q, 8H, J=6.5, $CH_2$), 3.366 (q, 8H, J=6.5, $CH_2$), 3.460 (q, 8H, J=6.0, $CH_2$), 3.765 (s, 12H, NH), 5.041 (s, 8H, $OCH_2$), 5.096 (s, 8H, NH), 7.073 (t, 4H, J=7.5, ArH), 7.26–7.38 (m, 20H, ArH), 7.517 (t, 4H, J=5.7, NH), 7.675 (d, 4H, J=7.5, ArH), 7.812 (d, 4H, J=7.5, ArH), 7.857 (t, 4H, J=5.5, NH). $^{13}$C NMR (500 MHz, $CDCl_3$, 25° C.) δ26.22, 26.51, 29.31, 29.78, 37.72, 39.70, 40.78, 51.88, 53.40, 63.17, 66.40, 124.61, 127.34, 127.92, 127.96, 129.03, 133.69, 136.59, 155.53, 156.43, 165.44.

11.3 H22tetra(6-amino-1-hexaneamido)IAM, 23

22 (0.25 g, 0.13 mmol) was dissolved in dry degassed $CH_2Cl_2$ (20 mL). The solution was cooled in an ice bath and $BBr_3$ (0.5 mL, 5.7 mmol) was added via syringe under nitrogen. The resulted pale yellow slurry was stirred for 48 hrs, after which the volatile was removed under vacuum and the residue quenched with methanol (20 mL). The methanol solution was diluted with water 40 mL) and boiled until a colorless transparent solution was obtained after reduction of the volume to 10 mL. The solution was cooled, and the compound appeared as a gel that was separated from water by centrifugation. After drying (vacuum oven overnight) 234 mg of white solid was collected. (+)-FABMS: m/Z: 1281.7 [MH$^+$]. $^1$H NMR (500 MHz, DMSO-d$_6$), 25° C.) δ1.310 (br s, 16H, $CH_2$), 1.541 (br s, 16H, $CH_2$), 2.731 (q, 8H, J=6.0, $CH_2$), 3.277 (q, 8H, J=6.0, $CH_2$), 3.468 (br s, 12H, $CH_2$), 3.764 (br s, 8H, $CH_2$), 6.922 (t, 4H, J=7.8, ArH), 7.968 (s, 4H, NH), 8.019 (d, J=7.8, 4H, ArH), 8.084 (d, J=7.8, 4H, ArH), 8.993 (br s, 4, NH).

11.4 Tb[H(2,2) tetra(6-amino-1-hexaneamido)IAM], 24

23 (0.042 mmol) was suspended in 12 mL of a solution of MeOH containing Tb(NO$_3$)$_3$.6H$_2$O (0.042 mmol, 99.999%). The suspension was heated until reflux and the solid dissolved. 45 drops of collidine were added to the resulting solution. A strong green emission of the solution was observed upon UV irradiation. After 13 hours of reflux, the solvent was evaporated until the precipitation of a white solid. The product was filtered and washed with Et$_2$O. After drying of the product (vacuum oven), 67 mg of product was collected. Calcd. (Found) for TbC$_{66}$H$_{96}$N$_{14}$O$_{12}$(NO$_3$)(HBr)$_7$.9H$_2$O: C, 35.65 (35.60); H, 5.44 (5.48); N, 9.45 (9.43).

Example 12

Example 12 illustrates the synthesis of compounds of the invention having backbones of variable length. The synthetic scheme is set forth in FIG. 21.

12.1 Synthesis of 2-Methoxy-1-(2-mercaptothiazolide) isophthalamide methylamide, 44

To a solution of 1 (20 g, 0.050 mol) in methylene chloride (200 mL), a mixture of 2 mL methylamine solution (40% wt in water, d =0.902) and 50 mL isopropanol was added dropwise over 8 h. The reaction mixture was evaporated to dryness and the residue was purified by a gradient flash silica column (1–5% methanol in methylene chloride). 5.8 g of the desired product were obtained as a yellow crystalline solid. Yield 81% based on the methylamine. 7.8 g of unreacted dithiazolide were also recovered during the separation.

$^1$H NMR (500 MHz, CDCl$_3$, 25° C.) (FIG. 14) δ: 3.012 (d, J=5.0, 3H, NHCH$_3$), 3.449 (t, J=7.5, 2H, $CH_2$), 3.866 (s, 3H, OCH$_3$), 4.660 (t, J=7.5, 2H, $CH_2$), 7.227 (t, J=7.5, 1H, ArH), 7.416 (d, J=7.5, 1H, ArH), 7.425 (s, br, 1H, Amide H), 8.124 (d, J=7.5, 1H, ArH). $^{13}$C NMR (500 MHz, CDCl$_3$, 25° C.) (FIG. 15) δ: 26.30, 28.73, 55.32, 62.62, 123.81, 126.78, 128.70, 131.49, 155.06, 164.98, 201.15.

12.2 Synthesis of Me$_4$H(3,2)IAM, 45

To a solution of H(3,2)-amine (1 mmol) in $CH_2Cl_2$ (50 mL), compound 44 (4.8 mmol) was added. The mixture was stirred until TLC reveal that the reaction was ended. The reaction mixture was purified trough a gradient flash silica gel column (2–7% CH$_3$OH in $CH_2Cl_2$). The pure product was obtained as a white foam. Yield 81%.

(+)-FABMS: m/Z: 1011.8 [MH$^{30}$]. $^1$H NMR (500 MHz, CDCl$_3$, 25° C.), δ1.624 (quint, 2H, $CH_2$), 2.524 (t, J=6.5, 4H, $CH_2$), 2.649 (t, 8H, J=6.5, $CH_2$), 2.935 (d, 12H, J=5.0, $CH_2$), 3.448 (q, J=6.5, 8H, $CH_2$), 3.777 (s, 12H, $CH_3$) 7.097 (t, 4H, J=7.5, ArH), 7.451 (t, 4H, J=5.5, Amide H), 7.714 (d, 4H, J=7.5, ArH), 7.813 (t, 4H, J=5.5, Amide H), 7.856 (d, J=7.5, 4H, ArH). $^{13}$C NMR (500 MHz, CDCl$_3$, 25° C.), δ: 24.15, 26.67, 37.83, 52.06, 53.21, 63.09, 124.54, 127.53, 128.41, 133.23, 133.63, 155.60, 165.46, 165.99.

12.3 Synthesis of H$_4$H(3,2)IAM, 47

45 (0.5 mmol) was dissolved in dry degassed $CH_2Cl_2$ (20 mL) and the resulting solution was cooled in an ice bath. $BBr_3$ (11.4 mmol) was added via syringe under nitrogen. The resulted pale yellow slurry was stirred for 48 hrs. The volatile was then removed under vacuum and the residue quenched with methanol (30 mL). The methanol solution was diluted with water (40 mL) and boiled until a colorless transparent solution was obtained and its volume was reduced to 10 mL. The solution was cooled and a white precipitate appeared, which was collected by filtration and dried under vacuum. Yield 62%.

(+)-FABMS: m/Z: 1874.9 [MH$^+$]. $^1$H NMR (500 MHz, CD$_3$OD, 25° C.), δ2.467 (quint, J=6.0, 2H, $CH_2$), 2.871 (s, 12H, $CH_3$), 3.625 (t, 8H, J=6.0, $CH_2$), 3.65–3.75 (m, 8H, $CH_2$), 3.85–3.95 (m, 4H, $CH_2$), 6.734 (t, 4H, J=7.5, ArH), 7.678 (d, 4H, J=7.5, ArH), 7.772 (t, 4H, J=7.5, ArH).

12.4 Synthesis of Me$_4$H(4,2)IAM, 46

This compound was prepared by using the same procedure as described for compound 45 except H(4,2)-amine being used instead of H(3,2)-amnine. Yield 84%.

(+)-FABMS: m/Z: 1025.9 [MH$^+$]. $^1$H NMR (500 MHz, CDCl$_3$, 25° C.), δ1.412 (s,br, 4H, $CH_2$), 2.490 (s,br, 4H, $CH_2$), 2.463 (t, 8H, J=6.0, $CH_2$), 2.945 (d, 12H, J=5.0, $CH_2$), 3.464 (q, J=6.5, 8H, $CH_2$), 3.767 (s, 12H, $CH_3$), 7.111 (t, 4H, J=7.5, ArH), 7.396 (q, 4H, J=5.0, Amide H), 7.752 (d, 4H, J=7.5, ArH), 7.795 (t, 4H, J=5.0, Amide H), 7.839 (d, J=7.5, 4H, ArH). $^{13}$C NMR (500 MHz, CDCl$_3$, 25° C.), δ: 24.01, 26.23, 37.64, 49.72, 52.58, 52.41, 53.64, 62.65, 124.03, 127.29, 128.00, 132.79, 133.00, 155.29, 165.20, 165.87.

12.5 Synthesis of H$_4$H(4,2)IAM, 48

This compound was deprotected by the classical BBr$_3$ deprotection procedure described for compound 47. The pure material was collected as a white solid. Yield 71%.

(+)-FABMS: m/Z: 969.7 [MH$^+$]. $^1$H NMR (500 MHz, DMSO-d$_6$, 25° C.), δ1.766 (s,br, 4H, $CH_2$), 2.812 (d, J=5.0, 12H, $CH_3$), 3.31 (s,br, 4H, $CH_2$), 3.386 (s,br, 8H, $CH_2$), 3.714 (d,br, J=5.5, 8H, $CH_2$), 6.948 (t, 4H, J=7.5, ArH), 7.984 (d, 8H, J=7.5, ArH), 8.844 (t, J=5.5, 4H, AmideH), 8.984 (d,br, J=5.5, 4H, AmideH), 9.549 (s,br, 2H, phenolH). $^1$H NMR (500 MHz, D$_2$O—NaOD, 25° C.), δ1.313 (s,br, 4H, $CH_2$), 2.388 (s,br, 4H, $CH_2$), 2.593 (t, J=6.0, 8H, $CH_2$), 2.755 (s,br, 12H, $CH_3$), 3.343 (t, J=6.0, 8H, $CH_2$), 6.477 (t, 4H, J=7.5, ArH), 7.816 (d, 8H, J=7.5, ArH).

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications are incorporated herein by reference.

What is claimed is:

1. A luminescent lanthanide metal chelate comprising a metal ion of the lanthanide series and a complexing agent comprising at least one moiety derived from 2-hydroxy-1,3-benzenedicarboxylic acid.

2. The chelate according to claim 1, having a quantum yield of at least about 0.1.

3. The chelate according to claim 2, wherein said lanthanide metal ion is a member selected from europium, terbium and combinations thereof.

4. The chelate according to claim 1, further comprising at least one salicylamidyl moiety.

5. A luminescent lanthanide metal chelate according to claim 1 wherein said at least one moiety derived from 2-hydroxy-1,3-benzenedicarboxylic acid has the formula:

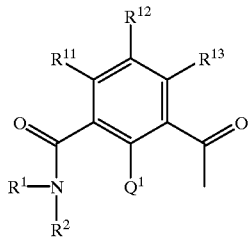

in which
  $R^1$, and $R^2$ are members independently selected from the group consisting of H, alkyl and substituted alkyl groups;
  $R^{11}$, $R^{12}$, and $R^{13}$ are members independently selected from alkyl, substituted alkyl, H, —$NR^{14}R^{15}$, —$NO_2$, —$OR^{16}$, —$COOR^{17}$,
    wherein, $R^{14}$, $R^{15}$, $R^{16}$ and $R^{17}$ are members independently selected from the group consisting of H, alkyl and substituted alkyl, wherein $R^{12}$ can optionally form a, ring with $R^{11}$, $R^{13}$ or both, said ring being a member independently selected from the group of ring systems consisting of cyclic alkyl, substituted cyclic alkyl, aryl, substituted aryl, heteroaryl, substituted heteroaryl, heterocyclyl and saturated heterocyclyl ring systems; and
  $Q^1$ is —$R^{18}$;
    wherein $R^{18}$ is selected from H, an enzmatically labile group, a hydrolytically labile group and a single negative charge.

* * * * *

UNITED STATES PATENT AND TRADEMARK OFFICE
CERTIFICATE OF CORRECTION

PATENT NO. : 6,515,113 B2
DATED : February 4, 2003
INVENTOR(S) : Kenneth N. Raymond et al.

It is certified that error appears in the above-identified patent and that said Letters Patent is hereby corrected as shown below:

Column 71,
Line 8, kindly replace "A" with -- The --
Lines 12-20, kindly replace
"
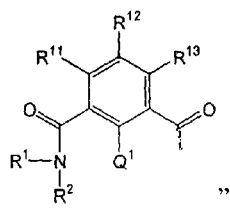
"

with --

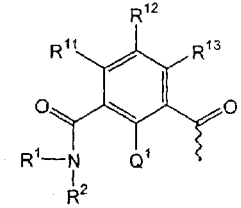

--

Column 72,
Line 17, kindly replace "$Q^1$ is —$R^{18}$" with -- $Q^1$ is —$OR^{18}$ --.

Signed and Sealed this

Twentieth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,515,113 B2
APPLICATION NO. : 09/507630
DATED : February 4, 2003
INVENTOR(S) : Kenneth N. Raymond et al.

It is certified that error appears in the above-identified patent and that said Letters Patent is hereby corrected as shown below:

IN THE SPECIFICATION

In Col. 1, should read below the STATEMENT AS TO RIGHTS TO INVENTIONS MADE UNDER FEDERALLY SPONSORED RESEARCH AND DEVELOPMENT as follows:

This invention was made with government support under DK032999 awarded by the National Institutes of Health and under DE-AC03-76F00098 awarded by the Department of Energy. The government has certain rights in the invention.

Signed and Sealed this
Twenty-third Day of July, 2013

Teresa Stanek Rea
*Acting Director of the United States Patent and Trademark Office*